US012687468B2

(12) United States Patent
O'Neall et al.

(10) Patent No.: US 12,687,468 B2
(45) Date of Patent: Jul. 21, 2026

(54) AGRICULTURAL SAMPLING SYSTEM AND RELATED METHODS

(71) Applicant: Precision Planting LLC, Tremont, IL (US)

(72) Inventors: Matthew O'Neall, Ellsworth, IL (US); Todd Swanson, Morton, IL (US); Dale M. Koch, Tremont, IL (US)

(73) Assignee: Precision Planting LLC, Tremont, IL (US)

( * ) Notice: Subject to any disclaimer, the term of this patent is extended or adjusted under 35 U.S.C. 154(b) by 269 days.

(21) Appl. No.: 18/293,010

(22) PCT Filed: Aug. 22, 2022

(86) PCT No.: PCT/IB2022/057845
§ 371 (c)(1),
(2) Date: Jan. 29, 2024

(87) PCT Pub. No.: WO2023/031726
PCT Pub. Date: Mar. 9, 2023

(65) Prior Publication Data
US 2024/0328905 A1     Oct. 3, 2024

Related U.S. Application Data

(60) Provisional application No. 63/260,772, filed on Aug. 31, 2021, provisional application No. 63/260,777, (Continued)

(51) Int. Cl.
*G01N 1/08* (2006.01)
*A01B 35/18* (2006.01)
(Continued)

(52) U.S. Cl.
CPC ............... *G01N 1/08* (2013.01); *A01B 35/18* (2013.01); *A01B 49/02* (2013.01); *A01B 49/04* (2013.01);
(Continued)

(58) Field of Classification Search
CPC .......... G01N 1/08; G01N 33/245; G01N 1/04; G01N 1/02; A01B 49/02; A01B 49/04; A01B 63/002; A01C 5/062
See application file for complete search history.

(56) References Cited

U.S. PATENT DOCUMENTS

| | | | |
|---|---|---|---|
| 5,355,815 A | 10/1994 | Monson | |
| 6,016,713 A | 1/2000 | Hale | |

(Continued)

FOREIGN PATENT DOCUMENTS

| | | |
|---|---|---|
| CA | 1076806 A | 5/1980 |
| CN | 107192593 A | 9/2017 |

(Continued)

OTHER PUBLICATIONS

Dale M. Koch, U.S. Appl. No. 18/350,847, filed Jul. 12, 2023, 268 pages.

(Continued)

*Primary Examiner* — Francis C Gray

(57)     ABSTRACT

An automated computer-controlled sampling system and related methods for collecting, processing, and analyzing agricultural samples for various chemical properties such as plant available nutrients. The sampling system allows multiple samples to be processed and analyzed for different analytes or chemical properties in a simultaneous concurrent or semi-concurrent manner. Advantageously, the system can process soil samples in the "as collected" condition without drying or grinding. The system generally includes a sample preparation sub-system which receives soil samples col-
(Continued)

lected by a probe collection sub-system and produces a slurry (i.e. mixture of soil, vegetation, and/or manure and water), and a chemical analysis sub-system which processes the prepared slurry samples for quantifying multiple analytes and/or chemical properties of the sample. The sample preparation and chemical analysis sub-systems can be used to analyze soil, vegetation, and/or other samples. A soil collection system is disclosed which captures and directs samples to the sampling system for processing.

20 Claims, 75 Drawing Sheets

Related U.S. Application Data filed on Aug. 31, 2021, provisional application No. 63/260,776, filed on Aug. 31, 2021.

(51) Int. Cl.

| | |
|---|---|
| *A01B 49/02* | (2006.01) |
| *A01B 49/04* | (2006.01) |
| *A01B 63/00* | (2006.01) |
| *G01N 1/02* | (2006.01) |
| *G01N 1/04* | (2006.01) |
| *G01N 33/24* | (2006.01) |
| *A01B 79/00* | (2006.01) |
| *A01C 5/06* | (2006.01) |

(52) U.S. Cl.
CPC ............. *A01B 63/002* (2013.01); *G01N 1/02* (2013.01); *G01N 1/04* (2013.01); *G01N 33/245* (2024.05); *A01B 79/005* (2013.01); *A01C 5/062* (2013.01)

(56) References Cited

U.S. PATENT DOCUMENTS

| | | | |
|---|---|---|---|
| 6,363,803 B1 | 4/2002 | Hubers | |
| 6,393,926 B1 | 5/2002 | Bowersox, Jr. et al. | |
| 6,820,887 B1 | 11/2004 | Riggle | |
| 8,955,401 B1 | 2/2015 | Burton | |
| 9,116,078 B1 | 8/2015 | Scheiderer et al. | |
| 2012/0241180 A1* | 9/2012 | Renyer | A01C 5/064 |
| | | | 172/394 |
| 2014/0251032 A1* | 9/2014 | Scheiderer | G01N 1/04 |
| | | | 73/864.43 |
| 2018/0124992 A1 | 5/2018 | Koch et al. | |
| 2020/0100418 A1* | 4/2020 | Kornecki | A01B 33/082 |
| 2021/0016286 A1 | 1/2021 | Swanson et al. | |
| 2021/0208123 A1 | 7/2021 | Swanson et al. | |
| 2021/0268456 A1 | 9/2021 | Swanson et al. | |
| 2021/0341452 A1 | 11/2021 | Swanson et al. | |
| 2022/0196628 A1 | 6/2022 | Swanson et al. | |
| 2023/0133335 A1 | 5/2023 | Swanson et al. | |
| 2023/0144670 A1 | 5/2023 | Swanson et al. | |
| 2023/0151810 A1* | 5/2023 | O'Neall | F04B 43/043 |
| | | | 73/64.56 |
| 2023/0173415 A1 | 6/2023 | Swanson et al. | |
| 2023/0189696 A1* | 6/2023 | Sauder | A01C 7/06 |
| | | | 111/187 |

FOREIGN PATENT DOCUMENTS

| | | | | |
|---|---|---|---|---|
| CN | 109085013 A | 12/2018 | | |
| DE | 3612409 A1 | 10/1987 | | |
| EP | 1970493 A2 | 9/2008 | | |
| JP | H1183696 A | 3/1999 | | |
| KR | 101084616 B1 | 11/2011 | | |
| KR | 101106075 B1 | 1/2012 | | |
| WO | WO-2021150572 A1 * | 7/2021 | ............... | A01C 7/06 |
| WO | 2021171120 A1 | 9/2021 | | |
| WO | 2021171121 A1 | 9/2021 | | |
| WO | 2021220082 A1 | 11/2021 | | |
| WO | 2021220083 A1 | 11/2021 | | |
| WO | 2021220084 A1 | 11/2021 | | |
| WO | 2021220085 A1 | 11/2021 | | |
| WO | 2022243793 A1 | 11/2022 | | |
| WO | 2022243794 A1 | 11/2022 | | |
| WO | 2022243795 A1 | 11/2022 | | |
| WO | 2022243796 A1 | 11/2022 | | |
| WO | 2022243797 A1 | 11/2022 | | |
| WO | 2022243806 A1 | 11/2022 | | |
| WO | 2022243807 A1 | 11/2022 | | |
| WO | 2022243808 A1 | 11/2022 | | |
| WO | 2022243809 A1 | 11/2022 | | |
| WO | 2022259073 A1 | 12/2022 | | |
| WO | 2022269388 A1 | 12/2022 | | |
| WO | 2023031725 A1 | 3/2023 | | |
| WO | 2023031726 A1 | 3/2023 | | |
| WO | 2023031727 A1 | 3/2023 | | |
| WO | 2023042032 A1 | 3/2023 | | |
| WO | 2023042033 A1 | 3/2023 | | |
| WO | 2023042035 A1 | 3/2023 | | |
| WO | 2023042036 A1 | 3/2023 | | |
| WO | 2023042037 A1 | 3/2023 | | |
| WO | 2023042038 A1 | 3/2023 | | |
| WO | 2023042039 A1 | 3/2023 | | |
| WO | 2023161727 A1 | 8/2023 | | |
| WO | 2023161728 A1 | 8/2023 | | |
| WO | 2023170480 A1 | 9/2023 | | |
| WO | 2023170482 A1 | 9/2023 | | |
| WO | 2023227959 A1 | 11/2023 | | |
| WO | 2023227960 A1 | 11/2023 | | |
| WO | 2023248015 A1 | 12/2023 | | |
| WO | 2023248016 A1 | 12/2023 | | |
| WO | 2024023728 A1 | 2/2024 | | |
| WO | 2024023729 A1 | 2/2024 | | |

OTHER PUBLICATIONS

European Patent Office, Search Report for related PCT Application No. PCT/IB2022/057844, dated Nov. 18, 2022, 13 pages.
UK Intellectual Property Office, Search report for related UK Application No. GB2113495.2, dated Dec. 3, 2021, 4 pages.

* cited by examiner

Direction of Travel

8003

8000

8001

8021

8020

8002

AF 8024-1

8077-1

8077

8079

8082

8080-2

8080-1

8078

8080

8073-1

8073-4

8076

8081

8073-5

8073-2

8073-3

8073

8040

8058

8029

8027

8050

8058-2

8029

8058-1

8027

8050

8050-2

8050

8050

8027

8028-1

8028-2

8028-3

8028-1

8072A

8040A

8074A

8073A

8040A

8020A

8042A

8040A

8071A

8073A 8073-1A

8073A

8042A

8081A

8040A

Complete Spool Cycle direction
of travel

8001

8009

8002

8108

8000

8100

8103

8106   8107   8113   8109

8110

8102

8111

AF

AX1   8106

8107

AX2

GS

8001

8024

8060

8120

8021 pushes soil displaced
by coulter down
toward knife sample
collection cavity

8160

8040

8120a sample
collection maintain
knife
insertion
depth

8120

8150 squeegee soil from
coulter surface creates
furrow
for knife cuts field
residue and
deflects soil
obstructions

8021

8151

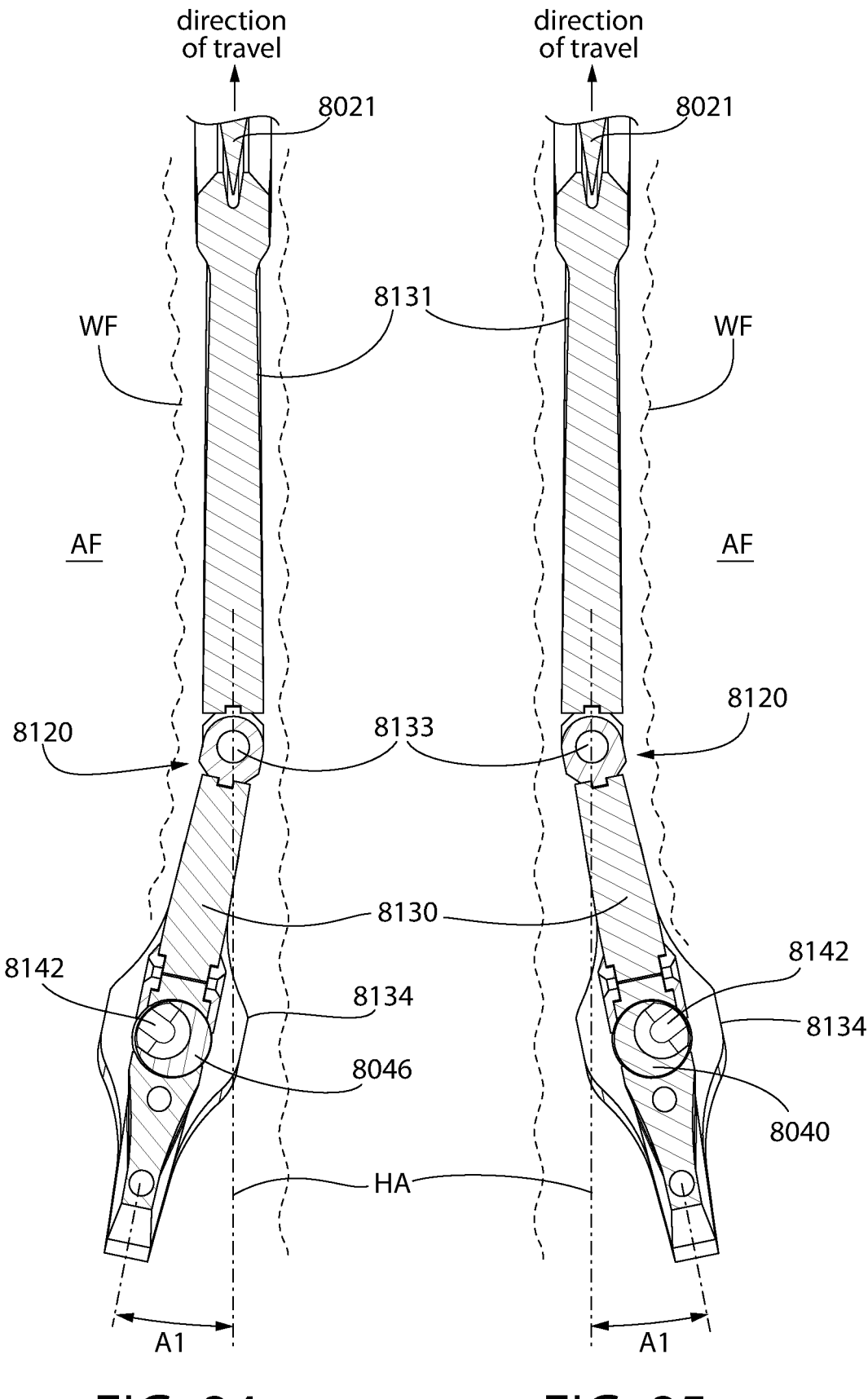
FIG. 84                    FIG. 85

AGRICULTURAL SAMPLING SYSTEM AND RELATED METHODS

CROSS-REFERENCE TO RELATED APPLICATIONS

This application is a national phase entry under 35 U.S.C. § 371 of International Patent Application PCT/IB2022/057845, filed Aug. 22, 2022, designating the United States of America and published in English as International Patent Publication WO 2023/031726 A1 on Mar. 9, 2023, which claims priority to U.S. Application Nos. 63/260,772, filed on 31 Aug. 2021; 63/260,776, filed on 31 Aug. 2021; and 63/260,777, filed on 31 Aug. 2021, all of which are incorporated herein by reference in their entireties.

BACKGROUND

The present disclosure relates generally to agricultural sampling and analysis, and more particularly to a fully automated system for performing soil and other types of agricultural related sampling and chemical property analysis.

Periodic soil testing is an important aspect of the agricultural arts. Test results provide valuable information on the chemical makeup of the soil such as plant-available nutrients and other important properties (e.g. levels of nitrogen, magnesium, phosphorous, potassium, pH, etc.) so that various amendments may be added to the soil to maximize the quality and quantity of crop production.

In some existing soil sampling processes, collected samples are dried, ground, water is added, and then filtered to obtain a soil slurry suitable for analysis. Extractant is added to the slurry to pull out plant available nutrients. The slurry is then filtered to produce a clear solution or supernatant which is mixed with a chemical reagent for further analysis.

Improvements in testing soil, vegetation, and manure are desired.

BRIEF SUMMARY

The present disclosure provides an automated computer-controlled sampling system and related methods for collecting, processing, and analyzing soil samples for various chemical properties such as plant available nutrients (hereafter referred to as a "soil sampling system"). The sampling system allows multiple samples to be processed and analyzed for different analytes (e.g. plant-available nutrients) and/or chemical properties (e.g. pH) in a simultaneous concurrent or semi-concurrent manner, and in relatively continuous and rapid succession. Advantageously, the system can process soil samples in the "as collected" condition without the drying and grinding steps previously described.

The present system generally includes a sample preparation sub-system which receives soil samples collected by a probe collection sub-system and produces a slurry (i.e. mixture of soil, vegetation, and/or manure and water) for further processing and chemical analysis, and a chemical analysis sub-system which receives and processes the prepared slurry samples from the sample preparation sub-system for quantification of the analytes and/or chemical properties of the sample. The described chemical analysis sub-system can be used to analyze soil, vegetation, and/or manure samples.

In one embodiment, the sample preparation system generally includes a mixer-filter apparatus which mixes the collected raw soil sample in the "as sampled" condition (e.g. undried and unground) with water to form a sample slurry. The mixer-filter apparatus then filters the slurry during its extraction from the apparatus for processing in the chemical analysis sub-system. The chemical analysis sub-system processes the slurry and performs the general functions of extractant and color-changing reagent addition/mixing, centrifugating the slurry sample to yield a clear supernatant, and finally sensing or analysis for detection of the analytes and/or chemical properties such as via colorimetric analysis.

Although the sampling systems (e.g. sample collection, preparation, and processing) may be described herein with respect to processing soil samples which represents one category of use for the disclosed embodiments, it is to be understood that the same systems including the apparatuses and related processes may further be used for processing other types of agricultural related samples including without limitation vegetation/plant, forage, manure, feed, milk, or other types of samples. The disclosure herein should therefore be considered broadly as an agricultural sampling system. Accordingly, the present disclosure is expressly not limited to use with processing and analyzing soil samples alone for chemical properties of interest.

BRIEF DESCRIPTION OF THE DRAWINGS

The present disclosure will become more fully understood from the detailed description and the accompanying drawings, wherein like elements are labeled similarly and in which:

FIG. 84 is a first top cross sectional view showing the knife assembly pulled through the soil and the rear blade element pivoted laterally to a first angular position relative to the front blade element hingedly coupled thereto; and FIG. 85 is a second top cross sectional view showing the knife assembly pulled through the soil and the rear blade element pivoted laterally to a second angular position relative to the front blade element hingedly coupled thereto.

Figure 1:
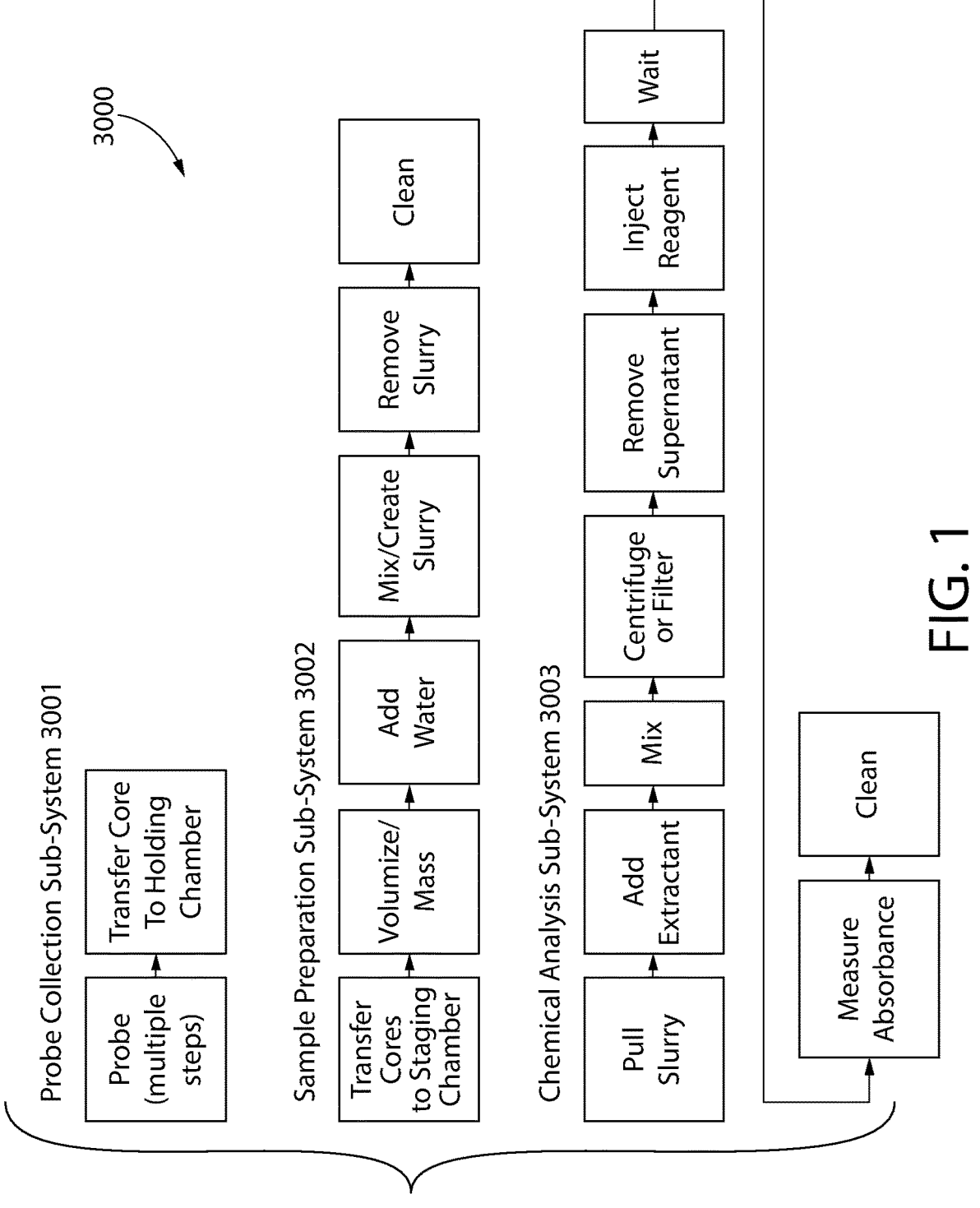
FIG. 1 is a schematic flow diagram of a soil sampling analysis system according to the present disclosure showing the functional aspects of each sub-system of the sampling analysis system.

All drawings are not necessarily to scale. Components numbered and appearing in one figure but appearing un-numbered in other figures are the same unless expressly noted otherwise. Any reference herein to a whole figure number which appears in multiple figures bearing the same whole number but with different alphabetical suffixes shall be constructed as a general refer to all of those figures unless expressly noted otherwise.

DETAILED DESCRIPTION

The features and benefits of the present disclosure are illustrated and described herein by reference to exemplary ("example") embodiments. This description of exemplary embodiments is intended to be read in connection with the accompanying drawings, which are to be considered part of
the entire written description. Accordingly, the disclosure
expressly should not be limited to such exemplary embodi-
ments illustrating some possible non-limiting combination
of features that may exist alone or in other combinations of
features.

In the description of embodiments disclosed herein, any
reference to direction or orientation is merely intended for
convenience of description and is not intended in any way to
limit the scope of the present disclosure. Relative terms such
as "lower," "upper," "horizontal," "vertical,", "above,"
"below," "up," "down," "top" and "bottom" as well as
derivative thereof (e.g., "horizontally," "downwardly,"
"upwardly," etc.) should be construed to refer to the orien-
tation as then described or as shown in the drawing under
discussion. These relative terms are for convenience of
description only and do not require that the apparatus be
constructed or operated in a particular orientation. Terms
such as "attached," "affixed," "connected," "coupled,"
"interconnected," and similar refer to a relationship wherein
structures are secured or attached to one another either
directly or indirectly through intervening structures, as well
as both movable or rigid attachments or relationships, unless
expressly described otherwise.

As used throughout, any ranges disclosed herein are used
as shorthand for describing each and every value that is
within the range. Any value within the range can be selected
as the terminus of the range. In addition, all references cited
herein are hereby incorporated by reference in their entire-
ties. In the event of a conflict in a definition in the present
disclosure and that of a cited reference, the present disclo-
sure controls.

FIG. 1 is a high level schematic diagram flow chart
describing the functional aspects of an agricultural sampling
system 3000 according to the present disclosure. The system
includes multiple sub-systems which operate in concert and
sequence. The sub-systems disclosed herein collectively
provide complete processing and chemical analysis of soil or
other agricultural samples from collection in the agricultural
field, sample preparation and processing, and final chemical
analysis. The agricultural material sampled may be soil in
one embodiment; however, other types of agricultural mate-
rials may be processed and analyzed in the same system
including without limitation vegetation/plants, crop resi-
dues, forage, manure, feed, milk, and other agricultural
related materials of interest in the agricultural, livestock,
diary or similar arts. In the context of soil sampling for
example which is important to crop production and yield, the
agricultural sampling system 3000 advantageously allows
multiple samples to be processed and chemically analyzed
simultaneously for different various plant-available nutrients
or other parameters such as for example without limitation
pH, BpH (buffer pH), etc. . . . This information may be used
to generate nutrient/parameter maps for the agricultural field
to determine the appropriate quantities of soil amendments
needed in different regions of the field to maximize overall
crop production.

In various embodiments, portions of or the entire the
agricultural sampling system 3000 may be incorporated
onboard a motorized sampling vehicle configured to traverse
an agricultural field for collecting and/or processing soil
samples from various zones of the field. This allows a
comprehensive nutrient and chemical profile of the field to
be accurately generated "on-the-fly" in order to quickly and
conveniently identify the needed soil amendments and appli-
cation amounts necessary in real-time for each zone or
region of the field based on quantification of the plant-available nutrient and/or chemical properties in the sample.
The system 3000 advantageously allows multiple samples to
be collected, processed, and chemically analyzed simulta-
neously in parallel for various plant-available nutrients or
other chemical properties and parameters.

The soil sampling system 3000 generally includes a
sample probe collection sub-system 3001, a sample prepa-
ration sub-system 3002, and a chemical analysis sub-system
3003. The sample collection sub-system 3001 and motorized
sampling vehicle are fully described in U.S. Patent Appli-
cation Publication No. 2018/0124992A1 and PCT Publica-
tion No. WO2020/012369. Sample collection sub-system
3001 generally performs the function of extracting and
collecting soil samples from the field. The samples may be
in the form of soil plugs or cores. The collected cores are
transferred to a holding chamber or vessel for further pro-
cessing by the sample preparation sub-system 3002. Other
systems are described in U.S. Application Nos. 62/983,237,
filed on 28 Feb. 2020; 63/017,789, filed on 30 Apr. 2020;
63/017,840, filed on 30 Apr. 2020; 63/018,120, filed on 30
Apr. 2020; 63/018,153, filed on 30 Apr. 2020; 63/191,147,
filed on 20 May 2021; 63/191,159, filed on 20 May 2021;
63/191,166, filed on 20 May 2021; 63/191,172, filed on 20
May 2021; Ser. No. 17/326,050, filed on 20 May 2021;
63/191,186, filed on 20 May 2021; 63/191,189, filed on 20
May 2021; 63/191,195, filed on 20 May 2021; 63/191,199,
filed on 20 May 2021; 63/191,204, filed on 20 May 2021;
Ser. No. 17/343,434, filed on 9 Jun. 2021; 63/208,865, filed
on 9 Jun. 2021; Ser. No. 17/343,536, filed on 9 Jun. 2021;
63/213,319, filed on 22 Jun. 2021; 63/260,772, filed on 31
Aug. 2021; 63/260,776, filed on 31 Aug. 2021; 63/260,777,
filed on 31 Aug. 2021; 63/245,278, filed on 17 Sep. 2021;
63/264,059, filed on 15 Nov. 2021; 63/264,062, filed on 15
Nov. 2021; 63/264,065, filed on 15 Nov. 2021; 63/268,418,
filed on 23 Feb. 2022; 63/268,419, filed on 23 Feb. 2022;
63/268,990, filed on 8 Mar. 2022; 63/269,060, filed 9 Mar.
2022; 63/269,064, filed 9 Mar. 2022; 63/365,243, filed 24
May 2022; 63/365,244, filed 24 May 2022; 63/366,673, filed
20 Jun. 2022; 63/366,674, filed 20 Jun. 2022; 63/369,722,
filed 28 Jul. 2022; 63/369,724, 28 Jul. 2022; 63/369,765,
filed 28 Jul. 2022; 63/369,988, filed 1 Aug. 2022; 63/370,
072, filed 1 Aug. 2022; 63/370,077, filed 1 Aug. 2022;
63/370,081, filed 1 Aug. 2022; and PCT/IB2021/051076,
filed on 10 Feb. 2021; PCT Application Nos. PCT/IB2021/
051077, filed on 10 Feb. 2021; PCT/IB2021/052872, filed
on 7 Apr. 2021; PCT/IB2021/052874, filed on 7 Apr. 2021;
PCT/IB2021/052875, filed on 7 Apr. 2021; PCT/IB2021/
052876, filed on 7 Apr. 2021. Other sampling systems are
described in U.S. Application Nos. 62/983,237, filed on 28
Feb. 2020; 63/017,789, filed on 30 Apr. 2020; 63/017,840,
filed on 30 Apr. 2020; 63/018,120, filed on 30 Apr. 2020;
63/018,153, filed on 30 Apr. 2020; PCT/IB2021/051076,
filed on 10 Feb. 2021; and PCT Application Nos. PCT/
IB2021/051077, filed on 10 Feb. 2021; PCT/IB2021/
052872, filed on 7 Apr. 2021; PCT/IB2021/052874, filed on
7 Apr. 2021; PCT/IB2021/052875, filed on 7 Apr. 2021;
PCT/IB2021/052876, filed on 7 Apr. 2021.

The sample preparation sub-system 3002 generally per-
forms the functions of receiving the soil sample cores in a
mixer-filter apparatus, volumetric/mass quantification of the
soil sample, adding a predetermined quantity or volume of
filtered water based on the volume/mass of soil, and mixing
the soil and water mixture to produce a soil sample slurry,
removing or transferring the slurry from mixer-filter appa-
ratus, and self-cleaning the mixer-filter apparatus for pro-
cessing the next available soil sample. In some embodi-
ments, the filter may be separate from the mixer.

The chemical analysis sub-system 3003 generally performs the functions of receiving the soil slurry from a mixer-filter apparatus of sub-system 3002, adding extractant, mixing the extractant and slurry in a first chamber to pull out the analytes of interest (e.g. plant available nutrients), centrifuging the extractant-slurry mixture to produce a clear liquid or supernatant, removing or transferring the supernatant to a second chamber, injecting a reagent, holding the supernatant-reagent mixture for a period of hold time to allow complete chemical reaction with reagent, measure the absorbance such as via colorimetric analysis, and assist with cleaning the chemical analysis equipment. In some embodiments, the chemical analysis sub-system 3003 may be embodied in a microfluidic device or apparatus, as further described herein.

Figure 2:
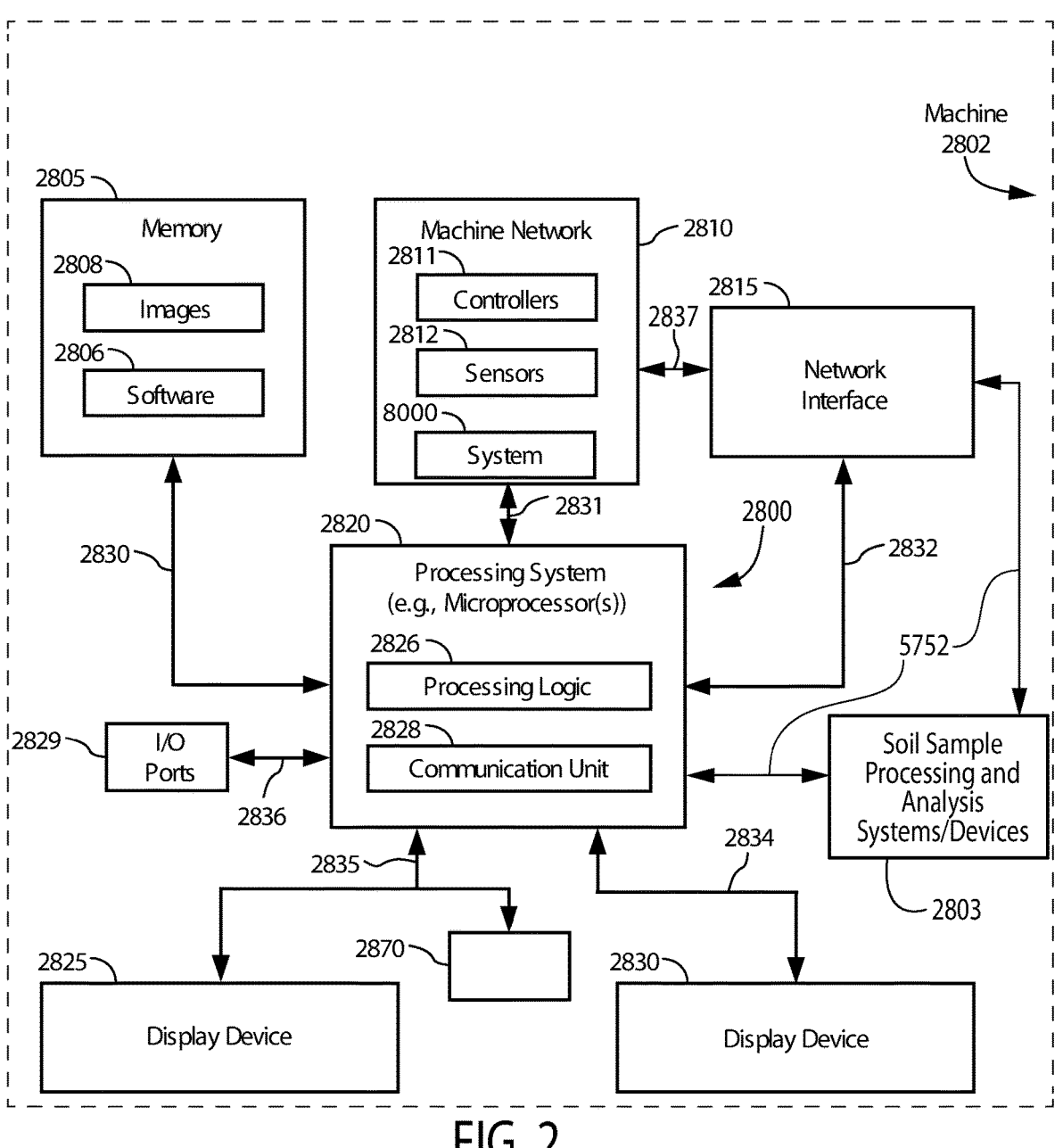
FIG. 2 is a schematic system diagram of a programmable processor-based central processing unit (CPU) or system controller for controlling the systems and apparatuses disclosed herein.

The process described in FIG. 1 and soil sample collection equipment may be automatically controlled and executed by the programmable system controller 2820. The controller may be part of a controller processing system such as that further described herein and shown in FIG. 2, or as disclosed in copending U.S. Patent Application Publication No. 2018/0124992A1 (U.S. patent application Ser. No. 15/806,014). The controller 2820 is operably coupled to the components of the chemical analysis sub-system 3003 disclosed herein (e.g., pumps, valves, centrifuge, compressor (air supply), etc.) for controlling the process sequence and flow of fluids (e.g., water, air, slurry, extractant, reagent, supernatant, etc.) through the system to fully process and analyze the soil or other type agricultural sample. FIG. 2 depicts one embodiment of programmable system controller 2820 applicable to the present application.

The sample collection sub-system 3001 and control system which may be programmed to control operation of sub-system 3001 will now be described in further detail.

Control System

FIG. 2 is a schematic system diagram showing the control or processing system 2800 including programmable processor-based central processing unit (CPU) such as system controller 2820 referenced herein. System controller 2820 may include one or more processors, non-transitory tangible computer readable medium, programmable input/output peripherals, and all other necessary electronic appurtenances normally associated with a fully functional processor-based controller. Control system 2800, including controller 2820, is operably and communicably linked to the different soil sample processing and analysis systems and devices described elsewhere herein via suitable wired or wireless communication links to control operation of those systems and devices in a fully integrated and sequenced manner.

Figure 54:
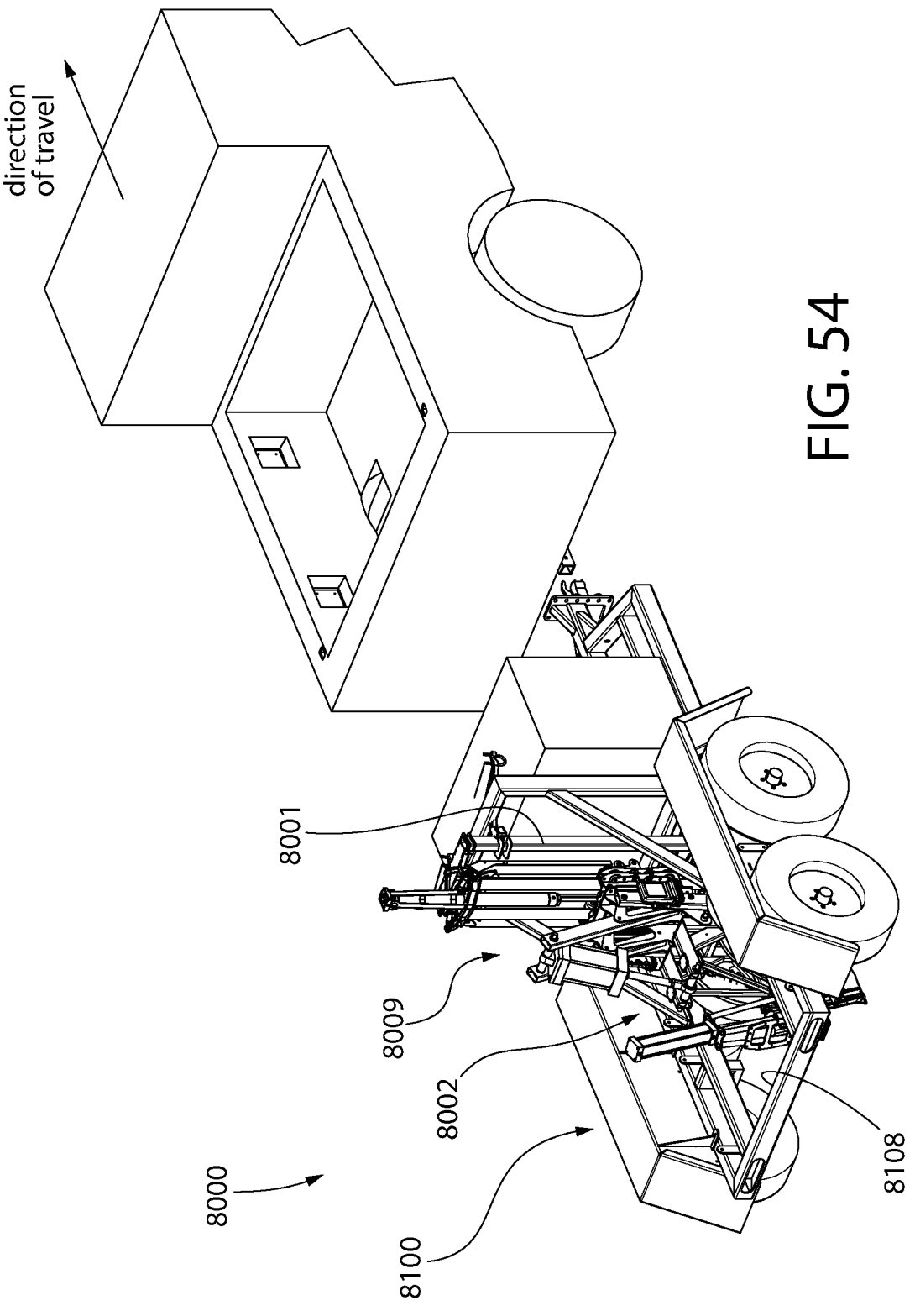
FIG. 54 is a first perspective view of an alternative embodiment of a mobile soil sample collection system according to the present disclosure.
Figure 55:
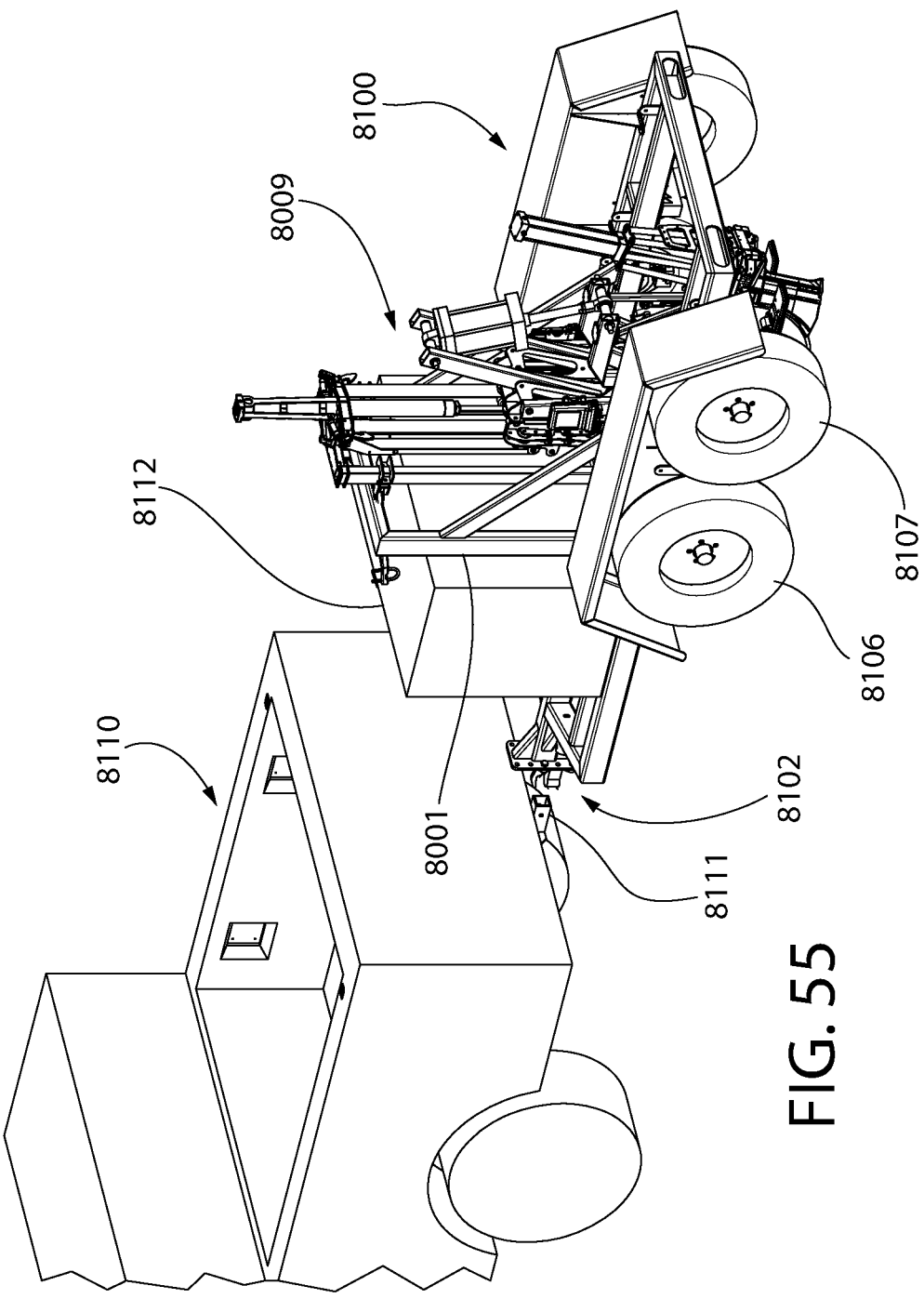
FIG. 55 is a second perspective view thereof.
Figures 56, 57:
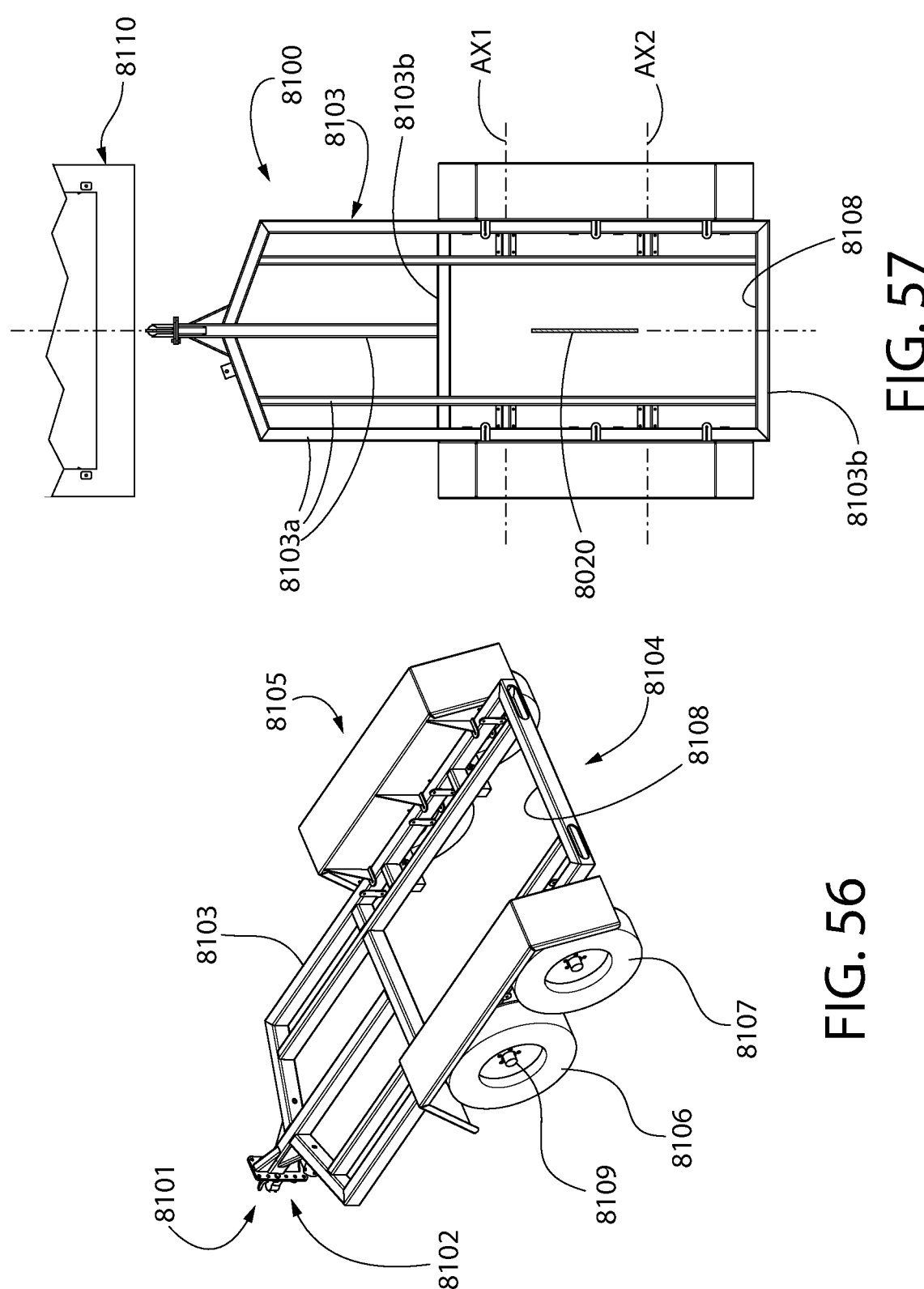
FIG. 56 is a top rear perspective view of the sample collection trailer alone.
FIG. 57 is a top view of the trailer.
Figure 58:
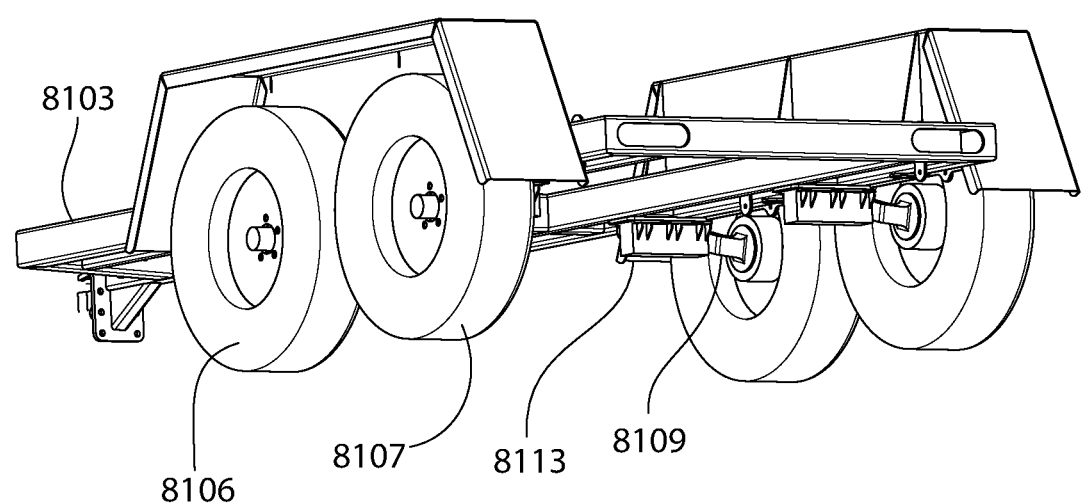
FIG. 58 is a side rear perspective view thereof.

Referring to FIG. 2, the control system 2800 including programmable controller 2820 may be mounted on a translatable self-propelled or pulled sampling vehicle 2802 (e.g., tractor, trailer, combine harvester, etc.). The vehicle 2802 in various embodiments may be an engine-powered sample collection vehicle 8003 (see, e.g., FIG. 3) or a pulled sample collection trailer 8100 (see, e.g., FIG. 54) as further described herein. In other embodiments, the controller may be part of a stationary work station or facility. The sampling vehicle whether vehicle 8003 or trailer 8100 and its boundaries are designated by dashed box in FIG. 2 (those items within the box being mounted onboard the sampling vehicle in the illustrated embodiment).

Control system 2800, whether onboard or off-board the sampling vehicle, generally includes the programmable controller 2820, non-transitory tangible computer or machine accessible and readable medium such as memory 2805, and a network interface 2815. Computer or machine accessible and readable medium may include any suitable volatile memory and non-volatile memory or devices operably and communicably coupled to the processor(s). Any suitable combination and types of volatile or non-volatile memory may be used including as examples, without limitation, random access memory (RAM) and various types thereof, read-only memory (ROM) and various types thereof, hard disks, solid-state drives, flash memory, or other memory and devices which may be written to and/or read by the processor operably connected to the medium. Both the volatile memory and the non-volatile memory may be used for storing the program instructions or software. In one embodiment, the computer or machine accessible and readable non-transitory medium (e.g., memory 2805) contains executable computer program instructions which when executed by the system controller 2820 cause the system to perform operations or methods of the present disclosure including measuring properties and testing of soil and vegetative samples. While the machine accessible and readable non-transitory medium (e.g., memory 2805) is shown in an exemplary embodiment to be a single medium, the term should be taken to include a single medium or multiple media (e.g., a centralized or distributed database, and/or associated caches and servers) that store the one or more sets of control logic or instructions. The term "machine accessible and readable non-transitory medium" shall also be taken to include any medium that is capable of storing, encoding or carrying a set of instructions for execution by the machine and that cause the machine to perform any one or more of the methodologies of the present disclosure. The term "machine accessible and readable non-transitory medium" shall accordingly also be taken to include, but not be limited to, solid-state memories, optical and magnetic media, and carrier wave signals.

Network interface 2815 communicates with the soil or other agricultural material sample processing and analysis systems and devices (collectively represented by box 2803) of sub-systems 3002 and 3003 shown in FIG. 1, and other systems or devices related to collecting, processing, and analyzing soil or other agricultural related materials.

The machine or soil sampling vehicle network 2810 onboard sampling vehicle 2802 (e.g., engine-powered sample collection vehicle 8003 in FIG. 3 or pulled sample collection trailer 8100 in FIG. 54) can include sensors 2812 (e.g., sensors for measuring properties of soil and vegetative samples, speed sensors, etc.), controllers 2811 (e.g., GPS receiver, radar unit) for controlling and monitoring operations of the sampling vehicle and mobile soil sample collection system 8000 comprising the sample collection apparatus 8002. Controller 2820 is configured to control operations of the collection apparatus 8002 via network 2810. The network interface 2815 can be configured for wired and/or wireless bidirectional communications which may include at least one of a GPS transceiver, a WLAN transceiver (e.g., WiFi), an infrared transceiver, a Bluetooth transceiver, Ethernet, Near Field Communications, or other suitable communication interfaces and protocols for communications with the other devices and systems including the sample collection system 8000. The network interface 2815 may be integrated with the control system 2800 as illustrated in FIG. 2, the machine network 2810, or elsewhere. The I/O (input/output) ports 2829 of control system 2800 (e.g., diagnostic/on board diagnostic (OBD) port) enable communication with another data processing system or device (e.g., display devices, sensors, etc.).

The programmable controller 2820 may include one or more microprocessors, processors, a system on a chip (integrated circuit), one or more microcontrollers, or combinations thereof. The processing system includes processing logic 2826 for executing software instructions of one or more programs and a communication module or unit 2828 (e.g., transmitter, transceiver) for transmitting to and receiving communications from the machine network 2810 of sampling machine or vehicle 2802 via direct communication link 2831 or network interface 2815. The communication unit 2828 may be integrated with the control system 2800 (e.g. controller 2820) or be separate from the controller. In one embodiment, the communication unit 2828 may be in operable data communication with the machine/vehicle network 2810 via a diagnostic/OBD port of the I/O ports 2829.

Programmable processing logic 2826 of the control system 2800 which directs the operation of system controller 2820 including one or more processors may process the communications (i.e. data/information) received via the communication unit 2828 or network interface 2815 from the mobile soil sample collection system 8000 and soil sample processing and analysis systems and devices 2803 including without limitation agricultural data (e.g., test data, testing results, GPS data, liquid application data, flow rates, etc.), data associated with the status and operation of the sample collection apparatus 8002 and sample processing/analysis devices 2803 under the control of programmable system controller 2820. The memory 2805 of control system 2800 is configured for preprogrammed variable or setpoint/baseline values, storing collected data, and computer instructions or programs for execution (e.g. software 2806) used to control operation of the controller 2820, which in turn controls operation of sample collection apparatus 8002 and sample processing/analysis devices 2803. The memory 2805 can store, for example, software components such as testing software for analysis of soil and vegetation samples for performing operations of the present disclosure, or any other software application or module, images 2808 (e.g., captured images of crops), alerts, maps, etc. The system 2800 can also include an audio input/output subsystem (not shown) which may include a microphone and a speaker for, for example, receiving and sending voice commands or for user authentication or authorization (e.g., biometrics).

In some embodiments of soil sampling/collection system 8000, sampling vehicle 2802 (e.g., engine-powered sample collection vehicle 8003 or sample collection trailer 8100) can further include a sensing system 2812 comprising a plurality of different sensors. The sensing systems and sensors are in data communication with system controller 2820. Additional data at each point sampled can be tested by the sensing system. Sensing systems can include one or more of the following: spectrographic measurement, electrical conductivity, apparent electrical conductivity, LIDAR, radar, ground penetrating radar, sonar, optical height, camera, time of flight camera. Examples of spectrographic measurement include, but are not limited to, visible light, laser, near-infrared, infrared, transient infrared spectroscopy, RAMAN spectroscopy, ultraviolet, and x-ray. Other sensors which communicate with system controller 2820 may be associated with operation of the sample collection apparatus 8002 and components thereof including various equipment positional or orientation sensors, proximity sensors, etc. The combination of soil and/or other agricultural material sampling along with sensing can provide complete automated control of the sample collection apparatus 8002 for collection of samples and provide more detailed analysis of the conditions in the field.

The system controller 2820 communicates bi-directionally with memory 2805 via communication link 2830, machine or sample collection system network 2810 directly via communication link 2831 and/or alternatively via communication link 2837 associated with network interface 2815, the network interface 2815 via communication link 2832, display device 2830 and optionally a second display device 2825 via communication links 2834, 2835, and I/O ports 2829 via communication links 2836. System controller 2820 further communicates with the soil sample processing and analysis systems and devices 2803 via the wired/wireless communication links 5752 previously described herein via the network interface 2815 and/or directly as shown.

Display devices 2825 and 2830 can provide visual user interfaces for a user or human operator. The operator may be located onboard engine-powered sample collection vehicle 8003 or engine driven vehicle 8110 which pulls the sampling trailer 8100 through the agricultural field AF. The display devices may include display controllers. In one embodiment, the computerized display device 2825 may therefore be a portable tablet device or other processor-based computing device with a touchscreen that acts as an input/output device which displays data (e.g., equipment status and position, test results of soil, test results of vegetation, liquid application data, captured images, localized view map layer, high definition field maps of as-applied liquid application data, as-planted or as-harvested data or other agricultural variables or parameters, yield maps, alerts, etc.) including data generated by an agricultural data analysis software application. The computerized display device 2825 further receives input from the user or operator for controlling sample collection apparatus 8002 and may display an exploded view of a region of a field, monitoring and operational information, etc. for controlling field operations of the collection apparatus and vehicle. The operations may include controlling configuration of the vehicle and sample collection apparatus 8002, reporting of data, control of the machine or implement including sensors and controllers, and storage of the data generated. The display device 2830 in some embodiments may be a display (e.g., display provided by an original equipment manufacturer (OEM)) that displays images and data for a localized view map layer, as-applied liquid application data, as-planted or as-harvested data, yield data, controlling a machine (e.g., planter, tractor, combine, sprayer, etc.), steering the machine, and monitoring the machine or an implement (e.g., planter, combine, sprayer, etc.) that is connected to the machine with sensors and controllers located on the machine or implement.

Knife-Type Soil Sample Collection System

Traditional agricultural soil sample collection for the purposes of nutrient analysis are performed with stationary systems requiring an inefficient investment in time and labor. This includes manual extraction of soil samples for testing. A machine powered non-stationary, or "On The Go," automated sample collection is desirable for faster and less laborious collection.

According to the present automated mobile soil sample collection system disclosed herein, the system includes a collection apparatus comprising a support frame and including one or more rotatable soil collection spools configured to penetrate the soil for sample collection at timed predetermined intervals. Each spool comprises a hollow tubular body with internal collection cavity included in its cross sectional geometry to capture a depth represented slice of soil and retain the sample. Spool rotational actuation may be achieved with various methods including but not limited to electric, pneumatic, or hydraulic power distribution using motors and gear train, linear cylinders, rack and pinion, solenoids, and/or actuators alone or in any combination. For sample collection, spools normally start in the down (i.e. into the soil) and closed position to the soil which precludes entry of soil into the collection cavity. At predetermined intervals, the spools alternate through cycles of rotating 180 degrees about their longitudinal centerline. The collection cavity cycles and changes upon rotation of the collection spool between a concealed condition relative to the soil (soil collection cavity obscured or blocked), an exposed condition (soil sample captured), and back to concealed condition (captured sample retained in spool). The sample collection apparatus may be controlled by a microprocessor-based system controller such as controller 2820 previously described herein or another controller. The support frame with collection apparatus is configured for mounting on a powered vehicle operable to traverse the agricultural field and collect samples "On The Go."

FIGS. 3-53 depict one embodiment and various aspects of a mobile soil sample collection system 8000 according to the present disclosure. The system comprises a collection assembly 8009 having a front 8005, rear 8006, left lateral side 8007, and right lateral side 8008 identified in FIG. 431 for convenience reference in describing the assembly. The assembly 8009 generally includes support frame 8001 and sample collection apparatus 8002 movably mounted to and supported by the frame. Frame 8001 is configured for detachable mounting to the rear portion of any type of mobile pulled trailer/equipment or self-powered engine-operated wheeled sampling vehicle 8003 operable to travel across the agricultural field AF containing soil to dynamically collect samples "On The Go" while the vehicle is moving. This differs from traditional stationary sampling techniques. Vehicle 8003 if self-powered may be driven by a gas or diesel powered, electric, or hybrid type engine as some non-limiting examples. Vehicles 8003 may be used for solely soil sample collection, or may be any type of general purpose self-driven wheeled vehicle or equipment commonly used in the agricultural arts such as pickup or other trucks, tractors, harvesters, etc. The type of powered vehicle or pulled trailer/equipment used does not limit the disclosure. Collection apparatus 8002 is configured to be pulled through the field by vehicle 8003 to collect samples in the embodiment depicted in FIG. 3.

Support frame 8001 may generally comprise a forward-most primary frame section 8001-1 configured for direct or indirect detachably mounting or coupling to the vehicle, a rearward-most collection apparatus frame section 8001-3, and an intermediate rail frame section 8001-2 mounted therebetween which supports a carriage chassis 8058. Primary frame section 8001-1 may comprise a horizontally elongated mounting rod 8001-4 configured for coupling to the vehicle 8003 in one embodiment. Rod 8001-4 may be cylindrical in one embodiment. A plurality of mounting vibration dampers 8004 at the mounting locations to the vehicle accommodate upward/downward movement of the collection apparatus 8002 and reduce vibration as the collection apparatus penetrates and is pulled through the soil by the vehicle 8003. This avoids cracking of the mounts. In one embodiment, springs 8004-1 may be used for the dampers such a pair of dampers with springs: one spring mounted on each opposite end of the rod 8004-1 as shown. Other numbers of dampers and mounting locations may be used.

The intermediate rail frame section 8001-2 of support frame 8000 supports carriage chassis 8058 which comprises vertically movable carriage 8050 used to adjust the vertical position of the collection apparatus 8002 relative to the surface or ground level of the soil and vehicle 8003. Collection apparatus 8002 is movably coupled to and supported by the carriage as further described herein, which in turn is supported by the rail frame section. Rail frame section 8001-2 may include a pair of laterally spaced and elongated vertical support rods 8001-5, which may be rigidly coupled to horizontal mounting rod 8001-4 by a plurality of substantially horizontal angled struts 8001-6. The horizontal struts support the rail frame section 8001-2 and collection apparatus 8002 coupled thereto from vehicle 8003 in a cantilevered manner. Struts 8001-6 may be mounted proximate to the top portions of rods 8001-5 in one non-limiting embodiment. Rail frame section thus remains stationary relative to the primary frame section 8001-1 and vehicle 8003. Rods 8001-5 may have a tubular body with rectangular or square polygonal transverse cross-sectional shape in one embodiment; however, other polygonal and non-polygonal cross-sectional shapes (e.g. circular) may be used. The rods extend in the vertical direction between an upper mounting bracket 8051 and lower mounting bracket 8052. The top and bottom end portions of each rail 8001-5 are fixedly coupled to the brackets in a rigid manner as shown.

Carriage chassis 8058 includes a pair of laterally spaced apart vertical guide rails 8027 rigidly coupled at each end to and supported from upper and lower brackets 8051, 8052 of the support frame intermediate rail frame section 8001-2 via corresponding upper and lower chassis brackets 8058-1, 8058-2 respectively. Rails 8027 are spaced rearward from and parallel to support rods 8001-5. The rails may be cylindrical with circular transverse cross-section in one embodiment to engage the cylindrical rollers 8053 mounted to the carriage 8050, as further described herein.

It bears noting that the various frame sections 8001-1, 8001-2, and 8001-3 and carriage chassis 8058 described above may include a plurality of additional subparts, components, fasteners, brackets, bearings, sleeves, collars, or other elements beyond the primary parts as shown in the figures which may be necessary to perform their intended support and mounting functions. It is well within the ambit of those skilled in the art to provide such minor parts without undue elaboration here.

With continuing reference to FIGS. 3-53, soil sample collection apparatus 8002 may generally include sample collection knife assembly 8020 rotatably supporting and housing at least one collection spool 8040 shown in the present embodiment being described, rotatable coulter blade 8021, spool positioning actuator 8024, knife positioning actuator 8026, rolling carriage 8050 with carriage actuator 8029, and at least one guide ski 8060 configured to slideably engage the ground or soil surface GS. Coulter blade 8021 is mounted forward and proximate to knife assembly 8020 in one embodiment to create a trench or furrow in the soil through which at least an upper portion of the knife assembly subsequently passes as the collection apparatus travels through soil. Samples are collected from within the furrow. The blade initially breaks up and loosens the soil for the knife assembly which follows thereafter. This helps the knife assembly travel through the soil and collect samples more easily as the assembly contains the movable collection spool. The collected samples may comprise the loosened soil or ground.

Figure 3:
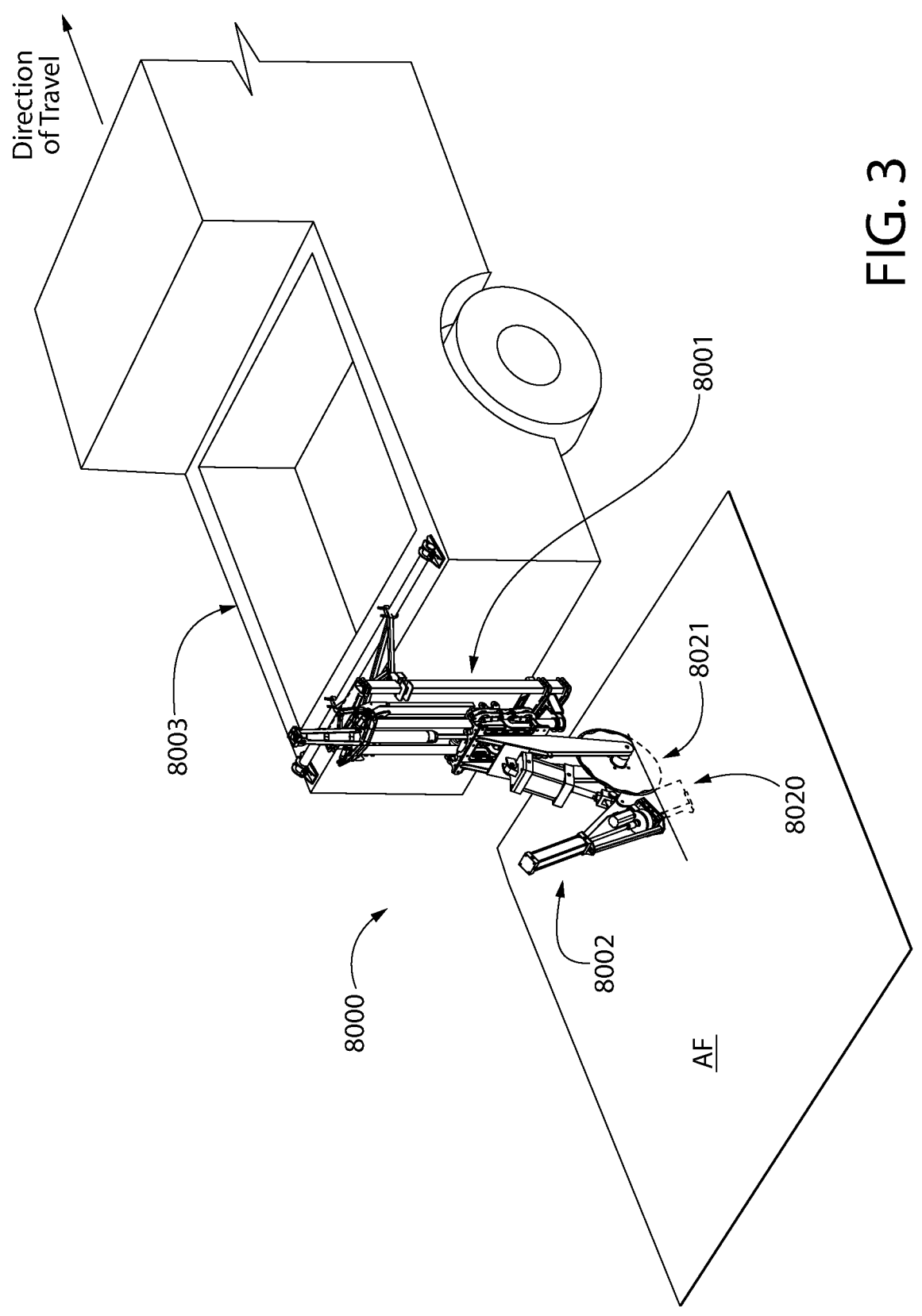
FIG. 3 is a perspective view of one embodiment of a mobile soil sample collection system according to the present disclosure.
Figure 4:
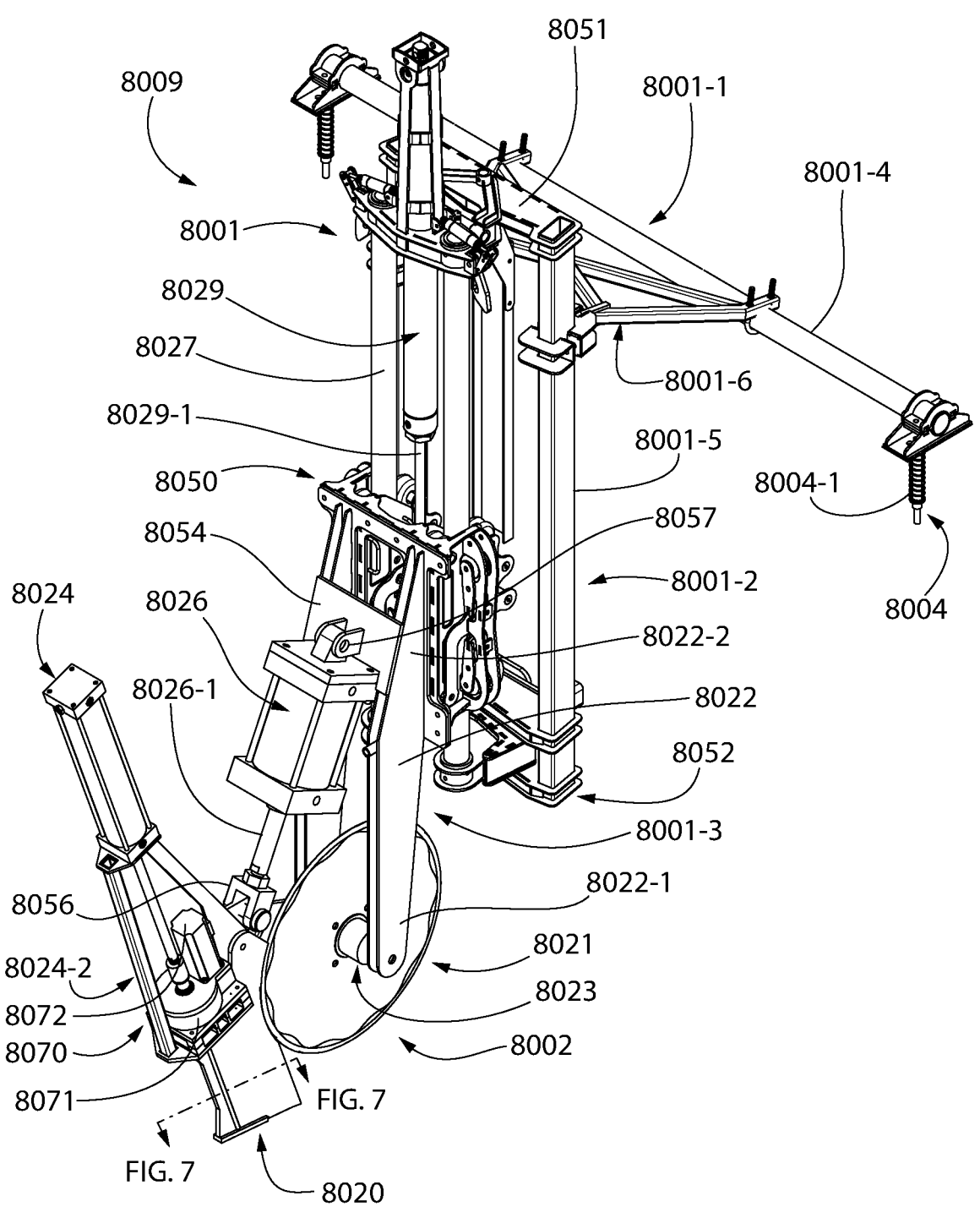
FIG. 4 is a rear top perspective view of a collection assembly comprising a collection apparatus thereof.
Figure 5:
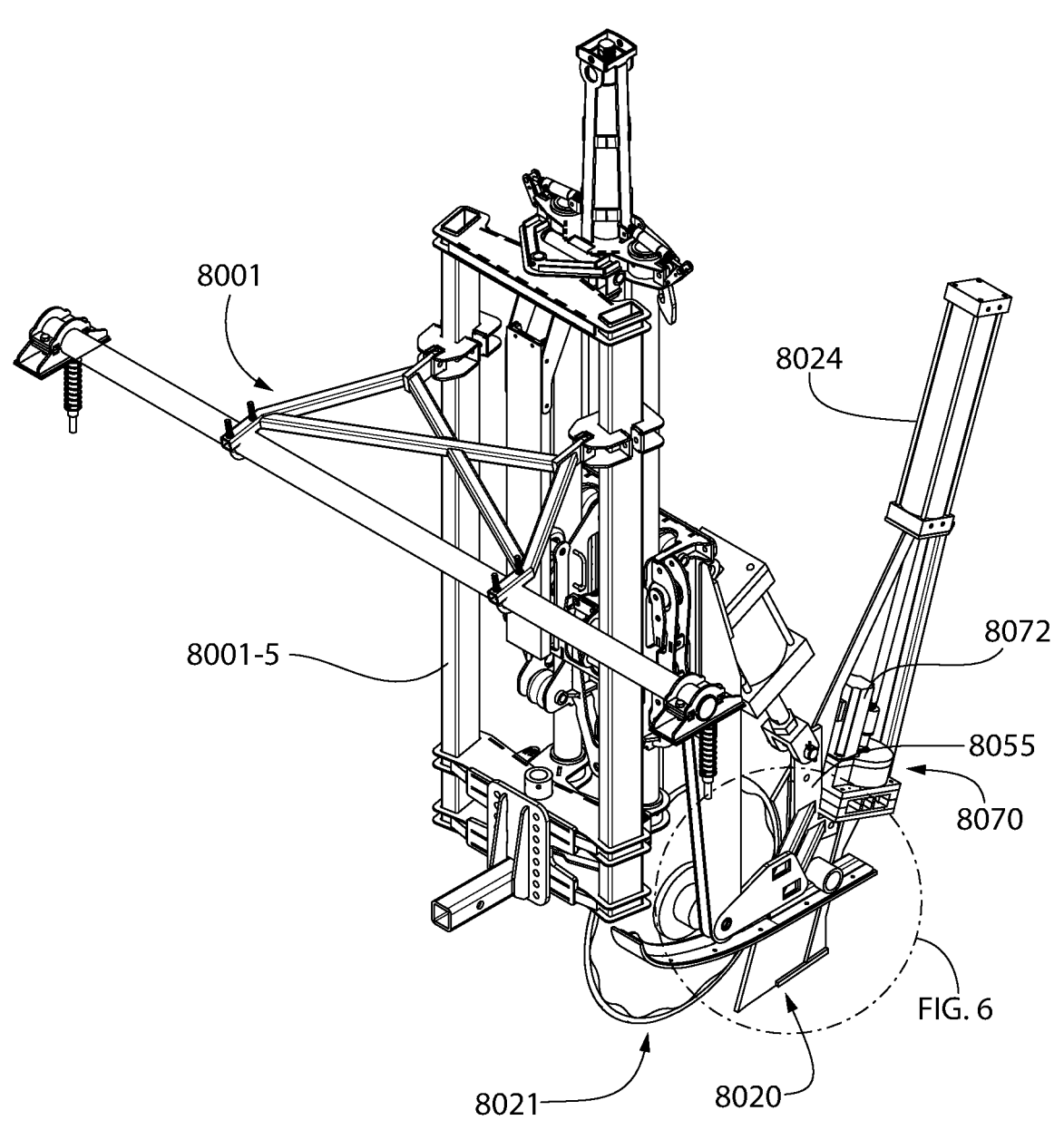
FIG. 5 is a front top perspective view thereof.
Figure 26:
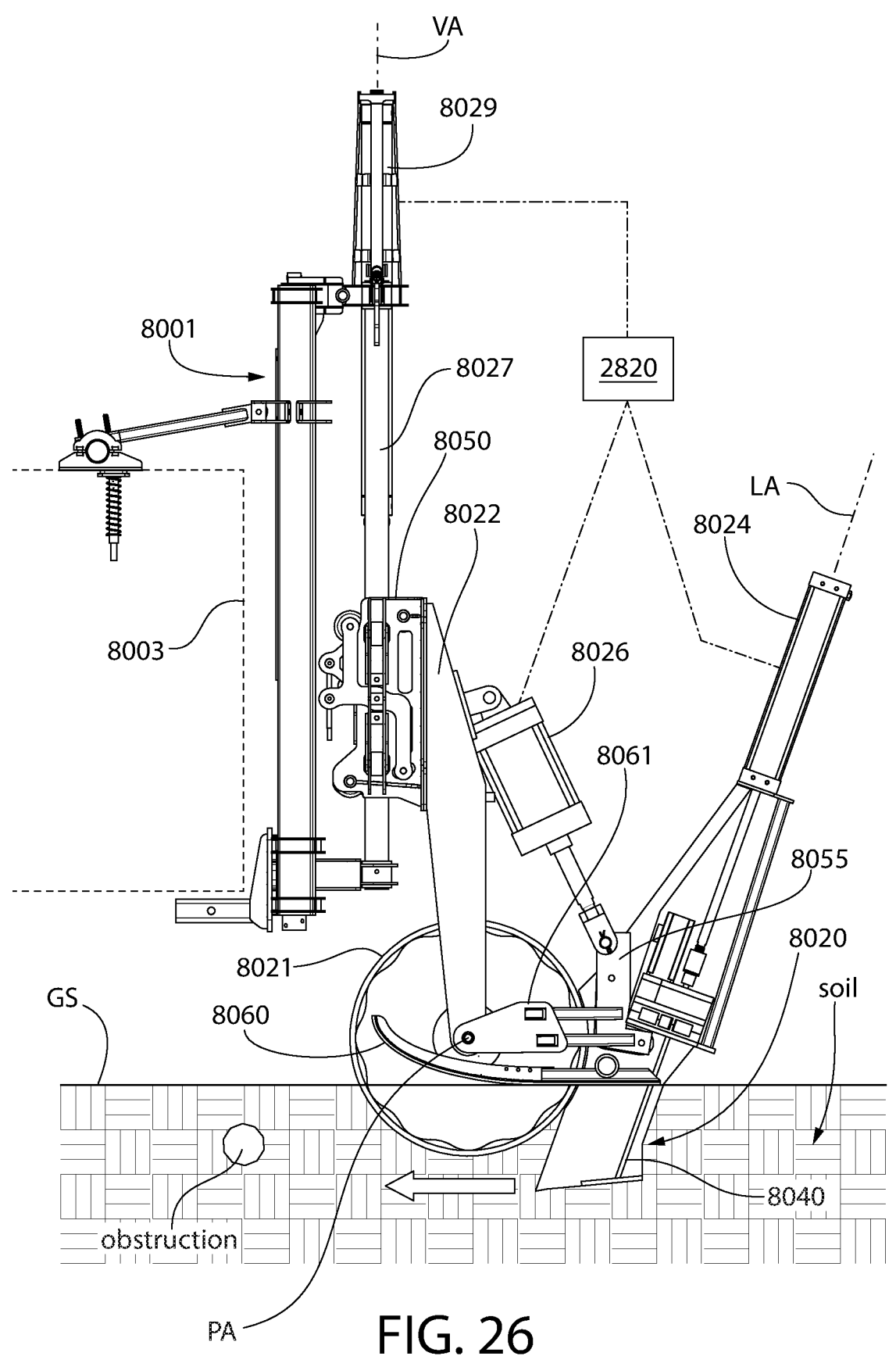
FIG. 26 is a first side view of the collection apparatus in an active lower soil sample collection position engage with the soil with the collection apparatus in a first angular rotated position.
Figure 27:
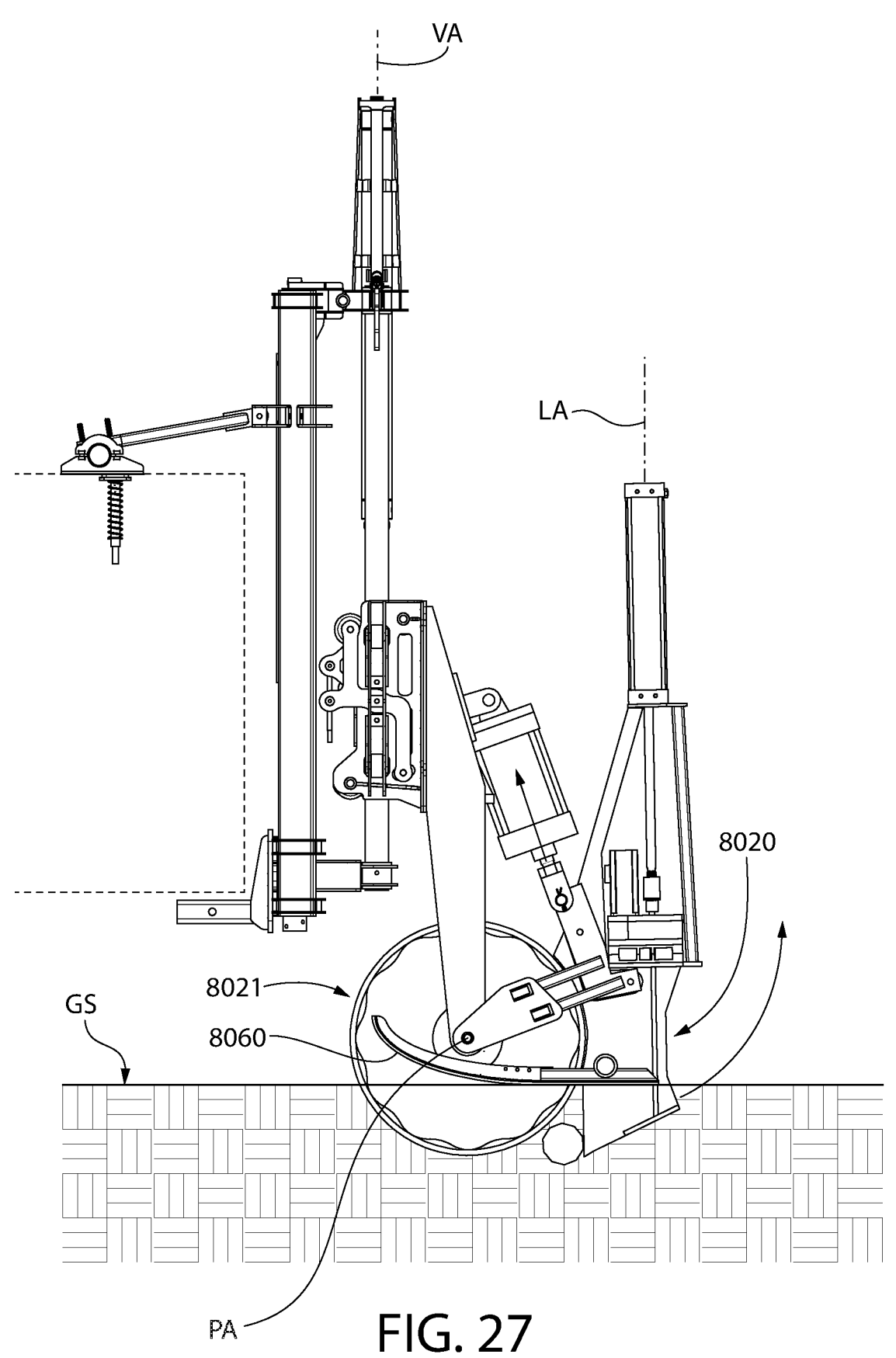
FIG. 27 is a second side view thereof with the collection apparatus in a second angular rotated position.
Figure 28:
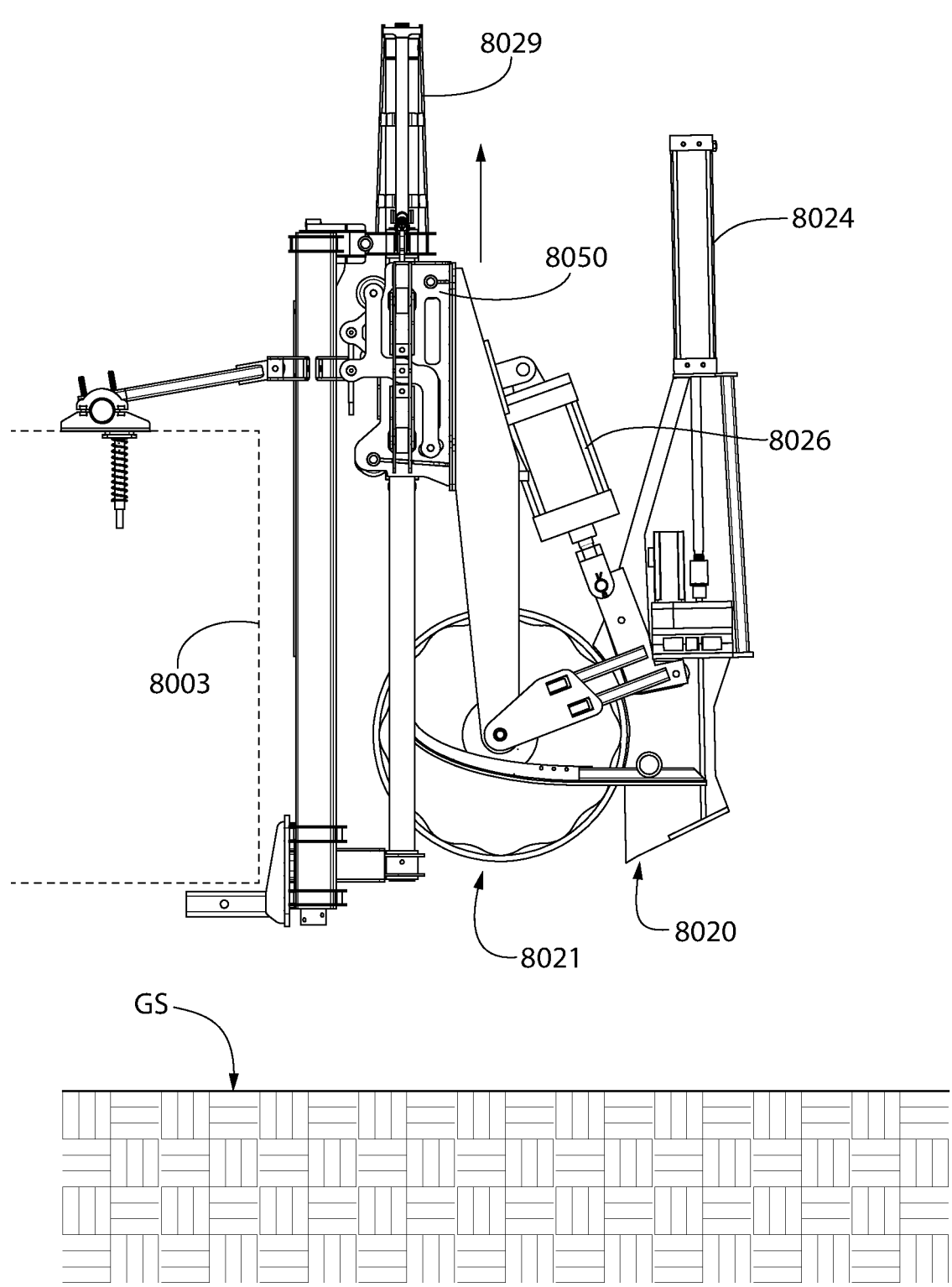
FIG. 28 is a side view of the collection apparatus in an upper stowed position.
Figures 29, 30:
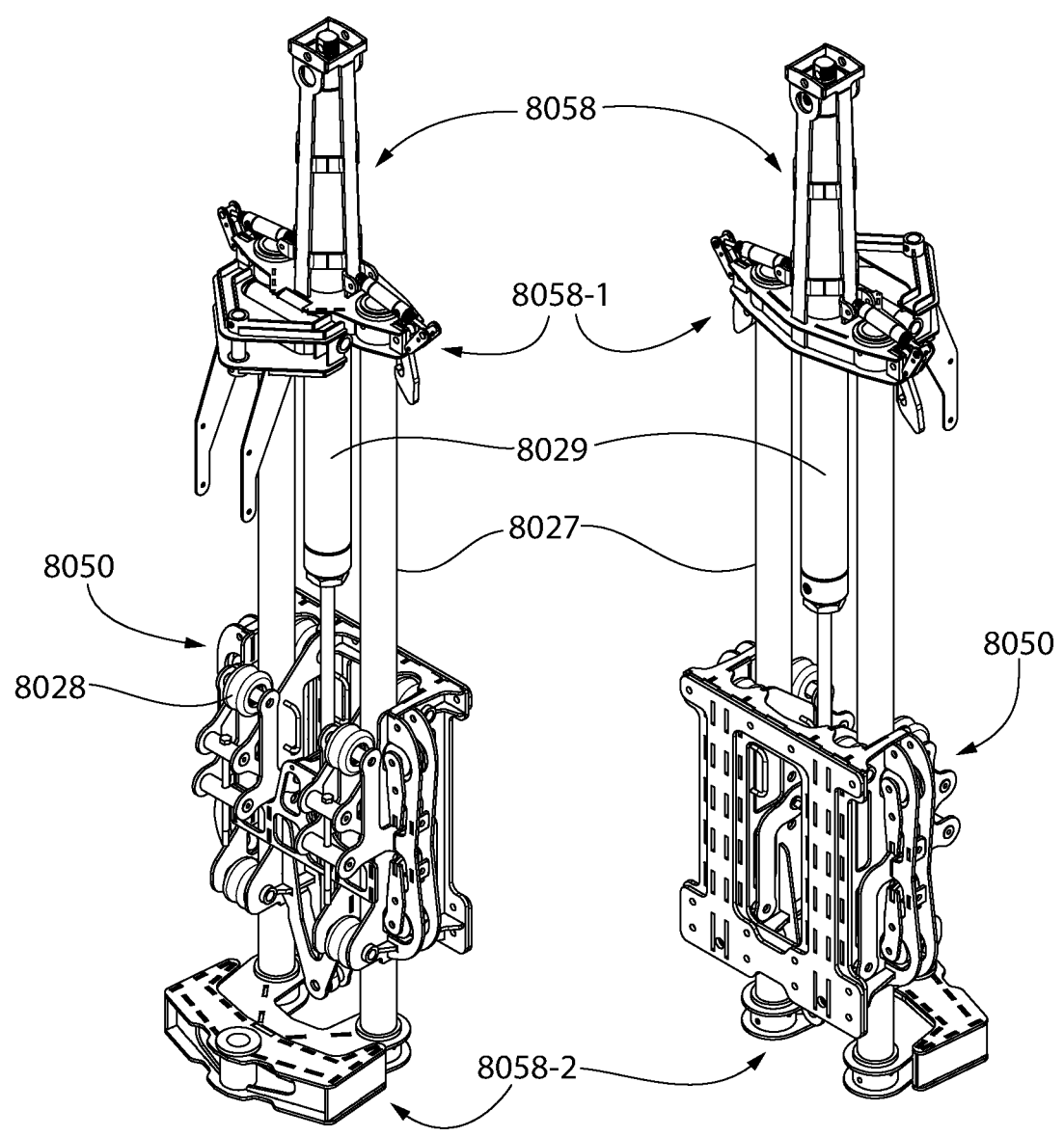
FIG. 29 is a front perspective view of a carriage chassis of the collection assembly supporting a rolling carriage to which the collection apparatus is mounted.
FIG. 30 is a rear perspective view thereof.
Figures 31, 32:
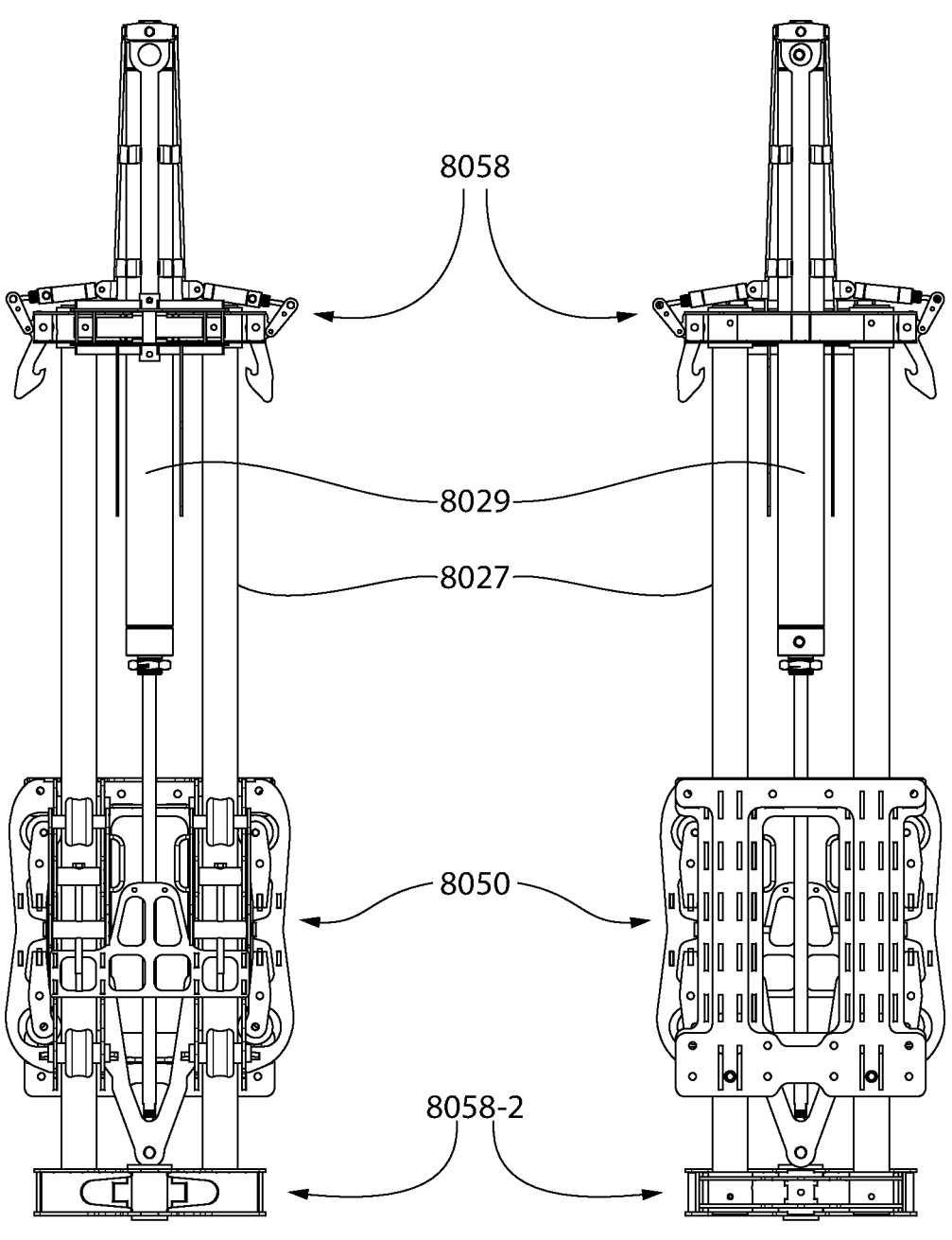
FIG. 31 is a front view thereof.
FIG. 32 is a rear view thereof.
Figures 33, 34, 35:
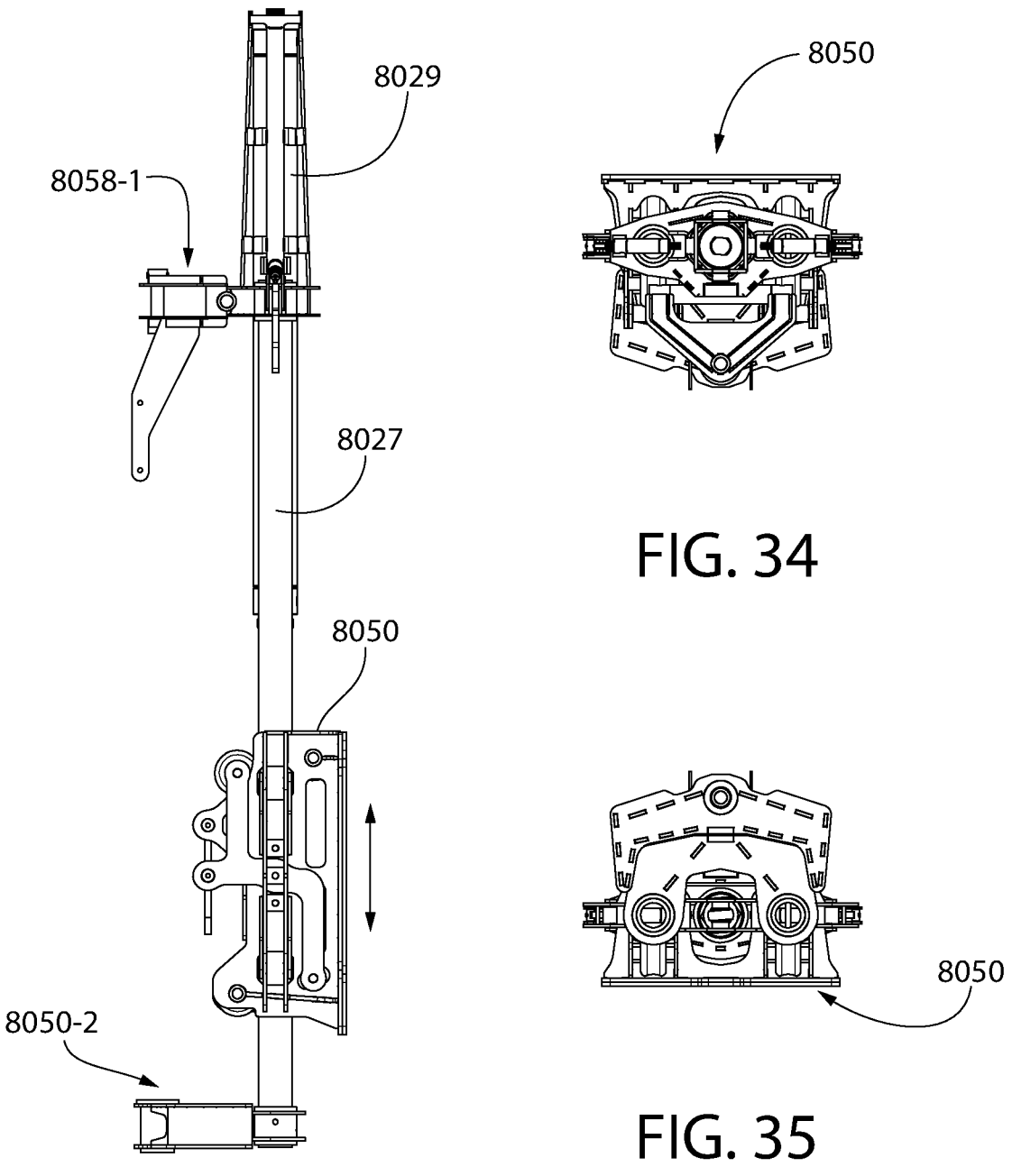
FIG. 33 is right side view thereof.
FIG. 34 is a top view thereof.
FIG. 35 is a bottom view thereof.
Figure 36:
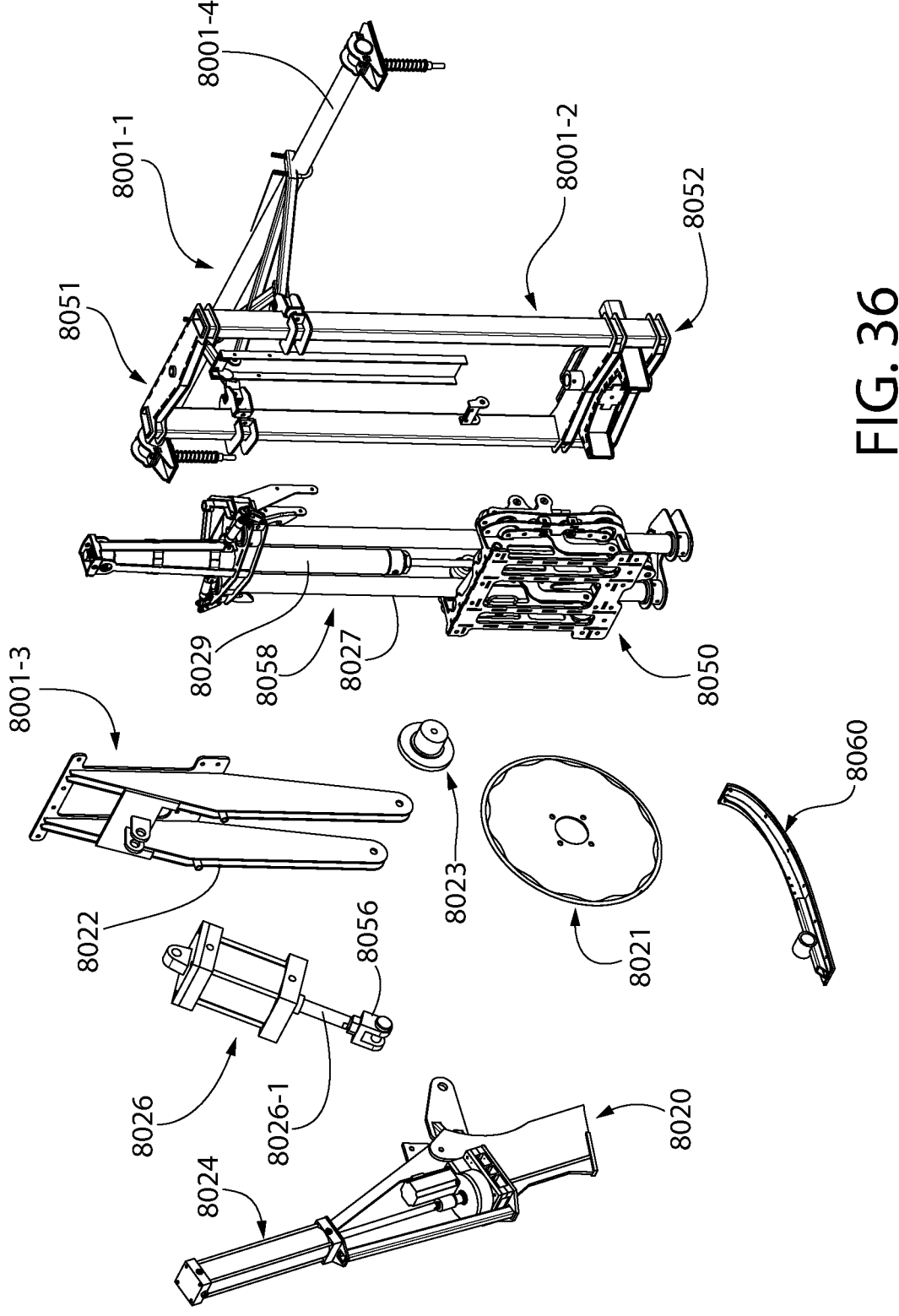
FIG. 36 is a rear exploded view thereof.
Figure 37:
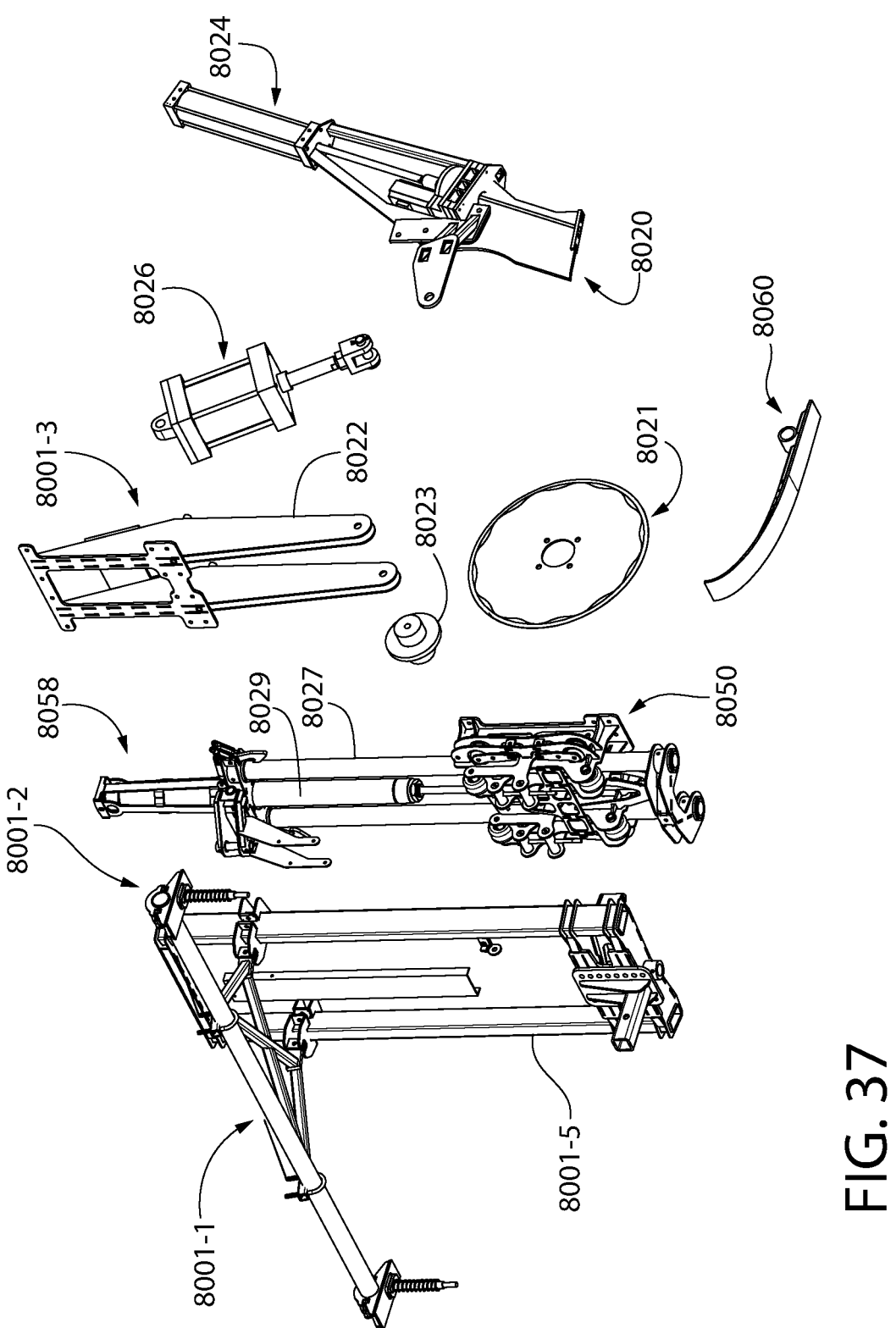
FIG. 37 is a front exploded view thereof.

Knife assembly 8020 and coulter blade 8021, which constitute the soil engaging elements of soil sample collection apparatus 8002, are substantially axially aligned with each other in the direction of travel along horizontal axis HA as best seen in FIG. 3 to accomplish this. The term "substantially" as used here connotes that the knife assembly may be slightly offset laterally from the coulter blade along the horizontal axis HA but functionally will still travel in and benefit from the furrow created by the blade. As shown in FIGS. 3 and 26-27, the knife assembly 8020 and coulter blade 8021 partially penetrate the surface of the soil to a preselected depth for collecting the soil sample.

Coulter blade 8021 may be formed of a generally circular metallic plate in shape and may have a sharpened (i.e. taper or wedge shape) peripheral cutting edge 8151 extending circumferentially around the blade body to better cut through the soil. In some embodiments, the blade may have a scalloped design as shown, or may be plain in other implementations. The coulter blade 8021 is rotatably coupled at its center to hub 8023 by a pair of support arms 8022 laterally spaced apart on opposite sides of the blade. Arms 8022 may be vertically elongated each having a bottom end 8022-1 coupled to one side of the hub in a manner which allows the blade 8021 to rotate, and a top end 8022-2 fixedly coupled to the body of the carriage 8050.

Figure 38:
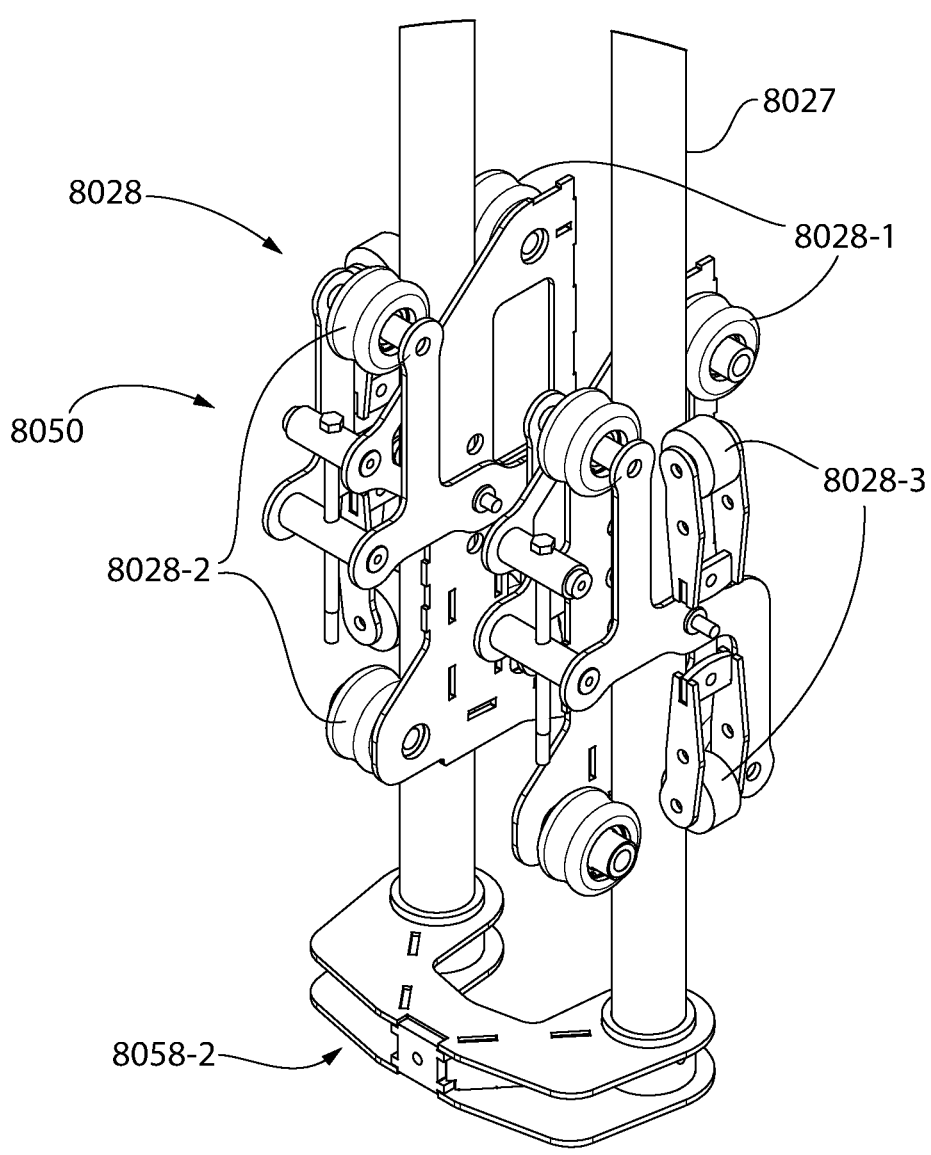
FIG. 38 is a rear perspective view of the carriage with wheels or rollers and guide rails with the outer carriage frame removed for clarity.
Figure 39:
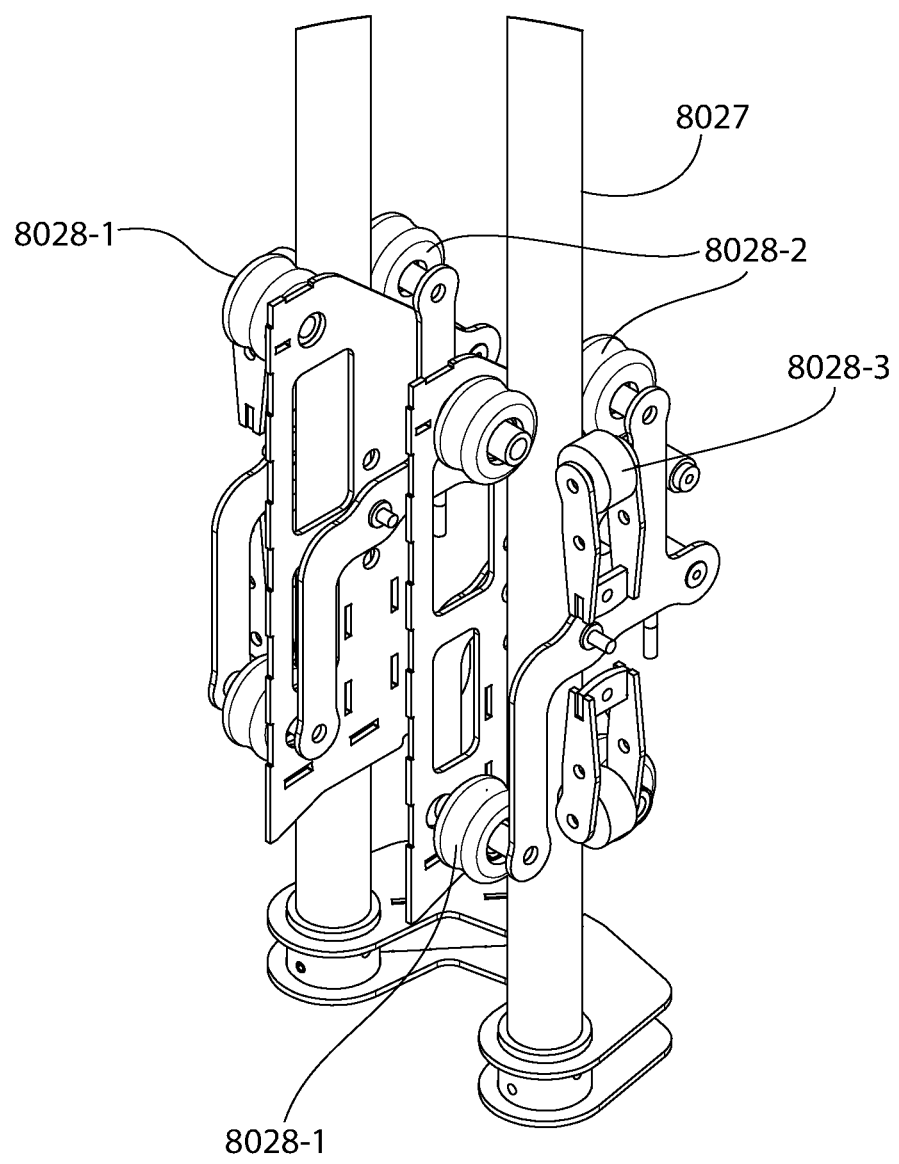
FIG. 39 is a front perspective view thereof.
Figures 40, 41:
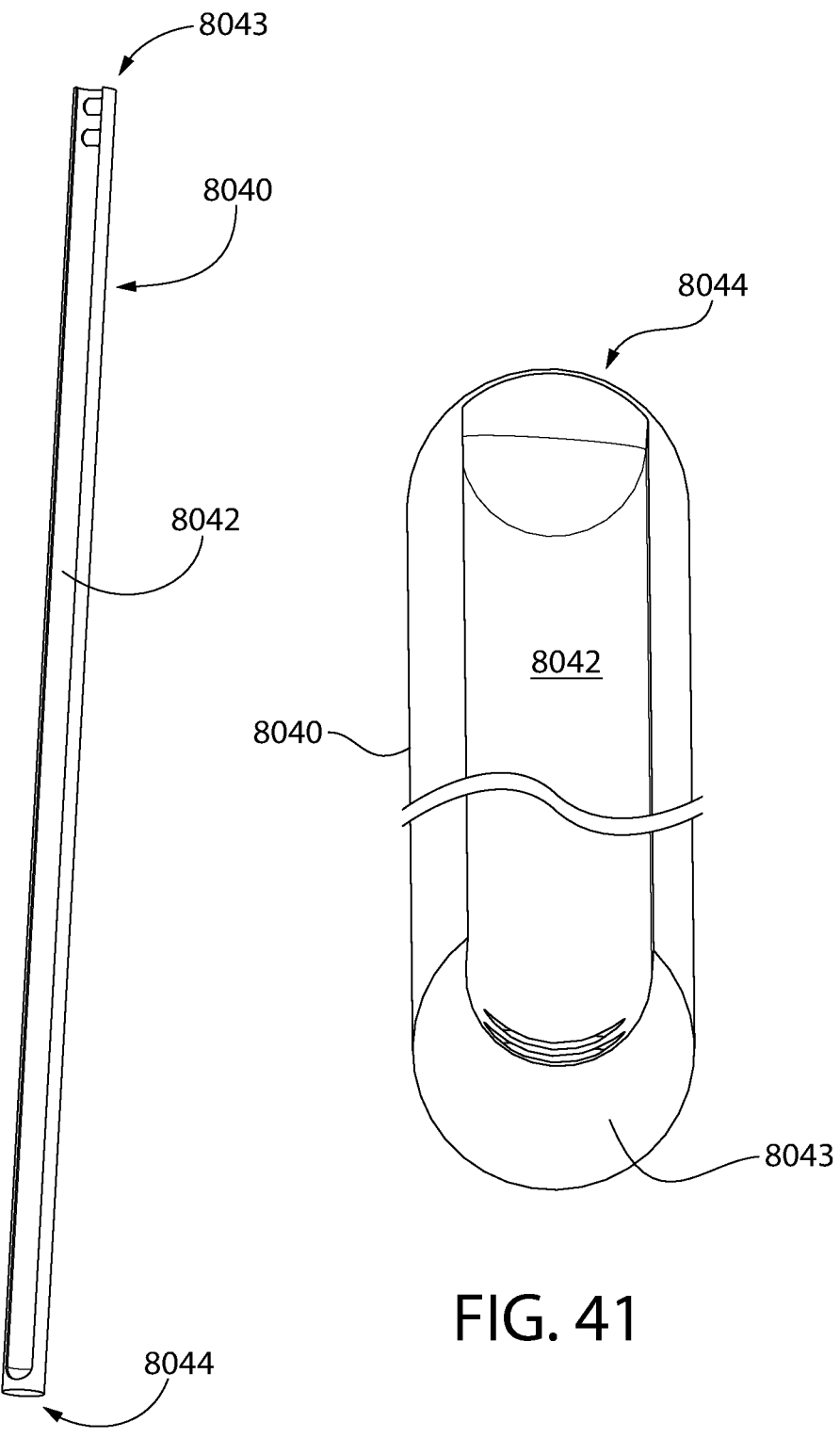
FIG. 40 is a perspective view of the collection spool of the collection apparatus.
FIG. 41 is an enlarged perspective view thereof.
Figure 42:
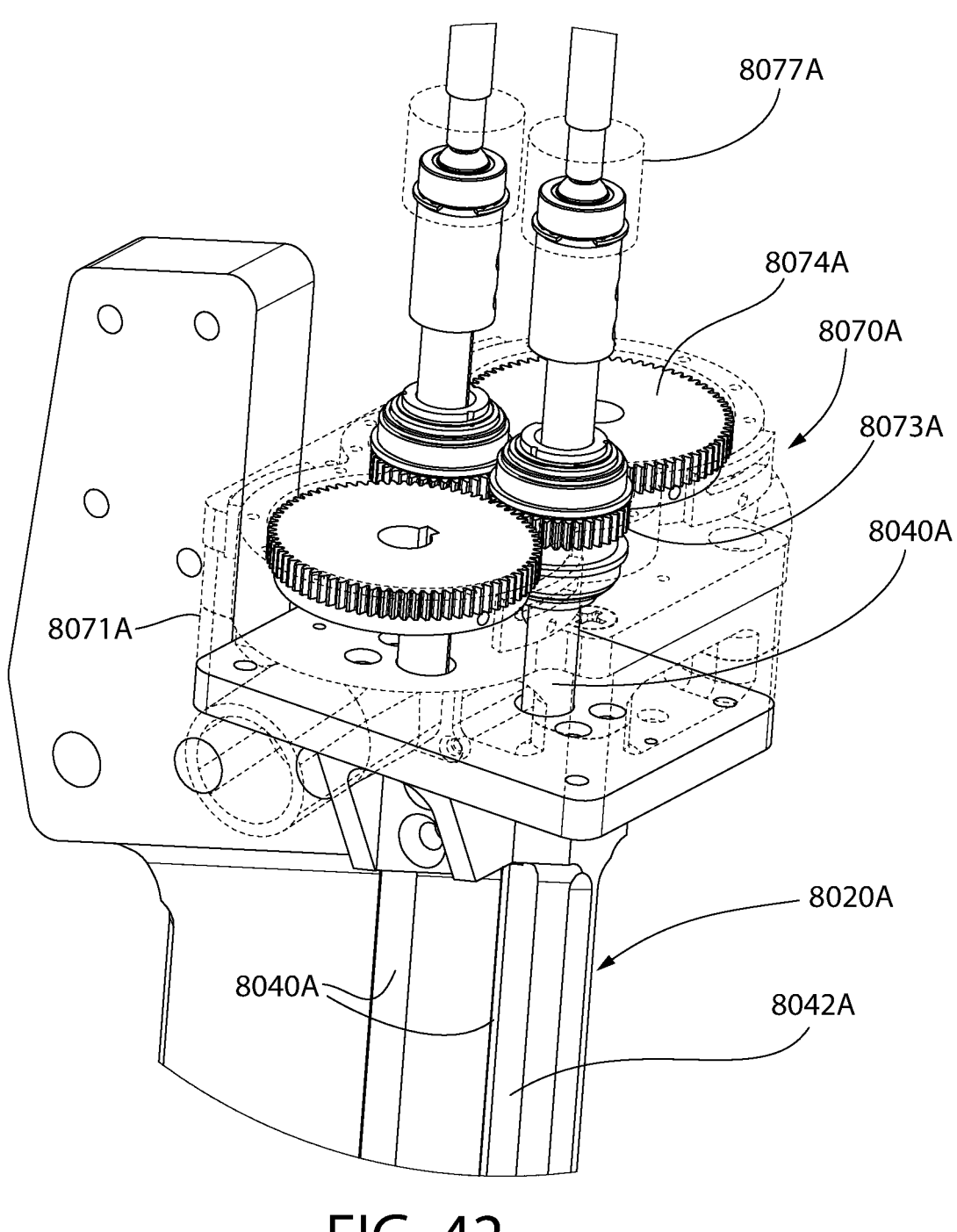
FIG. 42 is a rear perspective view of an alternative two spool embodiment of a collection apparatus showing the gear drive of the spool drive mechanism.
Figure 43:
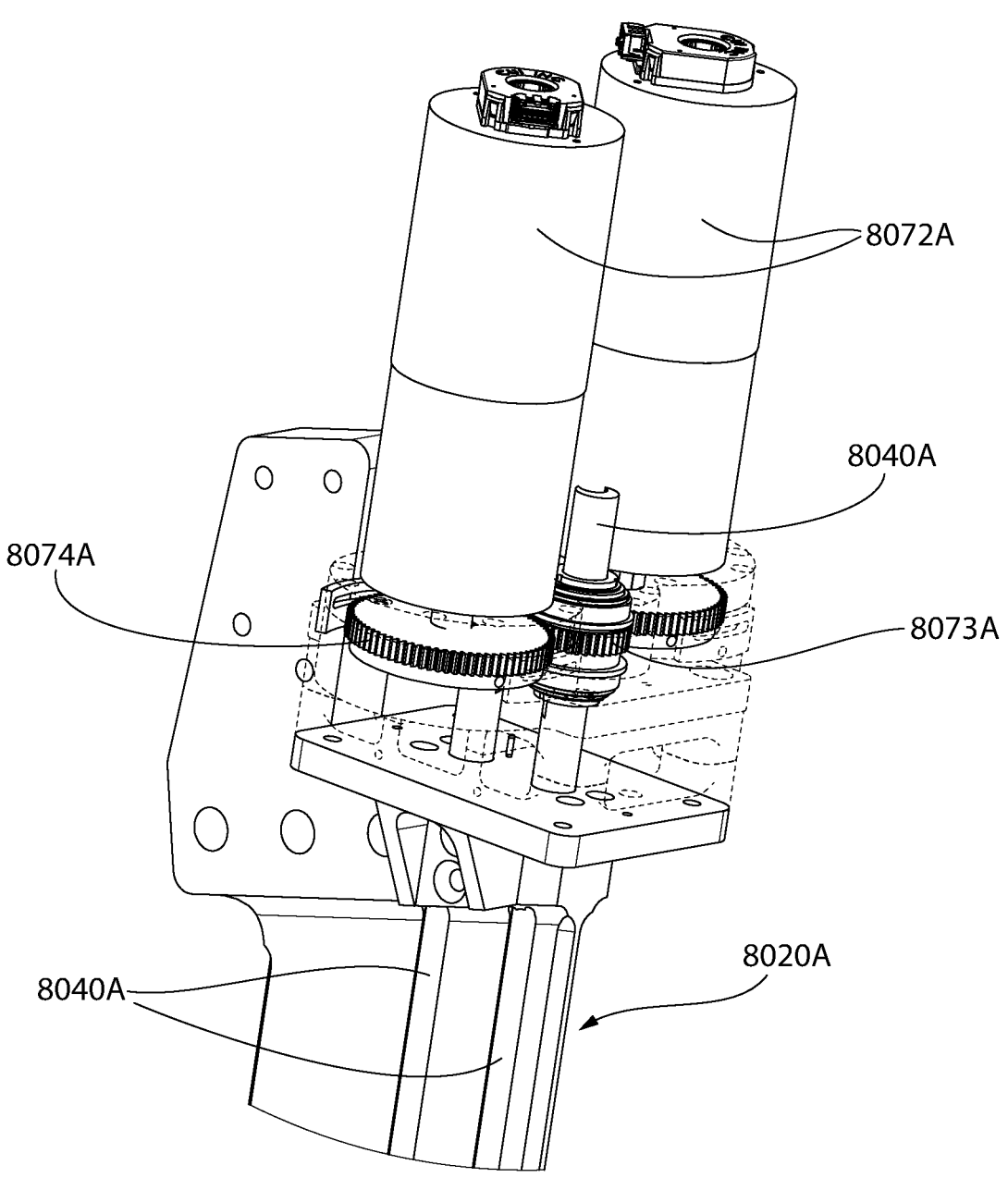
FIG. 43 is a rear perspective view thereof with the gear drive motors mounted.
Figure 44:
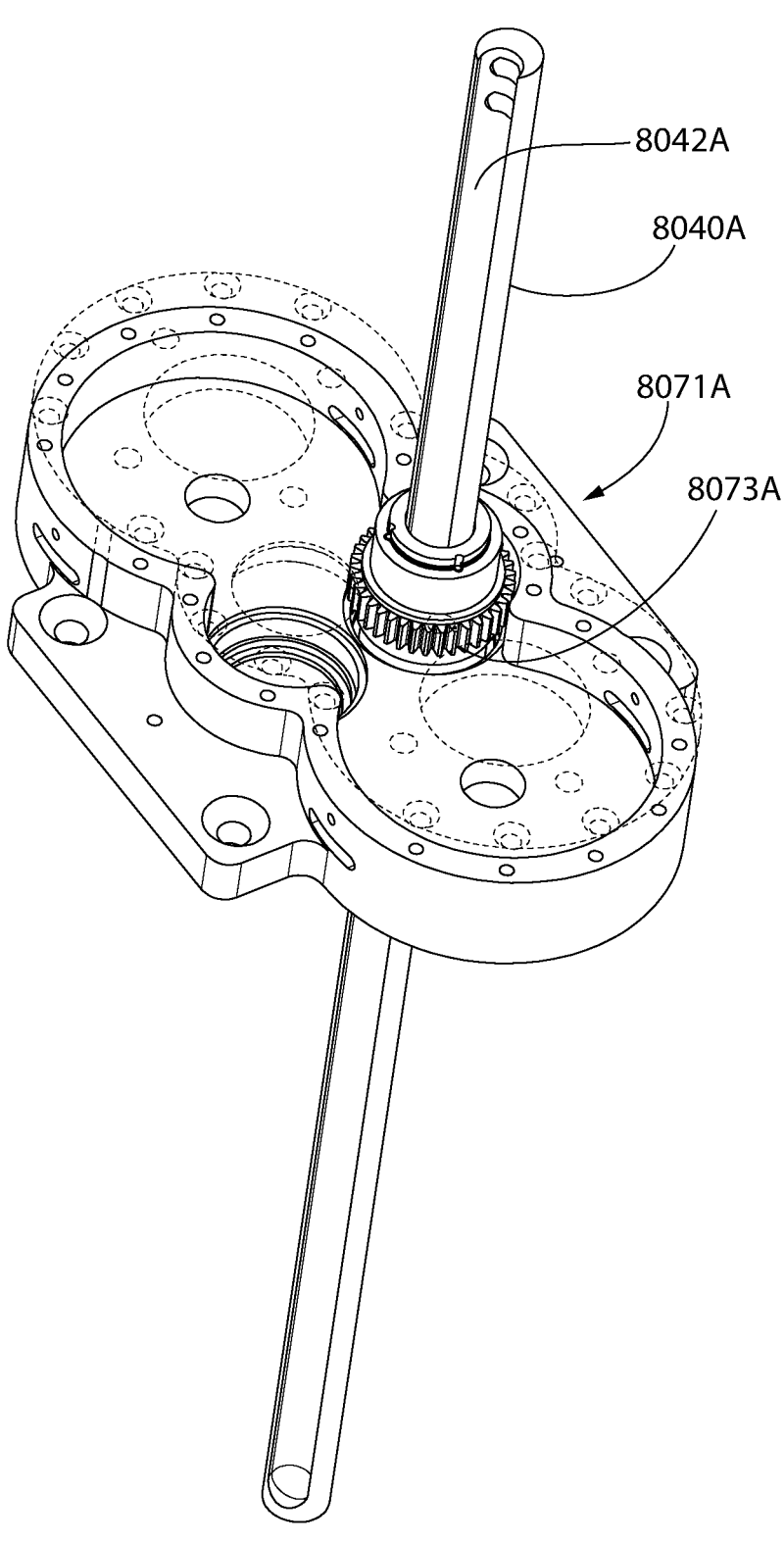
FIG. 44 is a top perspective view of a portion of the gear box and one of the driven gears and collection spool.
Figure 45:
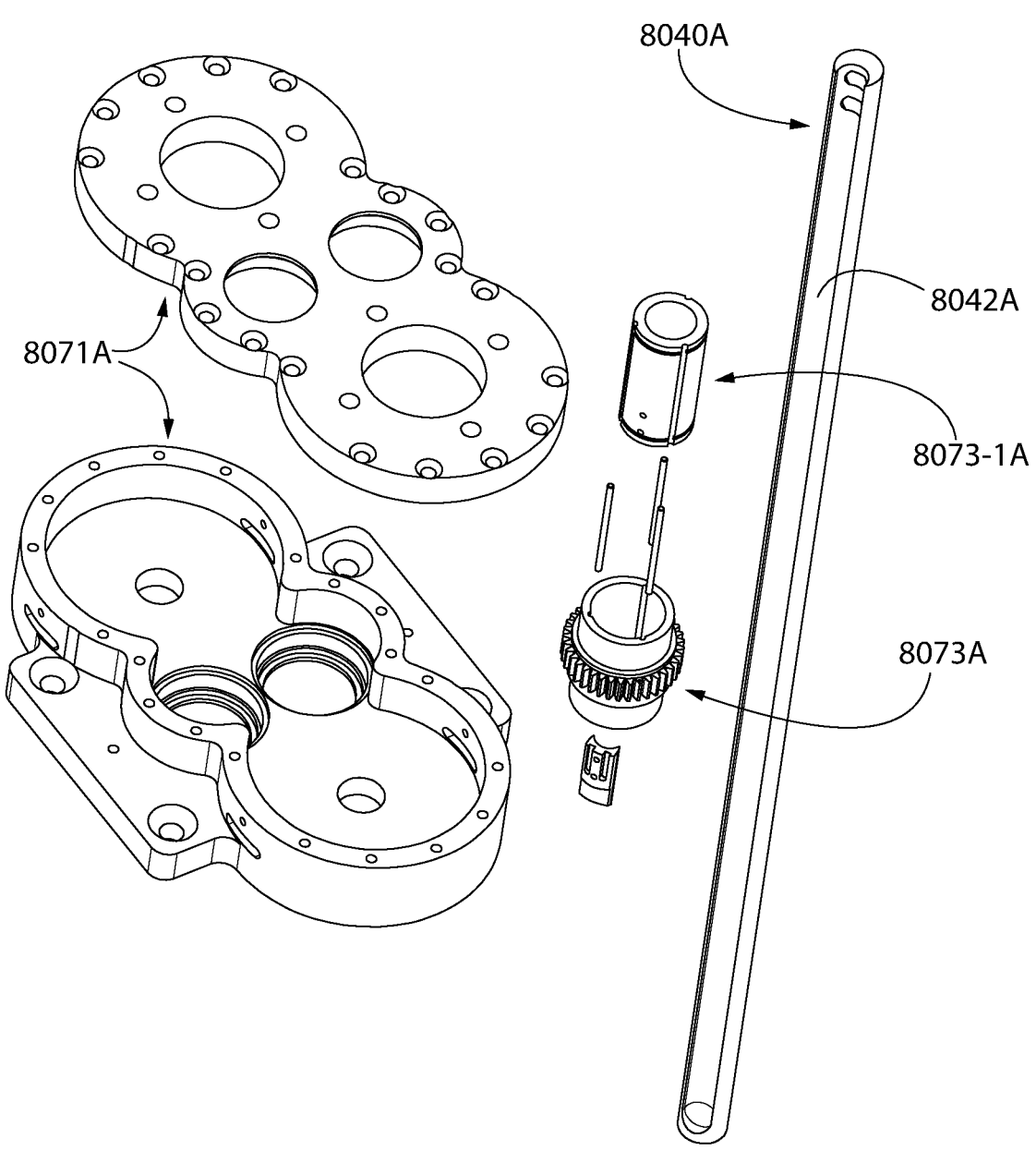
FIG. 45 is an exploded perspective view thereof.
Figures 46, 47:
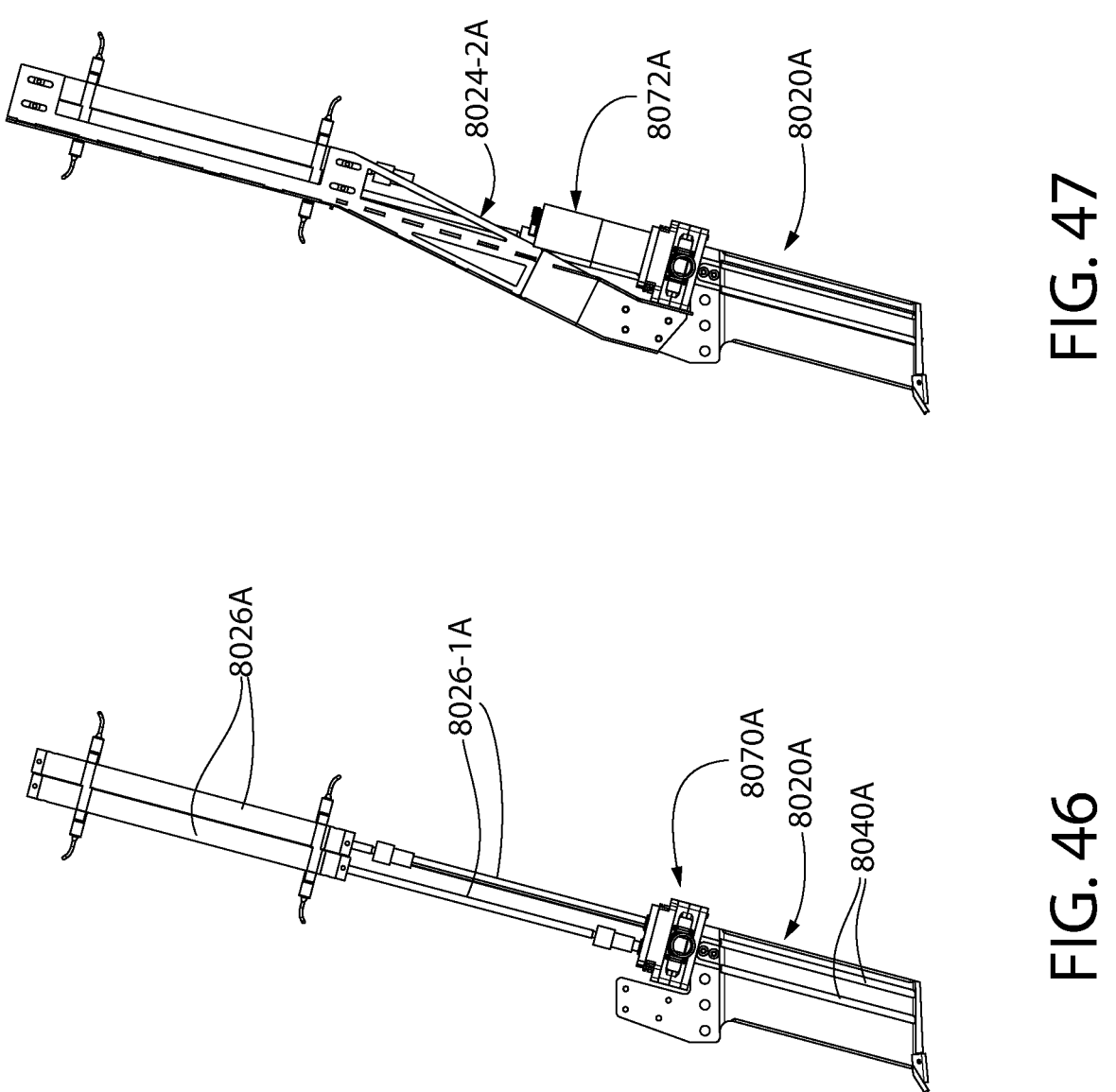
FIG. 46 is a left side view of the knife assembly of the collection apparatus showing the spool drive mechanism with spool positioning actuator support frame removed.
FIG. 47 is a left side view thereof with support frame.
Figures 48, 49:
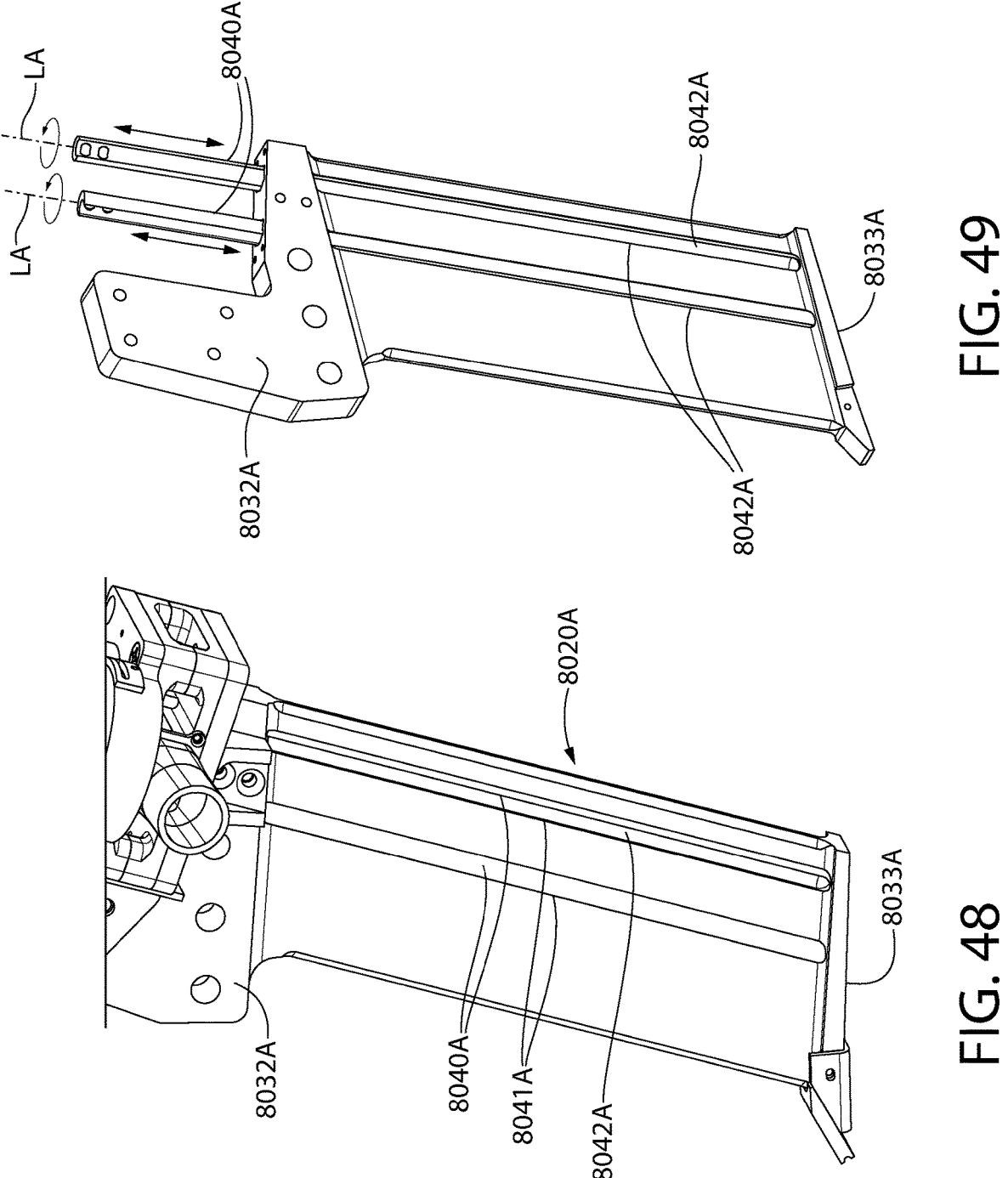
FIG. 48 is a first left side perspective view of the knife assembly.
FIG. 49 is a second left side perspective view thereof.
Figure 50:
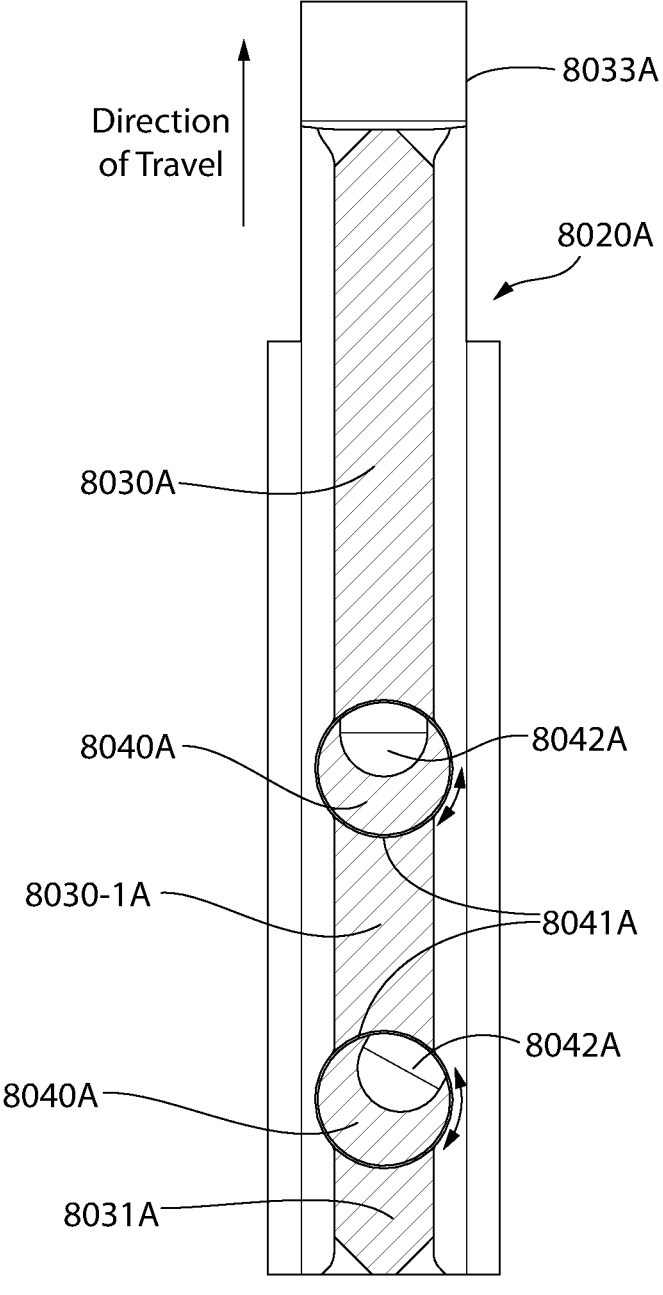
FIG. 50 is a horizontal transverse cross-sectional view of the two spool knife assembly.
Figure 51:
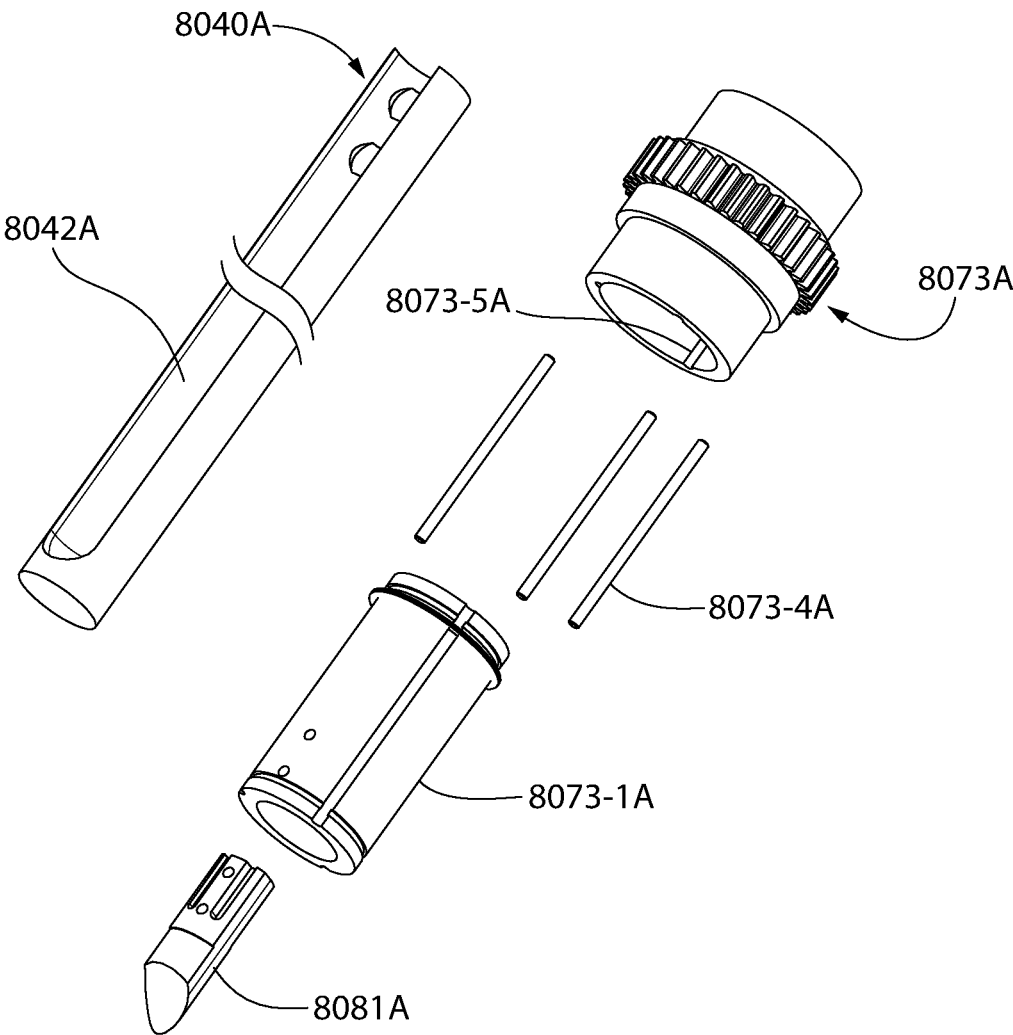
FIG. 51 is an exploded perspective view of the driven gear assembly.
Figure 52:
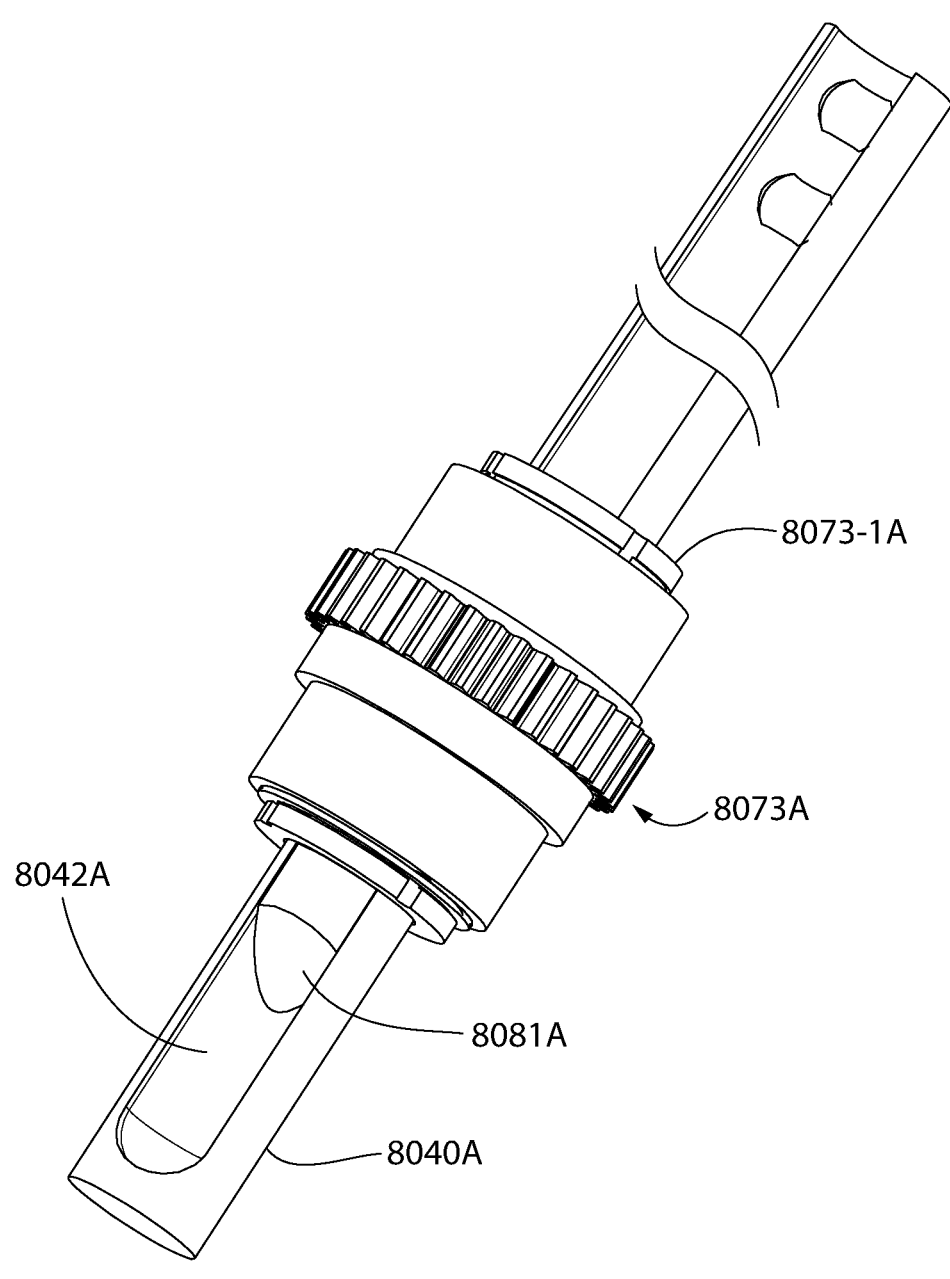
FIG. 52 is an assembled view thereof.

Carriage 8050 includes a plurality of rollers 8028 configured to rollingly engage and move up and down along the guide rails 8027 (best seen in FIGS. 38-39). The rollers may each have an arcuate concave rails engagement surface which is complementary configured to the circular cross-sectional shape of the guide rails to maintain positive mutual engagement while the carriage travels up and down on the rails. To maintain smooth rolling engagement between the rollers and guide rails, in one embodiment, each of the rails may be engaged by vertically spaced pairs of front rollers 8028-1, rear rollers 8028-2, and outboard side rollers 8028-3. The front and rear rollers stabilize movement of the carriage on the rails in the front to rear direction. The outboard rollers stabilize movement of the carriage in the lateral side to side direction. It bears noting that the set of rollers 8028 on carriage 8050 further serve to ameliorate front to rear and side to side forces which may be imparted to the collection apparatus 8002 supported by the carriage when the apparatus encounters rough and undulating soils conditions or rocks at the soil surface GS; neither of which are unexpected in agricultural fields.

The vertical position of the carriage 8050 on guide rails 8027 is controlled by linear-acting carriage actuator 8029. Actuator 8029 is vertically oriented and may be arranged at the vertical geometric centerline between the guide rails as shown. Actuator 8029 operates to lower or raise the carriage relative to the vehicle 8003 and in turn soil surface GS of the soil (see, e.g. FIGS. 24-26). Accordingly, the depth of penetration of the knife assembly 4020 and coulter blade 4021 of collection apparatus 4002 into the soil is primarily adjusted by carriage actuator 8029 to which the collection apparatus is mounted in a cantilevered manner. Actuator 8029 may be a pneumatic cylinder type actuator in one embodiment; however, hydraulic cylinders or electric linear actuators may also be used. The actuator 8029 is fixedly mounted to rail frame section 8001-2 at top and at bottom is operably coupled to the rolling carriage 8050 via operating or piston rod 8029-1. By retracting or extending the piston rod, the actuator 8029 selectively raises or lowers the carriage 8050 to which the entire collection apparatus 8002 is mounted and supported relative to the vehicle 8003 and soil surface. Actuator 8029 may raise the carriage 8050 and collection apparatus 8002 mounted thereto to an upper stowed position for transport when not collecting soil samples (see, e.g. FIG. 28). In a lower active position actively engaged with the soil (see, e.g. FIGS. 26-27), the collection apparatus is ready to collect soil samples.

Figure 12:
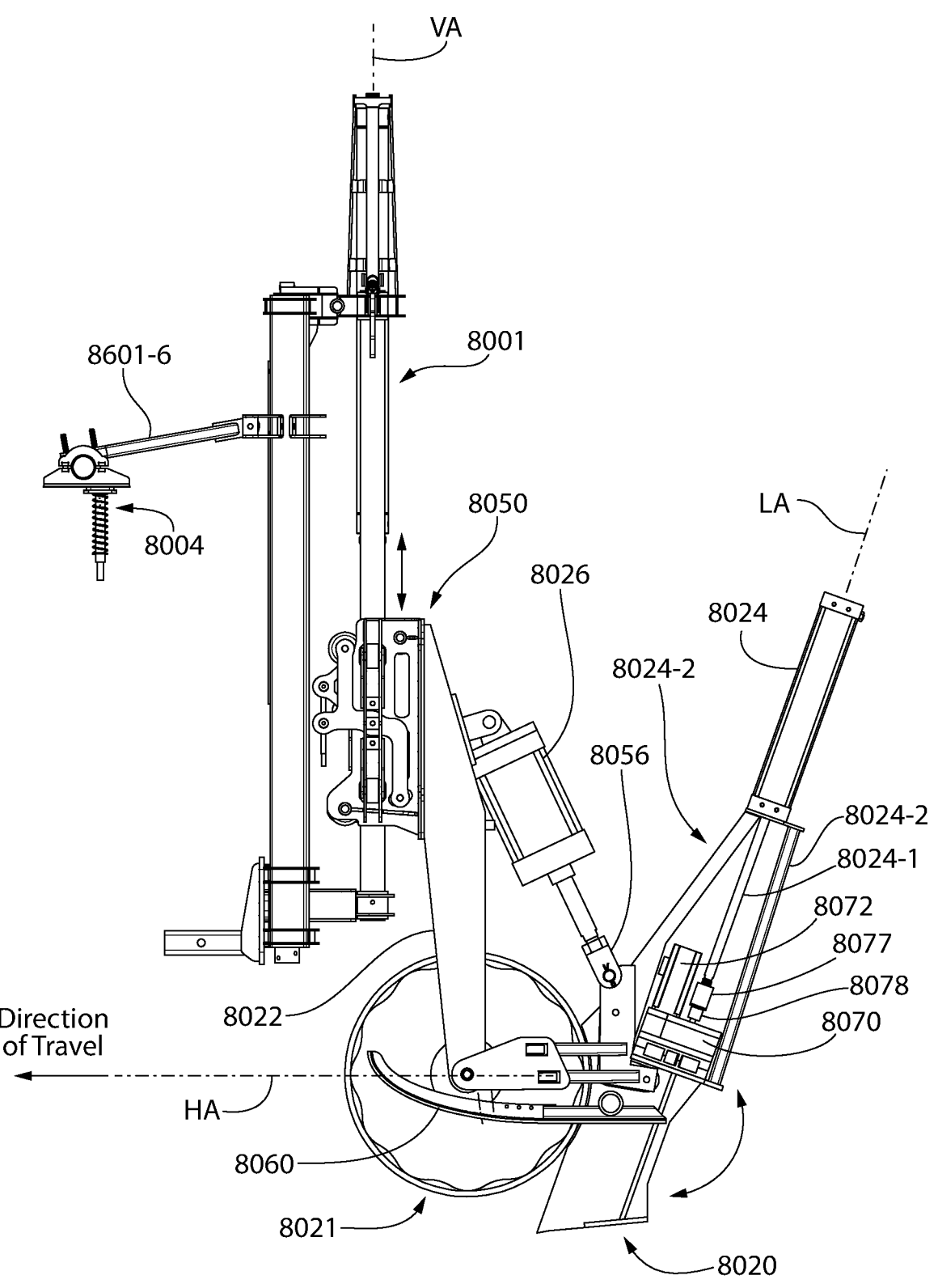
FIG. 12 is a left side view thereof.
Figure 13:
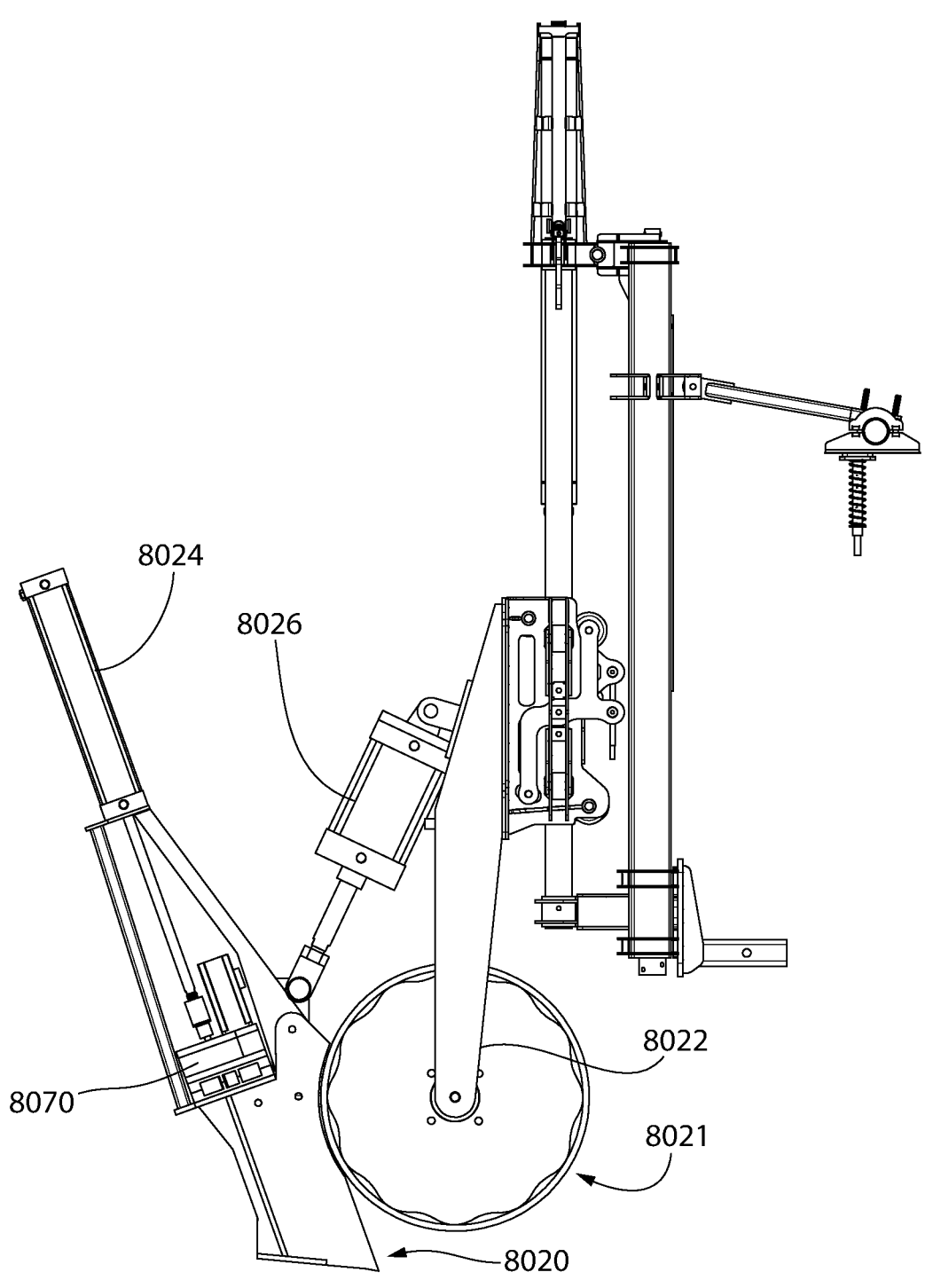
FIG. 13 is a right side view thereof.
Figure 14:
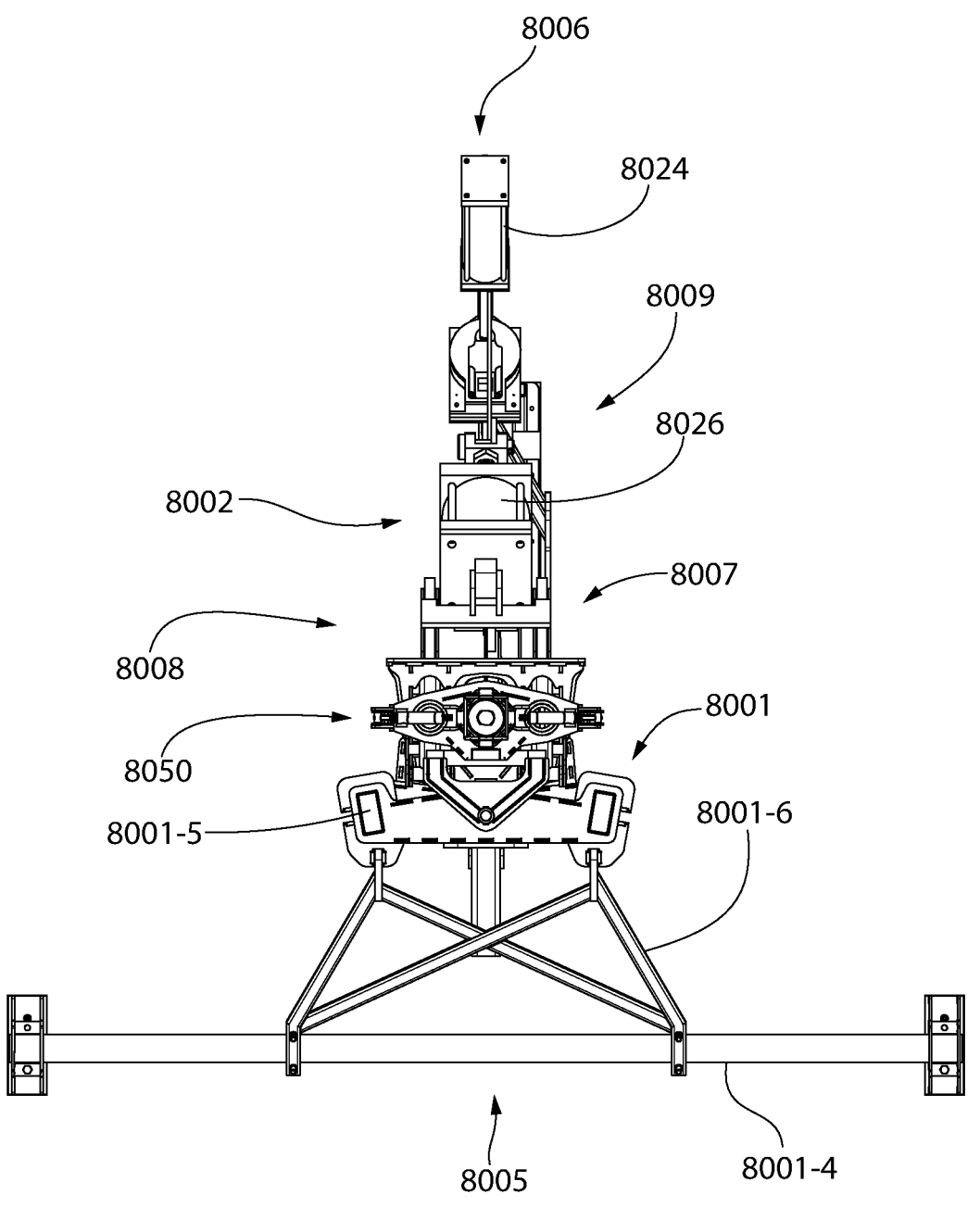
FIG. 14 is a top view thereof.
Figure 15:
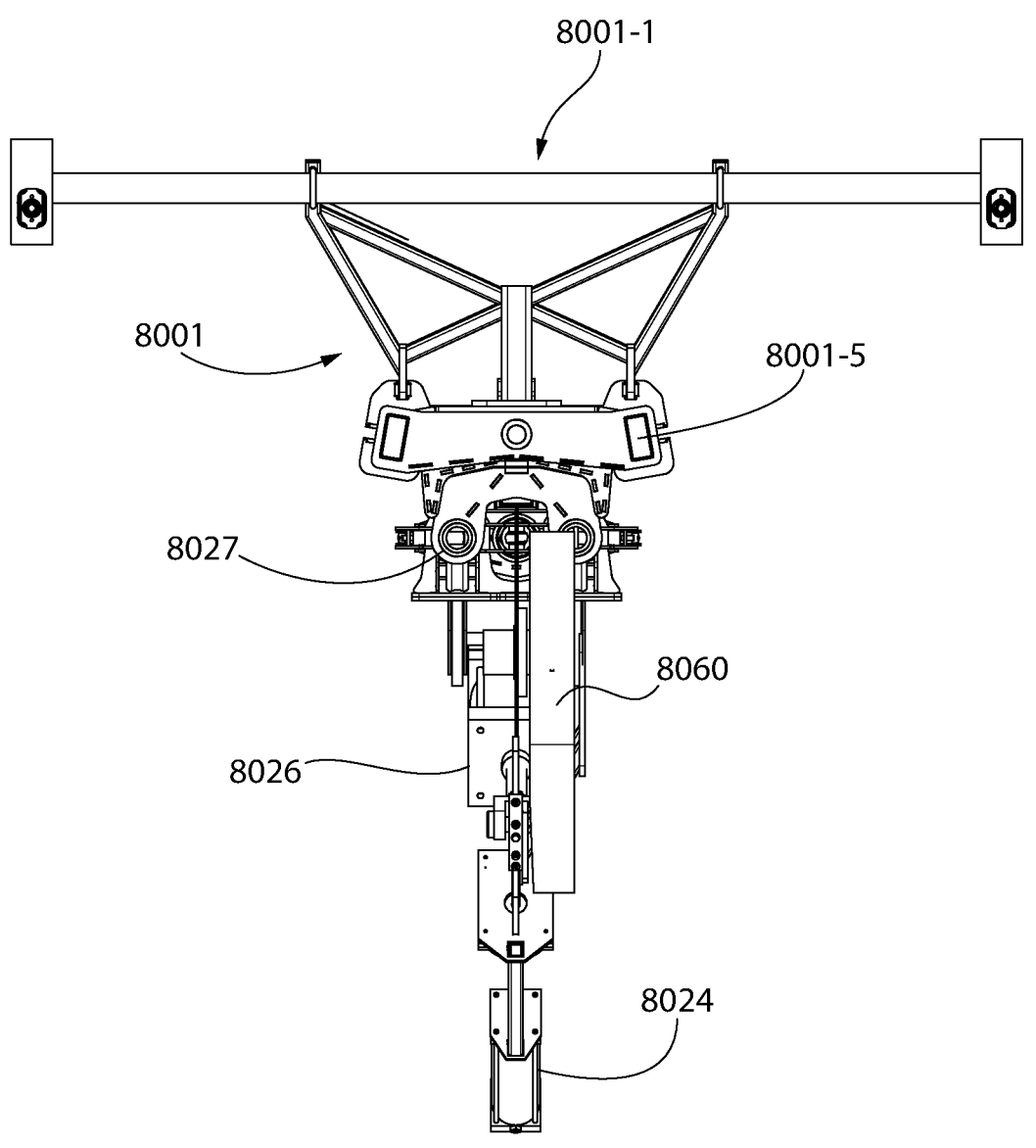
FIG. 15 is a bottom view thereof.

For convenience of description, the collection assembly 8009 may be considered to define a vertical axis VA coaxial with the carriage actuator 8029 (passing through geometric centerline between guide rails 8027) and a horizontal axis HA passing through the hub 8023 of the coulter blade assembly (identified in FIG. 12). Whereas the vertical axis remains fixed in position relative to the carriage chassis 8058 and collection vehicle 8003, the horizontal axis is vertically movable with the coulter blade 8021 and knife assembly 8020 as the carriage 8050 moves up and down along the guide rails 8027. The elongated collection spool 8040 defines a longitudinal axis LA (identified in FIG. 12) which may change between positions parallel to vertical axis VA and obliquely angled to axis VA (see, e.g. FIGS. 26-27), as further described herein.

The collection apparatus 8002 (e.g. knife assembly 8020 and coulter blade 8021) is pivotably coupled to the pair of support arms 8022 coupled to the carriage 8050 via a pivot arm linkage 8061. Linkage 8061 has one end pivotably coupled to hub 8023 and an opposite end pivotably coupled to pivot arm bracket 8055 fixedly mounted to the knife assembly 8020. Bracket 8055 may be mounted to the larger front blade element 8031 in one non-limiting embodiment further described below, preferably on the top portion of the element which remains above the soil during sample collection (see, e.g. FIGS. 5-6, 17 and 26). The knife assembly 8020 of the collection apparatus has a pivot axis PA coinciding with the horizontally oriented rotational centerline of coulter blade hub 8023. Knife assembly 8020 is moveable about its pivot axis in an arcuate path upwards and downwards (see, e.g. FIGS. 26-27).

Knife positioning actuator 8026 may be a pneumatic cylinder type actuator in one embodiment; however, hydraulic cylinders or electric linear actuators may also be used. Actuator 8026 is configured to act in a linear direction via movable operating or piston rod 8026-1 rotatably coupled at bottom to the knife assembly swing arm bracket 8055 via a clevis and pin assembly 8056. At top, the top of the actuator housing is pivotably coupled to cross plate 8054 rigidly mounted between support arms 8022 of the coulter blade assembly via pinned connection 8057. The actuator 8026 supplies a holding force on the knife swing arm and can be used at least partially set both the penetration depth of the knife assembly 8020 and coulter blade 8021 in the soil, and the angle of the knife assembly relative to vertical axis VA.

The knife positioning actuator 8026 serves another useful purpose which protects the collection apparatus 8002 from damage. During use of collection apparatus when collecting a soil sample in the agricultural field AF, an obstruction in the soil may be encountered (e.g. rock, etc.) by the traveling collection apparatus 8002 (see, e.g. FIG. 26). In FIG. 26, the piston rod 8026-1 is in an extended position relative to the actuator housing with the knife assembly 8020 in an angled position (e.g. front side of front blade element 8031 obliquely angled to vertical axis VA) for easier plowing/travel through the soil. If overcoming the obstruction when struck by the knife assembly and/or coulter blade requires greater force than the holding force of the actuator can provide (e.g. air/oil pressure for pneumatic/hydraulic actuator or electric resistance for electric actuator), then the piston rod of the actuator becomes compressed and retracts into the actuator housing, thereby pivotably tilting the knife assembly rearward and raising the collection apparatus to allow the obstruction to pass beneath the knife assembly (compare, e.g. FIGS. 26-27). The front side of front blade element 8031 may be substantially parallel to vertical axis VA now. The cylinder of the knife positioning actuator 8026 thus advantageously serves as a shock absorber to provide a mechanical cushion or "breakaway" mechanism for the collection apparatus when encountering sub-surface soil obstructions to prevent damaging the equipment.

Figure 16:
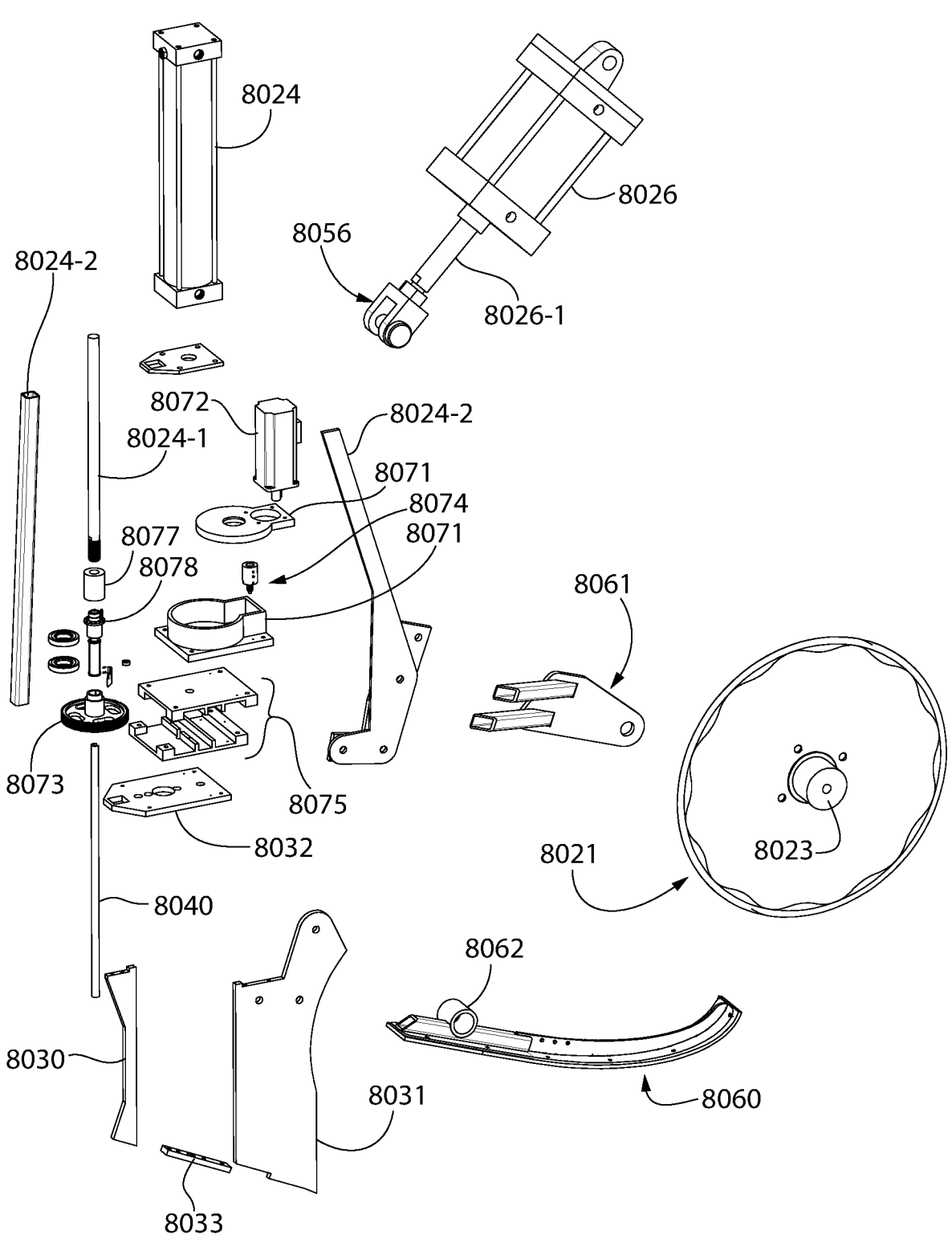
FIG. 16 is a rear exploded view of the collection apparatus of the collection assembly.
Figure 17:
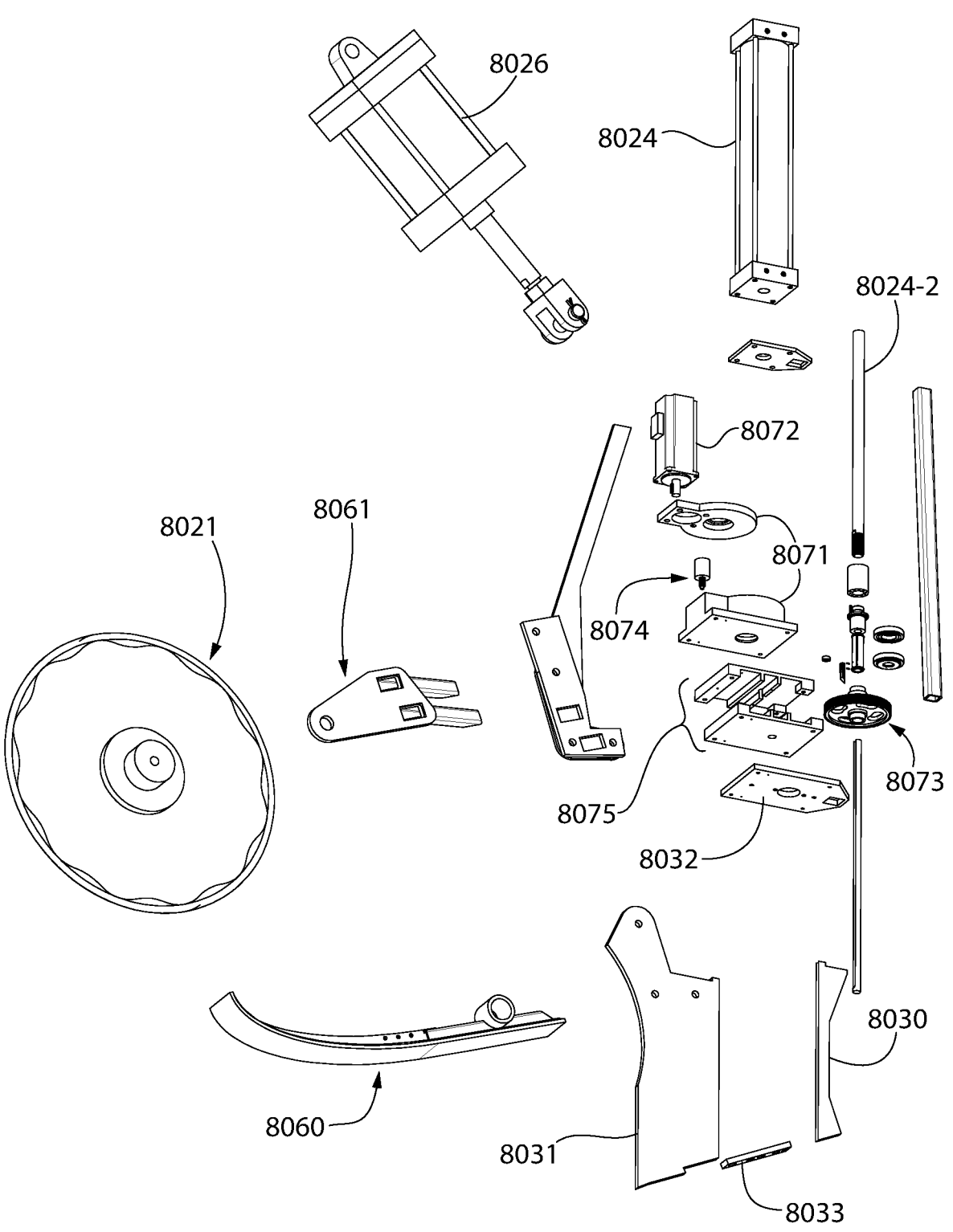
FIG. 17 is a front exploded view thereof.

Knife assembly 8020 comprises a rear blade element 8030, front blade element 8031, top blade mounting bracket 8032, and bottom base plate 8033 (see, e.g. FIG. 16). Base plate 8033 and mounting bracket 8032 may be horizontally elongated with the blade elements sandwiched therebetween. The blade elements are rigidly mounted at their tops to mounting bracket 8032 and at their bottoms to base plate 8033 via any suitable method, such as for example without limitation threaded fasteners, welding, or other fixed mounting methods to provide rigidity to the knife assembly to counteract the soil pressure applied by pulling the assembly through the soil for sample collection.

Figure 6:
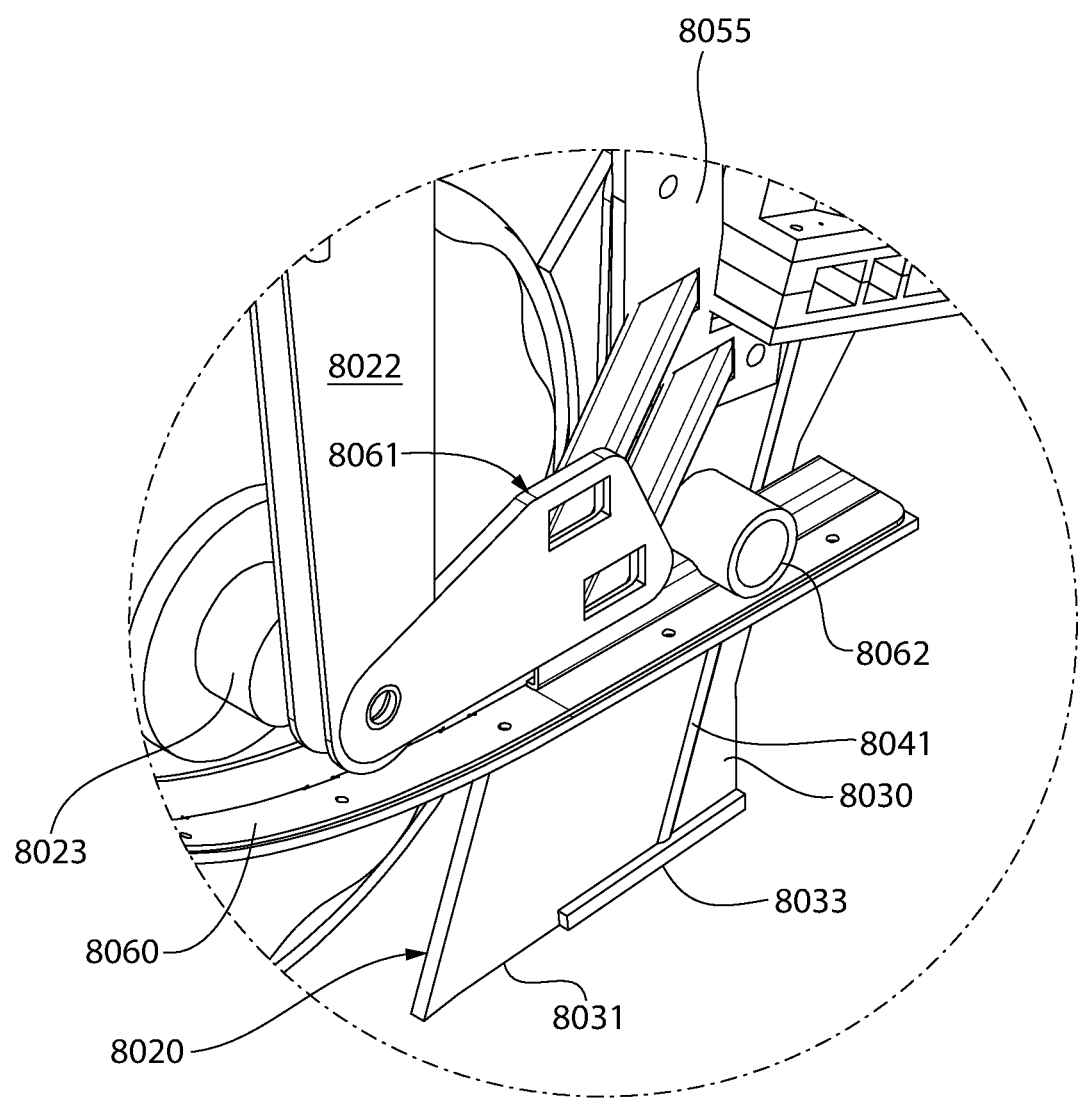
FIG. 6 is an enlarged detail view from FIG. 5.
Figure 7:
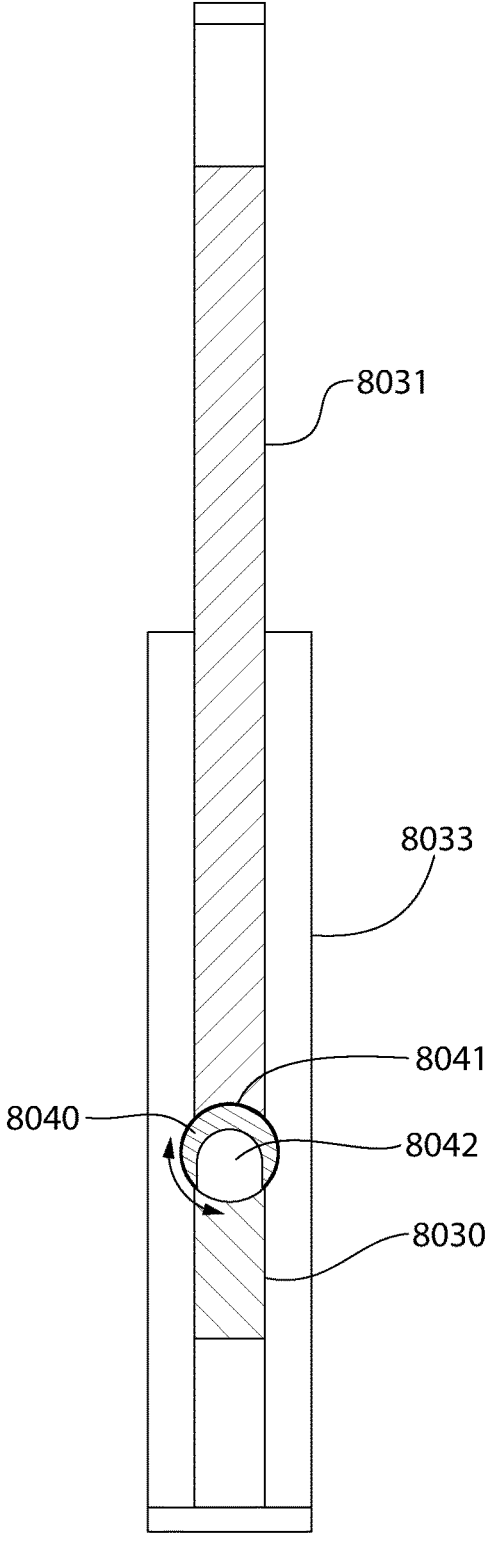
FIG. 7 is a horizontal transverse cross-sectional view of the knife assembly of the collection assembly of FIG. 4.
Figure 8:
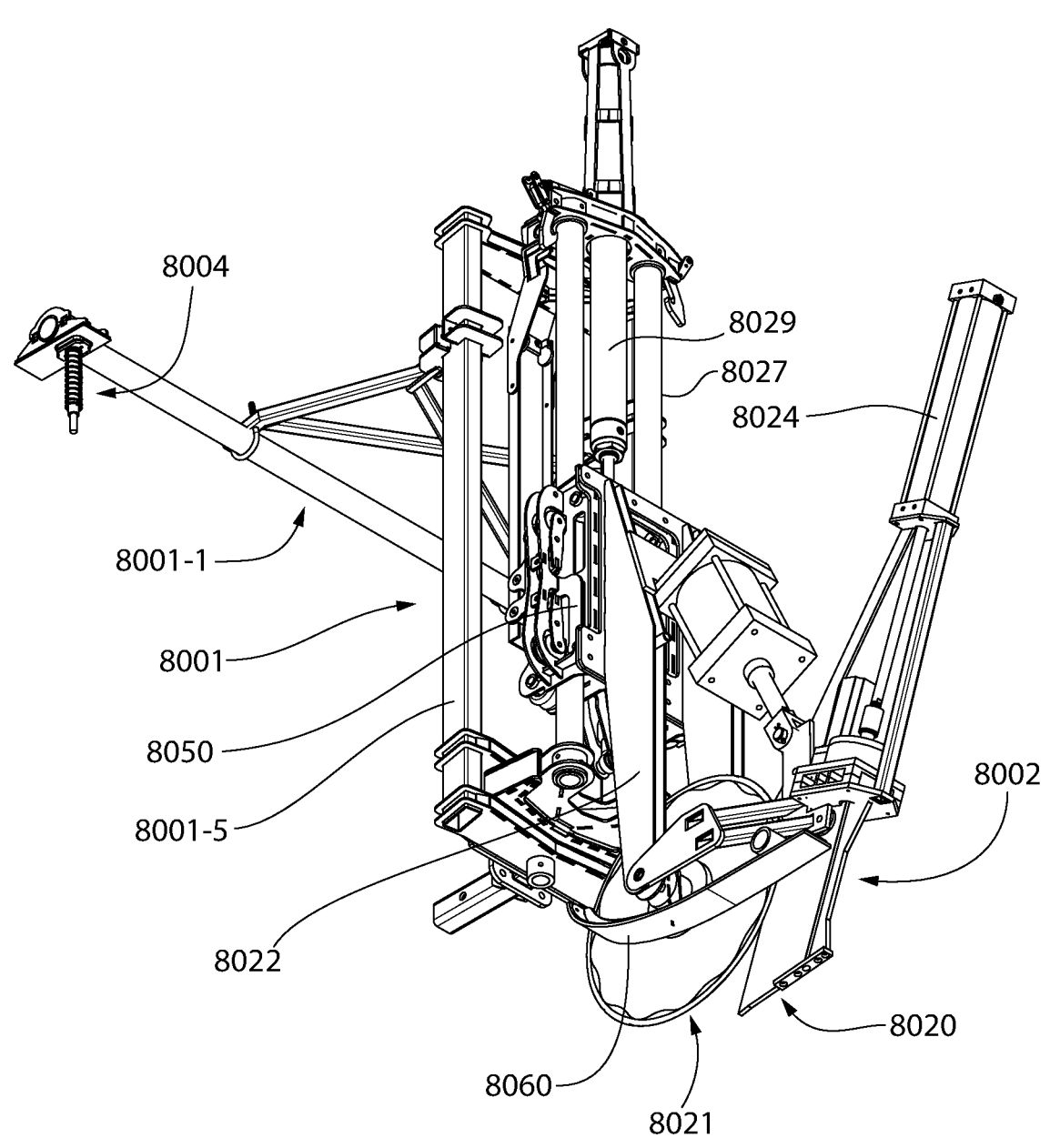
FIG. 8 is a rear bottom perspective view of the collection assembly.
Figure 9:
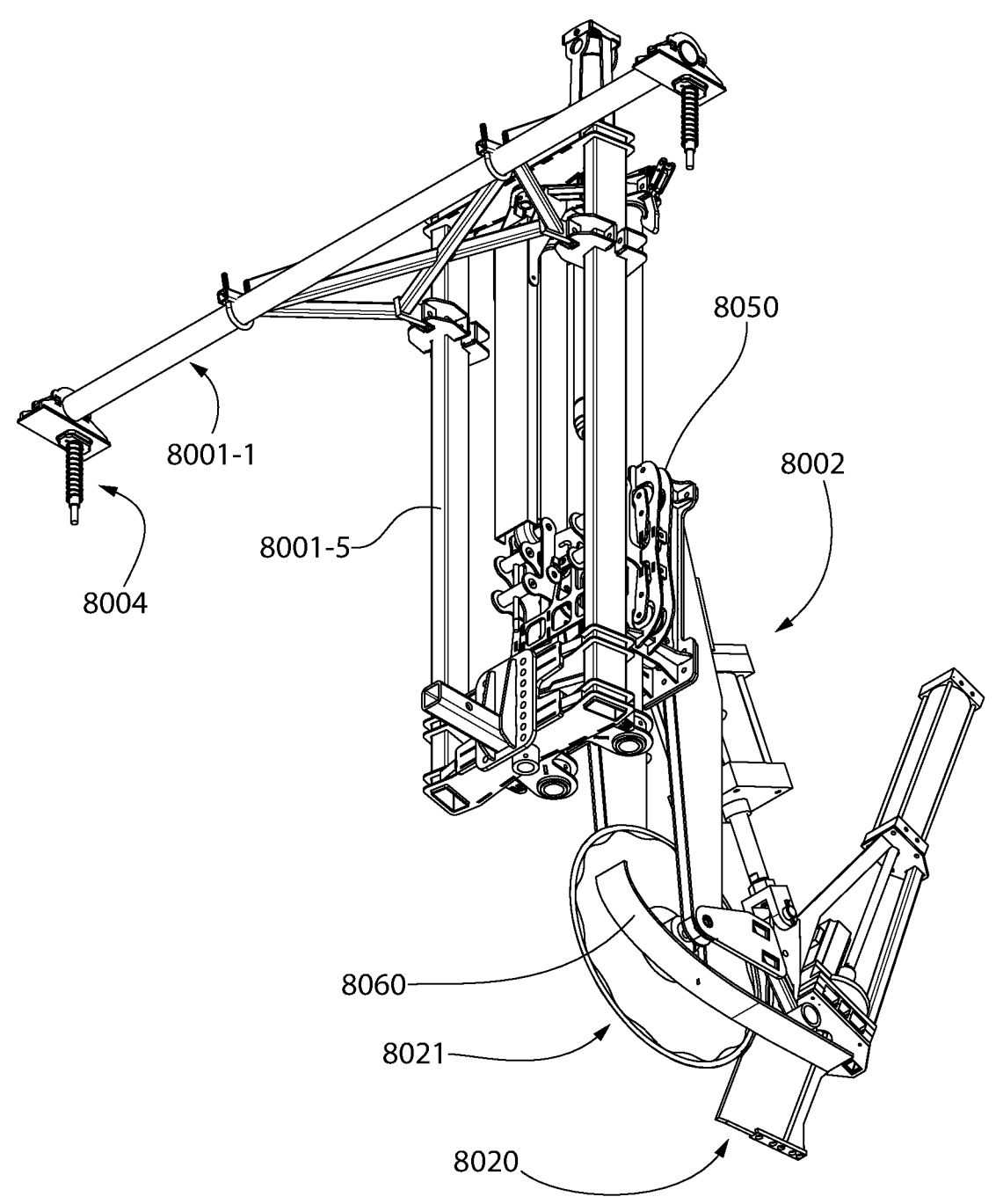
FIG. 9 is a front bottom perspective view thereof.
Figure 10:
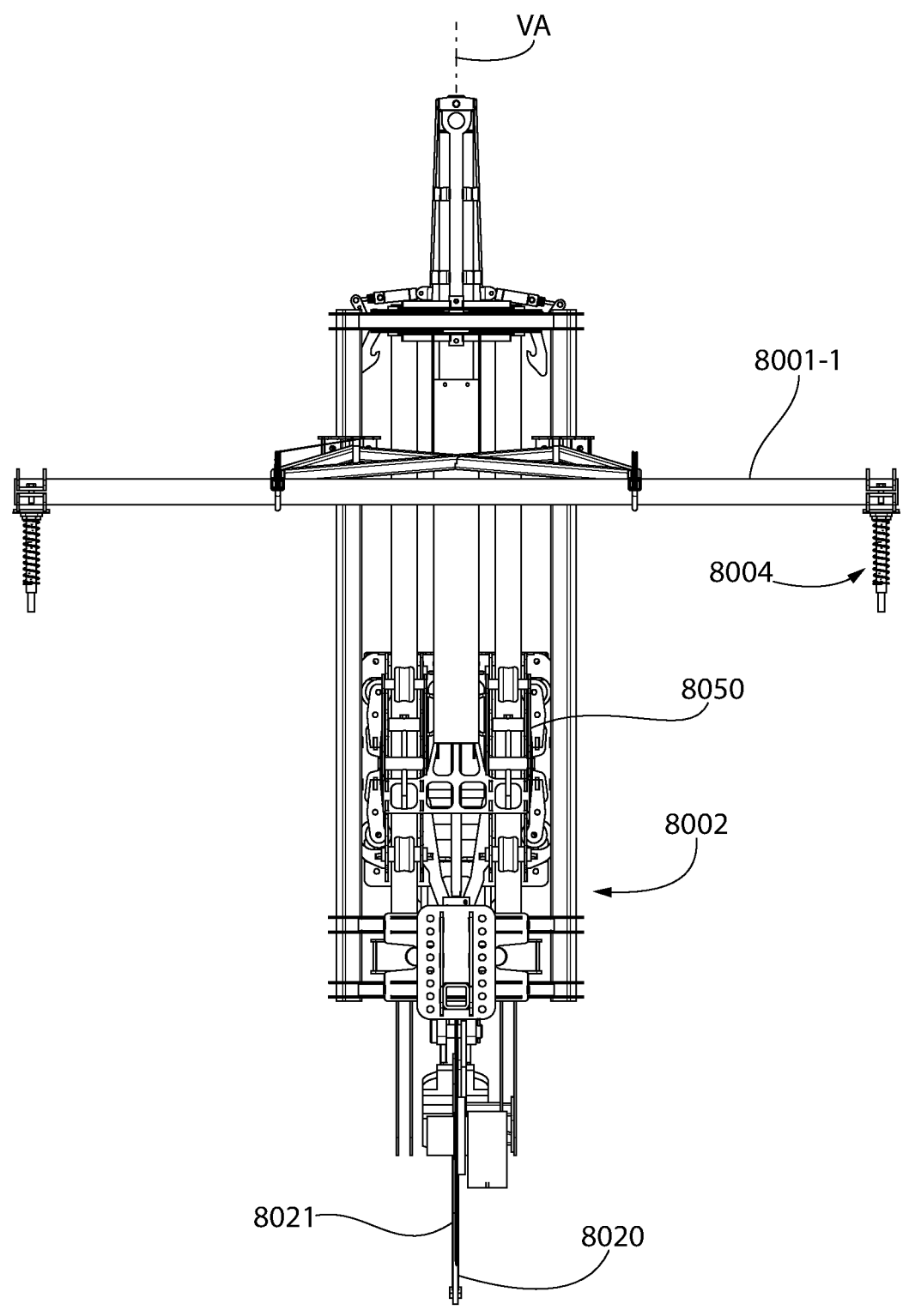
FIG. 10 is a front view thereof.
Figure 11:
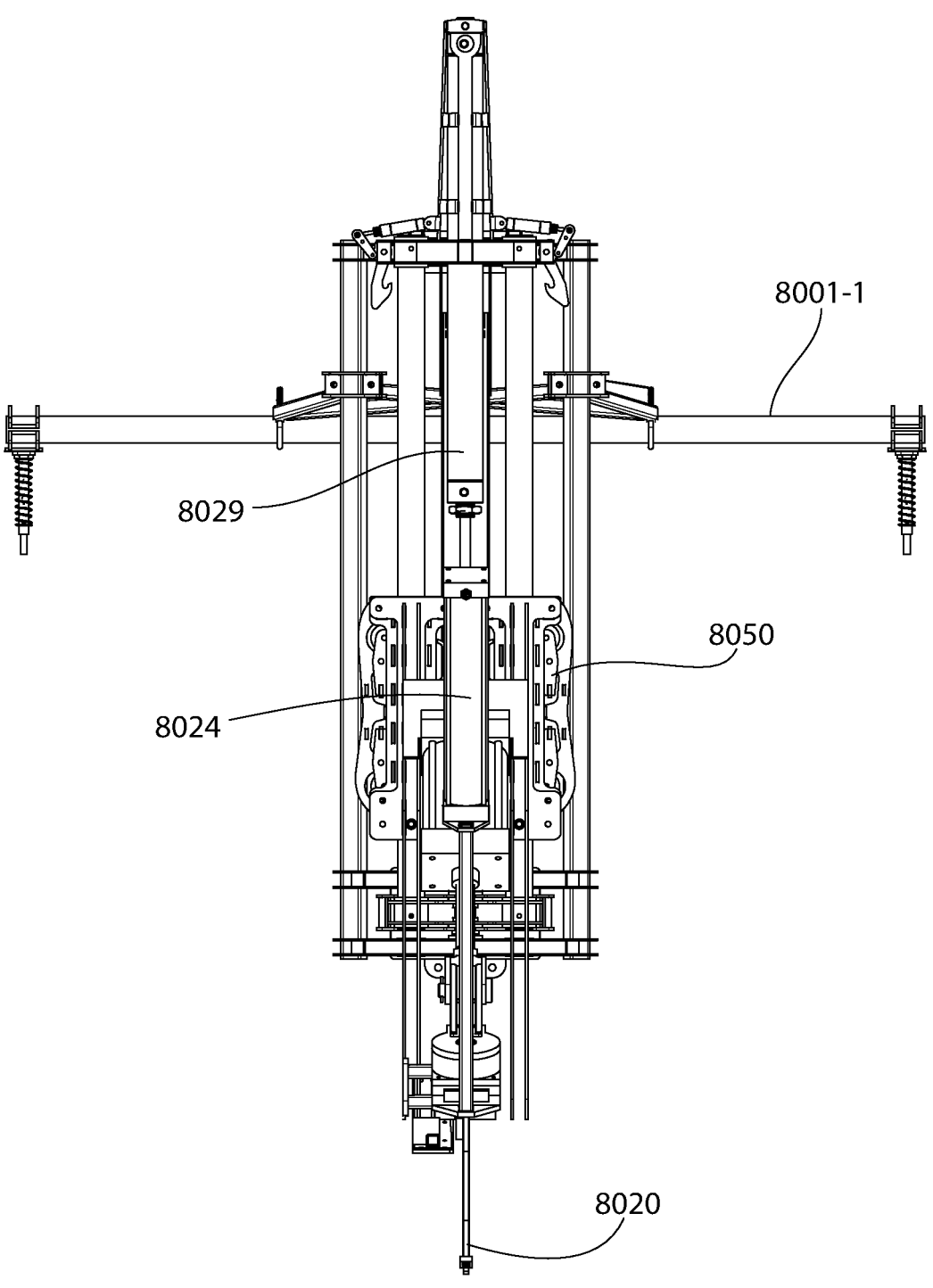
FIG. 11 is a rear view thereof.

The rear and front blade elements 8030, 8031 may be mounted to the base plate in a horizontally axially spaced apart manner along horizontal axis HA of the sample collection apparatus to collectively define a vertically elongated spool slot 8041 therebetween (best shown in FIGS. 6 and 7). Accordingly, slot 8041 is collectively defined by the space created between each blade element. Slot 8041 has a transverse cross-sectional shape complementary configured to the cross-sectional shape of the spool 8040 which may be circular in one embodiment (see, e.g. FIG. 7). Additional slots 8041 may be provided if more than one spool is incorporated into the knife assembly in other embodiments, as further described hereafter. Spool slot 8041 is configured to rotatably and slideably receive the spool 8040 therein. Specifically, spool 8040 is vertically and slideably movable upwards/downwards in the slot, and rotatably movable as well for capturing and retaining the soil sample as further described herein. Both the slot 8041 and spool 8040 may have circular shapes in transverse cross-section as the spool may have a cylindrical configuration in the illustrated embodiment.

Rear and front blade elements 8030, 8031 may be formed of generally flat metallic plates in one embodiment; each having opposing right and left lateral major surfaces which are substantially parallel to each other. Any suitable overall general configuration of blade elements 8030, 8031 may be used so long as the elements sufficient support and house the collection spool 8040 and can penetrate the soil. The blade elements may have different shapes in perimetrical outline, which can be polygonal, non-polygonal, or combinations thereof. The front blade 8031 which engages and plows through the soil head on may be larger and more robust to serve this functional purpose. The leading edge 8120a of front blade 8031 may be angled or wedge shaped (in transverse cross-section) to better plow through the soil. The smaller rear blade 8030 primarily functions to define the spool slot 8041. It bears noting that the forward coulter blade 4021 functions to partially loosen the soil before being encountered by the knife assembly 8020 as it is pulled through the soil. However, the rear and front blade elements 8030, 8031 of knife assembly 8020 extend vertically below the bottom of the coulter blade 8021 and guide ski 8060 (see, e.g. FIGS. 12-13) such the lower portion of the knife assembly encounters soil proximate to the bottom and just below of the furrow or trough plowed by the coulter blade. This soil layer may be somewhat loosed by the coulter blade to reduce frictional resistance on the knife assembly thereby making is easier for the knife assembly to progress forward through the soil to collect the soil samples.

Knife assembly 8020 includes guide ski 8060 which substantially limits the insertion depth of the knife assembly into the soil as seen in FIGS. 26-27. Ski 8060 has a horizontally elongated body and arcuately upturned front end to accommodate undulations in the soil surface of the agricultural field which naturally occur. The ski may be rigidly mounted to one lateral side of the knife assembly (e.g. front blade 8031) via cylindrical mounting boss 8062. In one embodiment, boss 8062 may be welded to the top of the ski and to the side front blade 8031. This creates a structurally robust attachment capable of maintaining the position of the knife assembly 8020 against the soil surface GS and the holding force of knife positioning actuator 8026 (described elsewhere herein) when undulating soil surface conditions or surface debris (e.g. valleys, ridges, rocks, tree branches, etc.) not uncommon in the agricultural field are encountered by the collection apparatus 8002. Ski 8060 may be preferably made of any suitable durable and strong metal.

FIGS. 7 and 16-25 show aspects of the soil collection spool 8040 and associated spool drive mechanism 8070a in greater detail. In one embodiment, spool 8040 may have an elongated cylindrical body with a laterally and outwardly open collection cavity 8042. The cavity may extend for substantially the entire length of the spool from top end 8043 to bottom end 8044. The top end is configured for mounting to spool positioning actuator 8024 which operates to selectively raise or lower the spool in the knife assembly 8020. The bottom end may be closed to retain the captured soil sample. Cavity 8042 may have an arcuately curved contour or shape from side to side to facilitate removal of the captured sample. Spool 8040 may be formed of a suitable metal such as aluminum or steel for ruggedness and durability for the service conditions. In one embodiment, stainless steel may be used for corrosion protection to ensure smooth rotational and linear movement of the spool in the spool slot 8041 of the knife assembly 4020.

Knife assembly 8020 further includes a spool drive mechanism 8070a operably coupled to the collection spool 8040 which operates to (1) rotate the spool for capturing and retaining the soil sample, and (2) raise and lower the spool for ejecting the sample into a sample transport system. To accomplish the foregoing dual motions of the spool, the spool drive mechanism comprises a gear drive 8070 for rotational motion of the spool and a spool positioning actuator 8024 for linear up and down motion of the spool. Each motion and function will be described in turn below.

Figure 25:
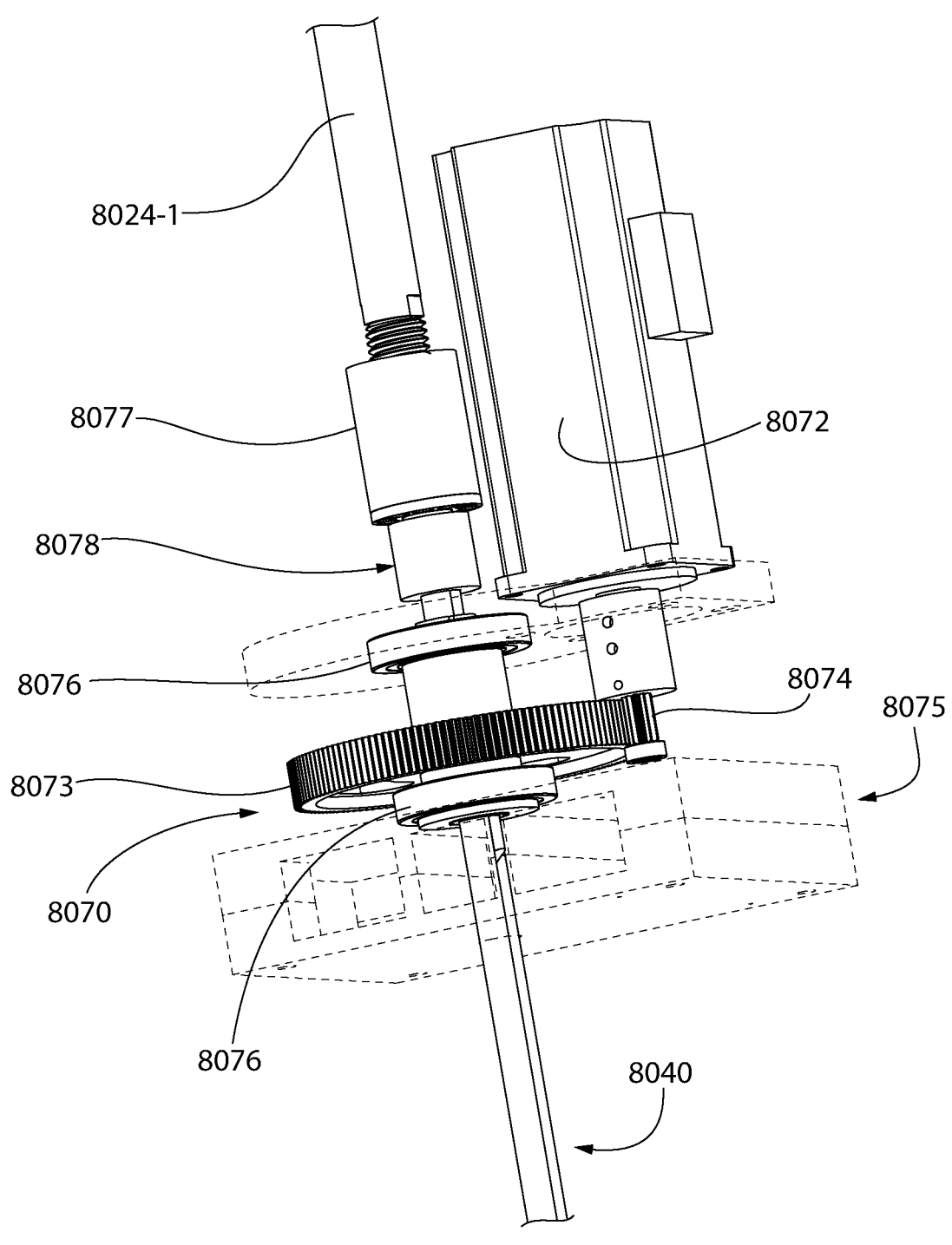
FIG. 25 is a perspective view of gear drive showing the drive and driven gears.

Gear drive 8070 comprises an electric motor 8072 including drive gear 8074 coupled to the motor's drive shaft and intermeshed with a main driven gear 8073 (see, e.g. FIG. 25). Driven gear 8073 is operably interfaced with the collection spool 8040, as further described herein. The drive gear and driven gear may be housed in gear box 8071 of any suitable configuration for protection from the elements and environment. The gear box and motor may in turn be mounted on and supported by the gear drive support base or platform 8075, which may be attached to the top of the knife assembly 8020. In some embodiments, the platform 8075 may be configured for coupling to a sample collection/conveyance system to transport the soil sample to the soil sample analysis system for slurry preparation and chemical analysis as previously described herein. Motor 8072 may be supported by the gear box and includes a drive shaft 8074-1 coupled to drive gear 8074, shaft support bearing 8074-2, and shaft sleeve fitting 8074-3 supporting and surrounding the drive shaft between the drive gear and motor housing.

Figure 18:
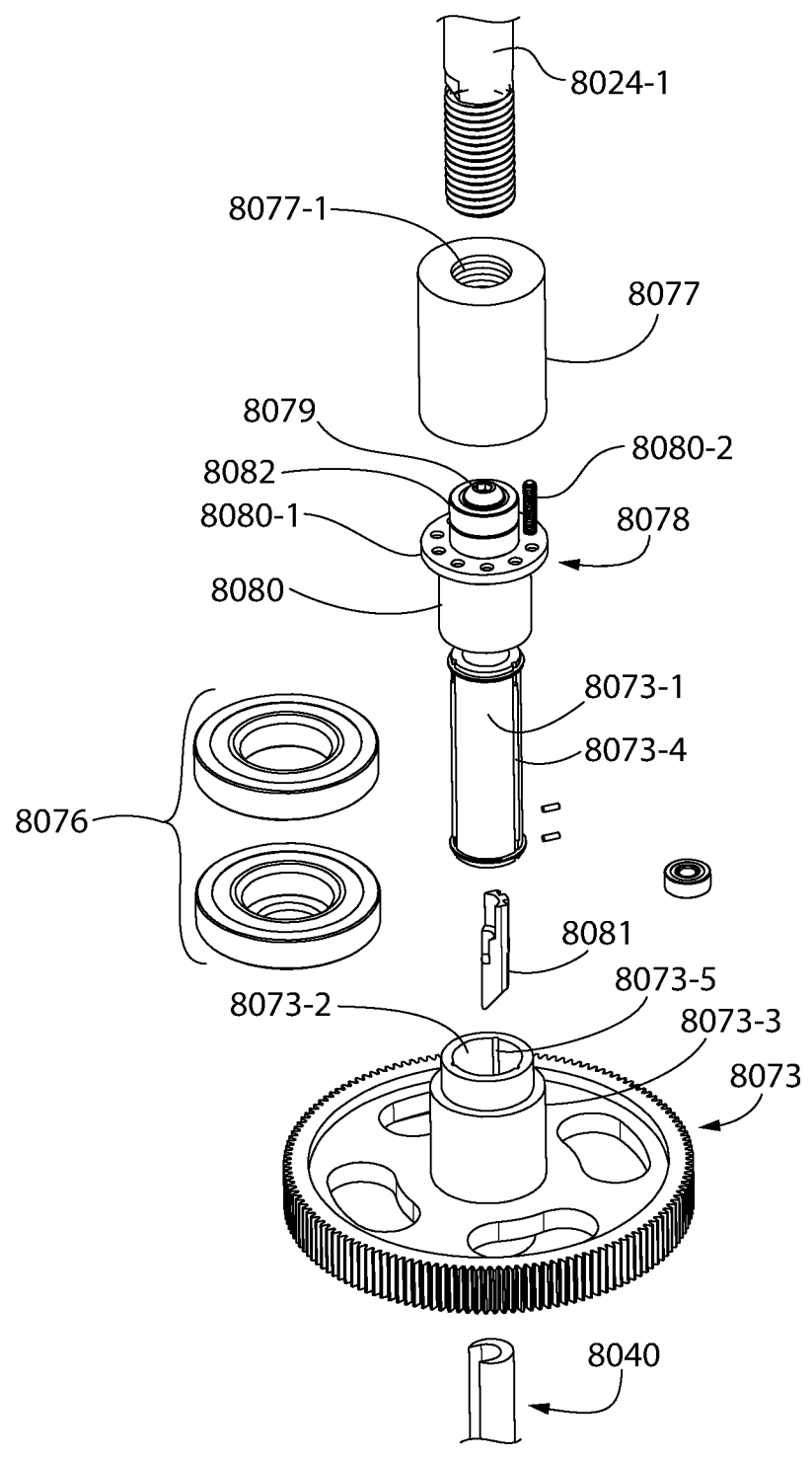
FIG. 18 is a top exploded perspective view of a portion of the collection spool drive mechanism of the collection apparatus.
Figure 19:
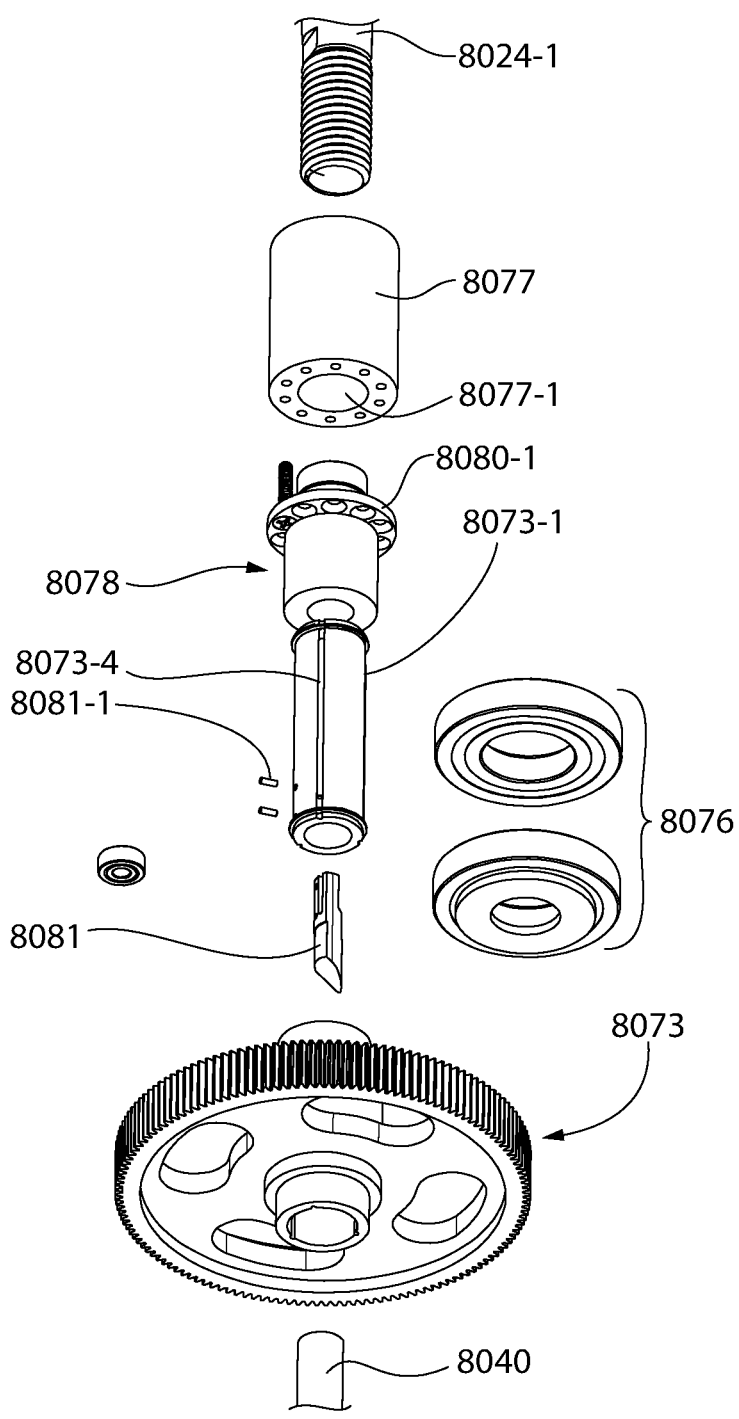
FIG. 19 is a bottom exploded perspective view thereof.
Figure 20:
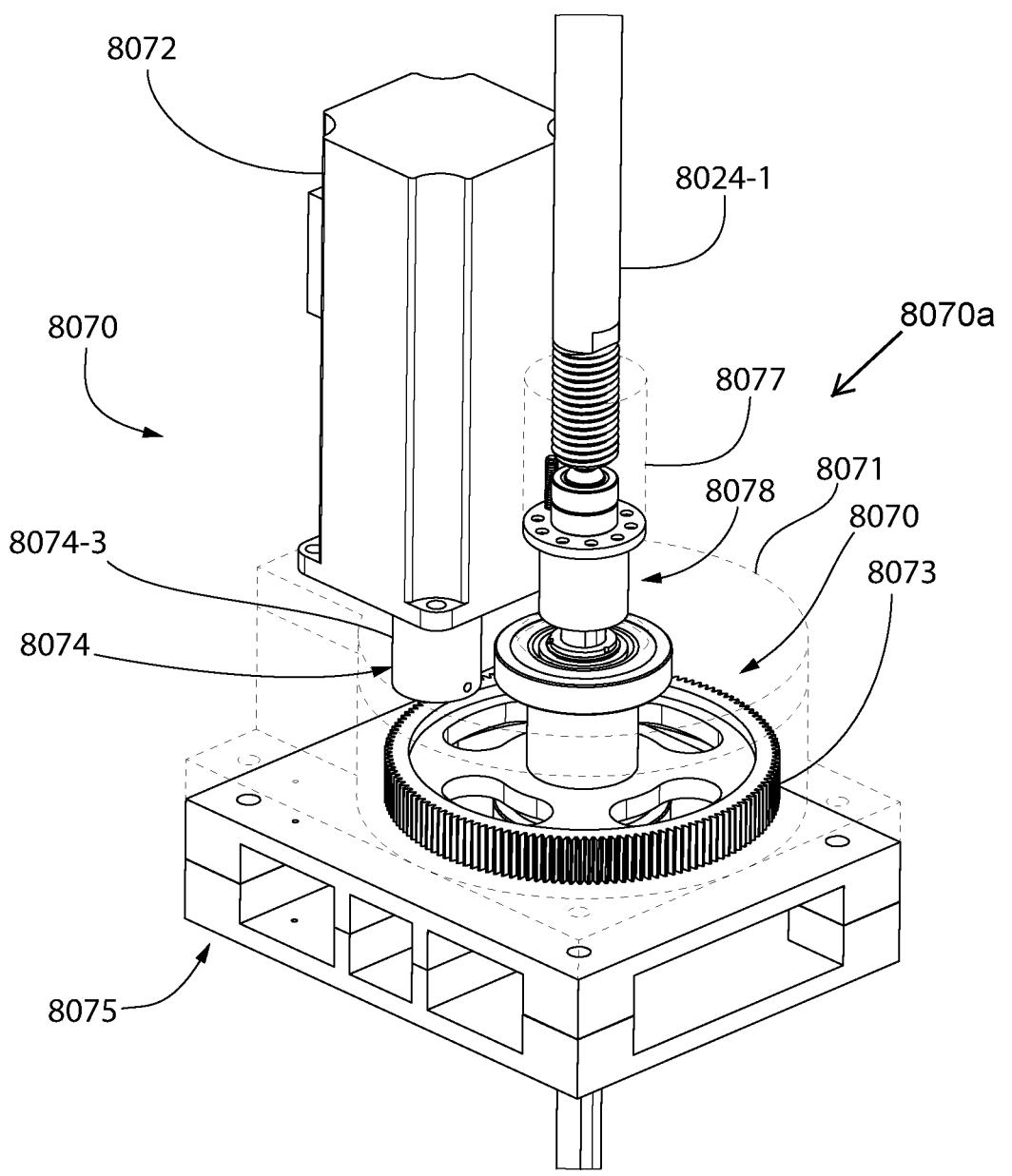
FIG. 20 is an assembled perspective view of gear drive of the spool drive mechanism.
Figure 21:
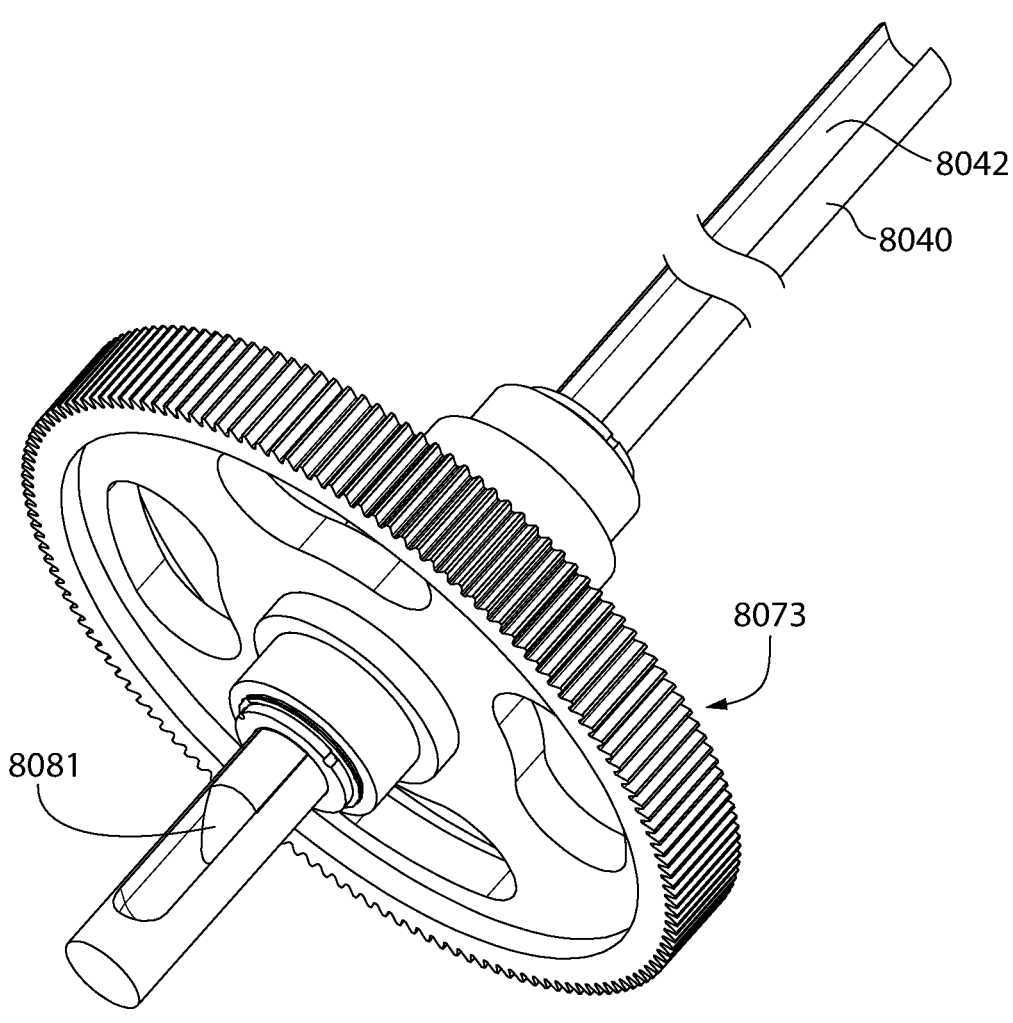
FIG. 21 is perspective view of the driven gear thereof coupled to the collection spool.
Figure 22:
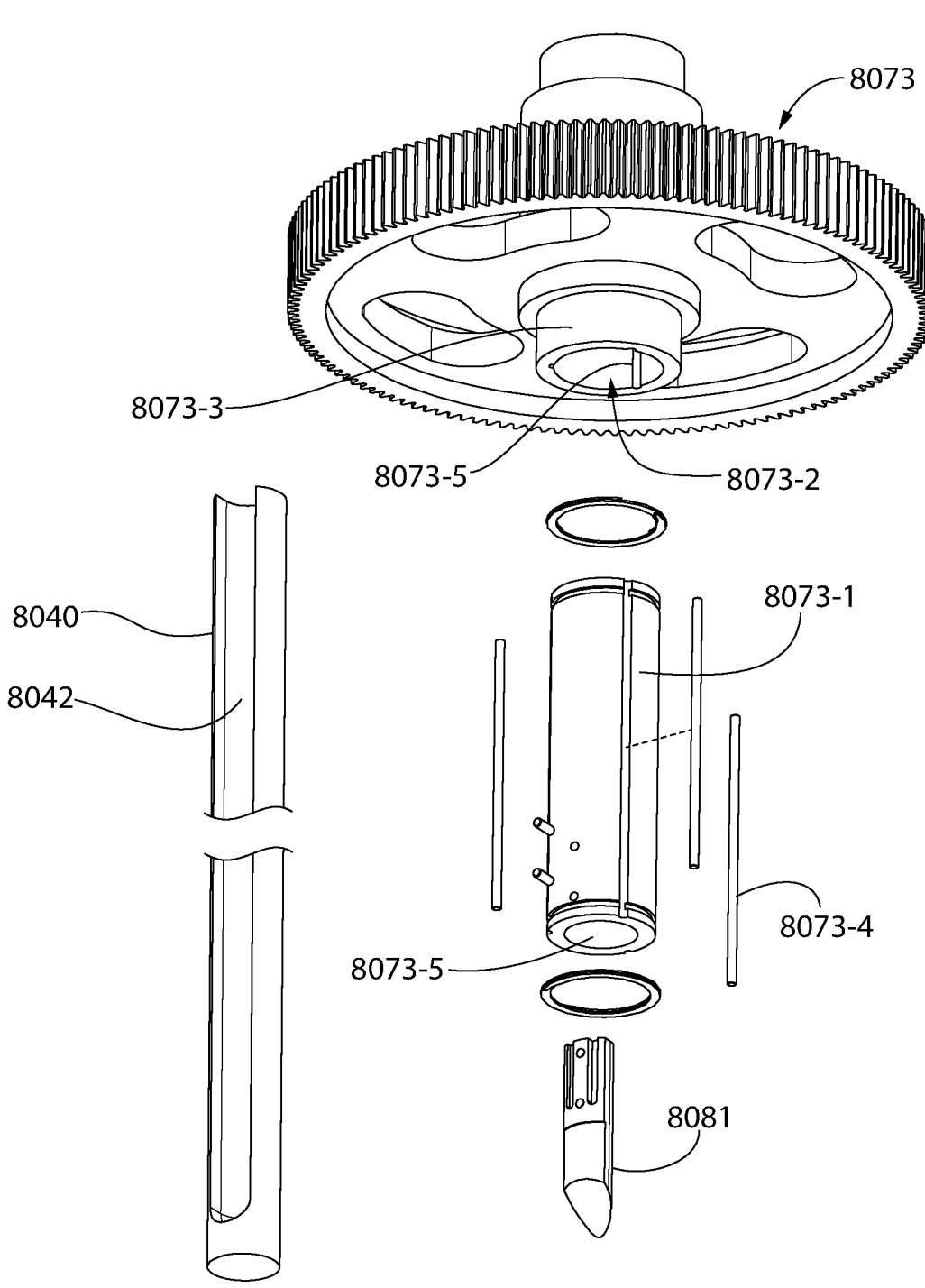
FIG. 22 is a bottom perspective view of the driven gear assembly.
Figure 23:
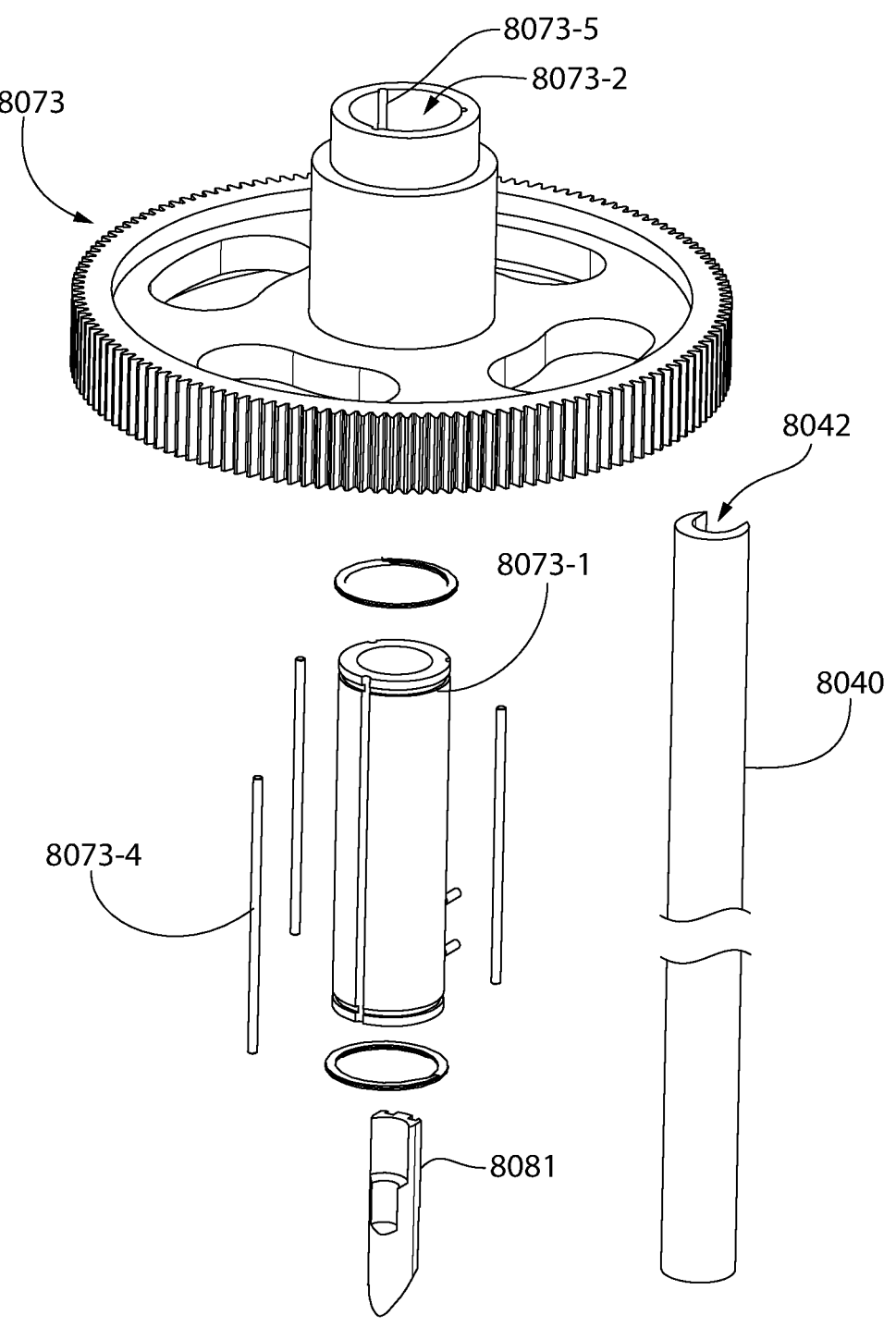
FIG. 23 is a top perspective view thereof.
Figure 24:
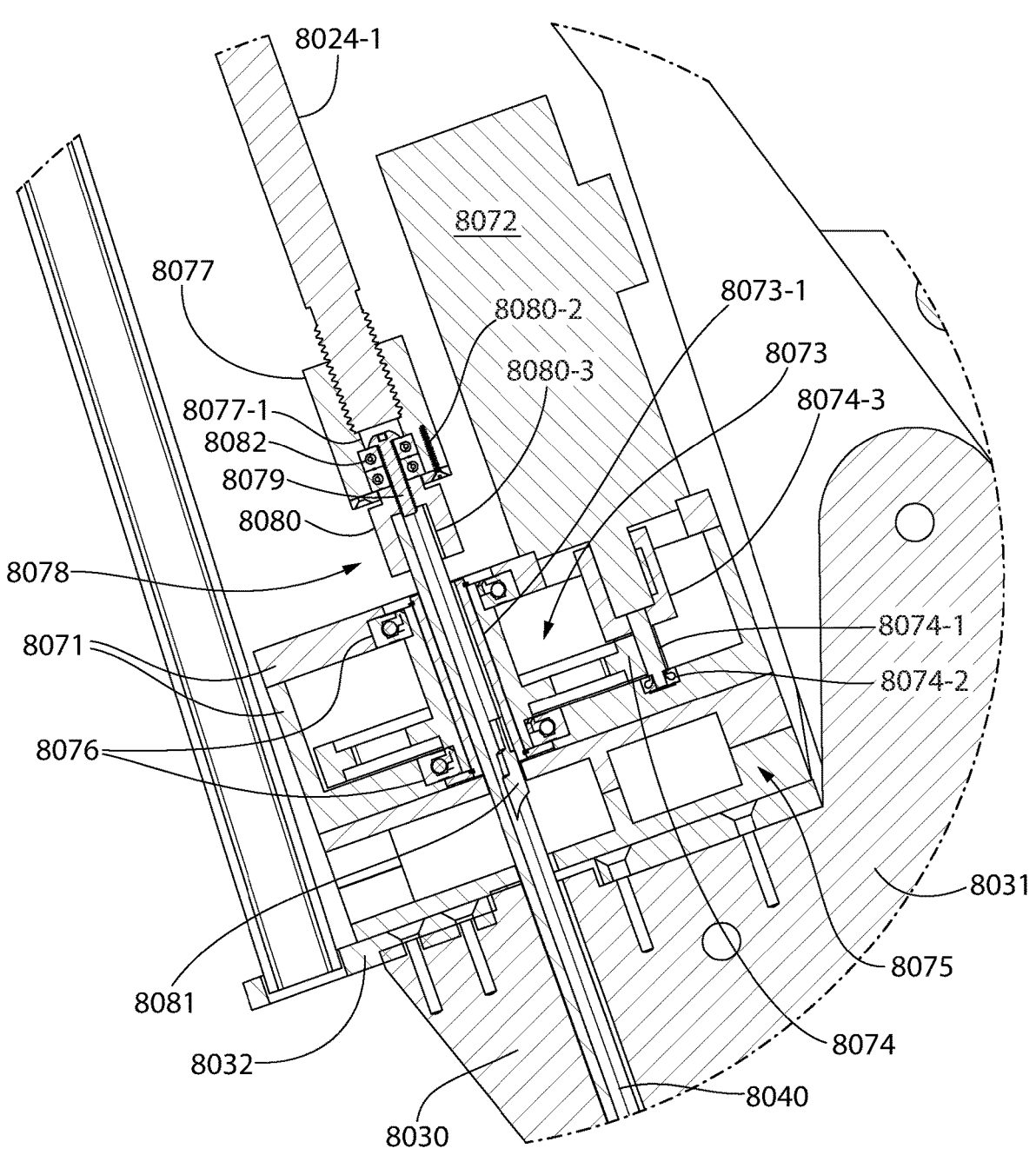
FIG. 24 is a side cross-sectional view of the gear drive.

A pair of gear bearings 8076 of suitable type support the driven gear 8073 for rotational movement (see, e.g. FIGS. 18 and 24). The driven gear assembly may include a tubular hollow drive sleeve 8073-1 inserted through central through passage 8073-2 of the gear hub 8073-3. Collection spool 8040 is received in and slideable upwards/downwards through the through passage 8073-5 of the drive sleeve when the spool is raised and lowered. Externally, the drive sleeve may include a plurality of longitudinal splines 8073-4 which may be removably and insertably keyed to mating longitudinal grooves 8073-5 formed inside the gear hub through passage 8073-2 to rotationally interlock the sleeve and driven gear 8073 such that the sleeve rotates in unison with the driven gear (see, e.g. FIGS. 18-19). The splines 8073-4 may be separate parts attached to the exterior of the drive sleeve in mating longitudinal slots as illustrated, or may be integrally formed as a unitary structural part of the drive sleeve tubular body. Drive sleeve 8073-1 is intended to be an easily replaceable and less costly component than the driven gear 8073 if replacement is required due to wear.

Drive sleeve 8073-1 forms an axially slideable but rotationally interlocked interface with the collection spool 8040 via sample ejector 8081, which may be fixedly attached to the drive sleeve inside through passage 8073-5 of the sleeve by any suitable means. In one embodiment, a pinned connection may be created by pins 8081-1; however, threaded fasteners or other means may be used for a fixed attachment. Ejector 8081 may be mounted to the bottom end of the drive sleeve 8073-1 such that the upper pinned portion of the ejector resides inside the lower portion of the drive sleeve taps 8073-5 while the wedge-shaped lower portion protrudes downwards below the drive sleeve and driven gear (see, e.g. FIG. 21). Sample ejector 8081 is rotationally locked to and nested at least partially within the collection cavity 8042 of collection spool 8040 in a manner which allows axial longitudinal movement of the spool relative to the ejector. The ejector is configured and operable to eject the captured soil sample from the collection cavity for collection and further processing/analysis by the soil analysis system. The ejector 8081 remains stationary in vertical position but rotatable with the gear drive while the collection spool 8040 can be selectively moved axially up/down by spool positioning actuator 8024 through the drive sleeve and driven gear. Ejector 8081 may have an angled wedge-shaped scraper end configured to wedge the soil sample out from the collection cavity 8042 of collection spool 8040 when the spool is raised.

The gear drive 8070 is operable to rotate the collection spool 8040 via engagement with ejector 8081 between an open position for capturing a soil sample, and a closed position for retaining the captured sample. It bears noting that as opposed to manually-operated handheld core extraction devices or probes which vertically pierce the soil in an axial direction, are pushed down to a desired depth, and collect a core sample that is simply retained in the tool as it is straight pulled back out, the present spool 8040 plows through the soil in a direction of travel parallel to the soil surface GS. This captures the soil sample which is forced into the collection cavity 8042 in a direction transverse to the longitudinal axis of spool LA and parallel to the direction of travel of the collection apparatus as it (i.e. coulter blade and knife assembly) plows through the soil at a preselected depth.

Spool positioning actuator 8024 may be a pneumatic cylinder type actuator in one embodiment; however, hydraulic cylinders or electric linear actuators may also be used. Actuator 8024 may be supported by substantially vertical actuator support frame members 8024-2 from the gear drive support platform 8075 and/or knife assembly 8020. The support frame is configured to coaxially align the piston rod with the collection spool 8040 along the longitudinal axis LA of the spool. Actuator 8024 is configured to act in a linear direction via movable operating or piston rod 8024-1 coupled via intermediate elements to the top end of the spool 8040.

Referring particularly to FIGS. 18-19 and 24-25, the bottom end of the spool positioning actuator piston rod 8024-1 may be rigidly coupled to a hollow tubular connector 8077 comprising a longitudinal through passage 8077-1 extending between and through the connector body ends. In one embodiment, a threaded coupling may be provided; however, other forms of rigidly coupling including without limitation pinned connections, shrink fit, threaded fasteners, etc. as some non-limiting examples. Connector 8077 in turn is coupled to freely-rotatable swivel coupling 8078 which is coupled to collection spool 8040. Swivel coupling 8078 includes collar 8080, fastening member 8079, and at least one or a pair of bearings 8082 which rotatably support the fastening member. Collar 8080 may be flanged comprising an annular radially protruding flange 8080-1 which is fixedly attached to the bottom of connector 8077 by a plurality of threaded fasteners 8080-2 such that the collar is not rotatable relative to the connector. The fasteners member 8079 may be a threaded fastener in one non-limiting embodiment (as shown) which extends through a central passage 8080-3 of collar 8080 to threadably engage the top end 8043 of the collection spool 8040. The top end of the spool is received in the lower portion of central passage 8080-3 to engage the fastening member 8079. Operation of the spool positioning actuator 8024 selectively raises and lowers the collection spool 8040 between a lower position for capturing/retaining the soil sample and an upper position for rejecting the soil sample.

Referring to FIG. 24, the connector 8077 and swivel coupling 8078 may be assembled by first attaching the bearings 8082 and fastening member 8079 to the top of the flanged collar 8080 and top end of the collection spool 8040. The head of the fastening member and bearings are inserted through the bottom end of the connector through passage 8077-1. The collar flange 8080-1 is then fastened to the connector 8077, which traps the bearings and fastening member inside the connector via the flange in a rotatable manner.

Figure 53:
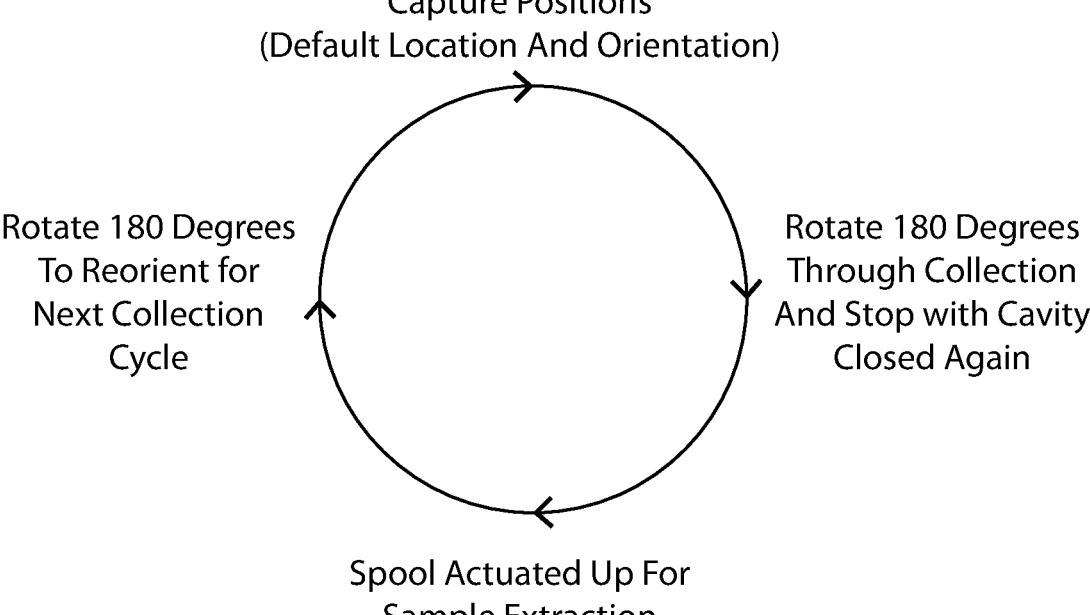
FIG. 53 is a schematic diagram showing a complete spool operating cycle for either the single or double spool embodiments.

A process or method for capturing a soil sample from an agricultural field using the collection apparatus 8002 will now be briefly described. FIG. 53 shows the complete cycle of the collection spool 8040 from start to finish through sample collection, retention, and ejection. First, the vehicle 8003 is driven or pulled to the desired starting location in the agricultural field. The collection apparatus 8002 is in an upper position relative to the soil surface GS and vehicle during transport. The collection apparatus is then lowered to actively penetrate and engage the soil. The desired depth of penetration of the knife assembly and coulter blade 8021 for collecting the soil sample may be adjusted and set by the vertical position of the carriage 8050 via operating the carriage actuator 8029 as previously described herein. This may be performed while the vehicle is stationary, or alternatively while moving. The angular orientation of the knife assembly 8020 may be adjusted by operating the knife positioning actuator 8026 as previously described herein. In one embodiment, the knife assembly may be set to an obliquely angled position to vertical axis VA of collection apparatus 8002 (i.e. front side/edge of front blade 8031) to more readily plow through the soil (see, e.g. FIG. 18). The collection apparatus comprises rotatable coulter blade 8021 and knife assembly 8020 arranged proximate to the coulter blade and comprising at least one rotatable collection spool 8040 comprising the collection cavity 8042. The collection spool may initially be in a lower position in the knife assembly 8020, which may be a lowest position (see, e.g. FIG. 18) set by operating spool positioning actuator 8024 as previously described herein. The bottom end of spool may therefore be positioned at the bottom end of the collection cavity 8042 engaging the top surface of the base plate 8033. The collection cavity 8042 of collection spool 8040 may facing forward or rearward and shield from the lateral openings on each side of the knife assembly 8020 at the spool slot 8041, as shown by Position 1 in FIG. 53.

The collection apparatus 4002 (knife assembly 8020 and coulter blade 8021) is then moved and plowed through the soil at the desired depth in a direction of travel parallel to a surface GS of the soil. The coulter blade creates a furrow or trough ahead of the knife assembly which travels at least partially therein for capturing the soil sample. At a predetermined time (which may be part of a preprogrammed timed sequence), the collection spool 8040 is then rotated full 180 degrees from (1) a first closed position via the first 90 degrees of rotation in which the collection cavity 8042 is shielded from the soil (see, e.g. FIG. 424) to a laterally open position in which the collection cavity is exposed to the adjoining soil so that the soil sample is captured in in the collection cavity 8042, to a (2) opposite second closed/ shielded position via the second 90 degrees of rotation for retaining the soil sample. This is represented by Position 2 in FIG. 53. The collection spool is rotated by gear drive 8070 at predetermined times to both capture and retain the soil sample. In some methods, the spool may rotate continuously through the foregoing first closed position-laterally open soil capture position-second closed positions. The rotational speed of the collection spool 8040 may be selected to allow sufficient time of soil to be forced into the exposed collection cavity 8042. Alternatively, the spool may be first rotated 90 degrees to the laterally open position, held in the open position for a predetermined period of time sufficient to allow soil to be forced into and enter the collection cavity, and then rotated 90 further back to the second closed position for retaining the sample. Either approach may be used as needed and/or desired to collect a complete sample which preferably may fill at least a majority of the spool collection cavity 8042 for its exposed length.

Once the soil sample has been captured, the collection spool 8040 may be raised while in the second closed position (Position 2, FIG. 53) to an upper position relative to knife assembly 8020 via actuation and linear operation of spool positioning actuator 8024. As the spool is raised, the ejector 8081 exposed immediately below the driven gear 8073 in the gear drive support platform and above the top of the knife assembly 8020 slides through and scrapes the sample out of the spool collection cavity 8042 for capture by a sample collection/conveyance system for further processing to prepare the sample slurry and to ultimately chemically analyze the slurry to quantify concentration of the analyte of interest. It bears noting that because the ejector 8081 is positioned above the knife assembly 8020, the sample may be positively ejected from the spool 8040 while still in the second closed position without further rotation of the spool. Portions of the collection cavity 8042 above the knife assembly are therefore exposed.

After the sample has been ejected, the method may continue by rotating the spool back to the first closed position (Position 1, FIG. 53) while the spool is still in the upper position, and then lowering the collection spool 8020 in the knife assembly back down to the initial lower position. In alternative implementations of the method, the spool may be lowered without rotation while in the second closed position (Position 2, FIG. 53). Since both lateral sides of the knife assembly 8020 are open at the spool slot 8041 as shown in FIG. 7, the foregoing sample collection cycle may be repeated in the same manner previously described above but from the second lateral side of the knife assembly as the spool is rotated from Position 2 back to Position 1. Using such an approach, a sample may be collected with each 180 degree rotation of the collection spool 8040 and cavity 8040 from front to rear, and rear to front. This doubles the number of samples collected with each 360 degree rotation of the spool. Accordingly, the spool need not be rotated back to the initial starting position (Position 1) of the collection cavity after sample ejection for each time a sample is to be collected.

It bears noting that the collection spool 8040 may be rotated in either direction during the soil sample capture and ejection process. In some embodiments if reversible motors 8072 are used, the spool may rotate 90 degrees in a first direction from an initial closed position to an open position to capture the sample, and then rotate back 90 degrees in an opposite direction back to the same initial closed position to reclose the collection cavity 8082 to retain the sample and raise the spool for sample ejection. Accordingly, numerous variations of the foregoing method are possible which are all contemplated by the present disclosure.

In a preferred but non-limiting embodiment referring to FIG. 18, the foregoing sample collection process or method may be automatically controlled by a programmable controller, such as without limitation system controller 2820 previously described herein or a separate dedicated collection controller which may be operably linked to and communicating with the system controller 2820 to coordinate the entire cycle of sample collection, processing, and analysis. The carriage actuator 8029, knife positioning actuator 8026, and spool positioning actuator 8024 may thus be operably and communicably coupled to and under the control of system controller 2820 which activates each actuator at the desired time which may be preprogrammed and/or based on input from a human operator via any suitable wired or wireless electronic processor-based personal input device (e.g. smartphone, tablet, laptop, etc.) which establishes two-way communications. In the case of pneumatic or hydraulic actuators, it bears noting that control may comprise the system controller 2820 operating air or oil control valving associated with the actuator, which in turn controls operation of these type actuators. In the case of electric linear actuators, the controller 2820 may be directly coupled to and act on the actuator to electrically control its operation. Various other control schemes are possible.

FIGS. 42-52 depict a two-spool embodiment of a collection apparatus 8002A according to the present disclosure. The support frame 8001 and other elements of the collection assembly 8009 previously described herein for the single spool embodiment of FIGS. 3-41 remain the same in structure and operation. They will not be described in repetitive detail again for sake of brevity. Only additional or different aspects of the dual spool embodiment will be further described as necessary. Elements previously assigned numerical designations for the foregoing single spool embodiment description have the suffix "A" added for the two-spool embodiment presently being described.

The primary difference in the present two-spool embodiment is that two spools 8020A are rotatably supported by the knife assembly 8020A which is modified to include two parallel elongated spool slots 8041A; one each rotatably and axially slideably receiving a spool. This allows a greater number of soil samples to be collected with each pass of the knife assembly through the field. In addition, the timing with which each spool 8040A will be open for collecting a sample, or closed for shielding the collection cavity 8042A or retaining a collected sample may be timed via the system controller 2820 to ensure that only a single sample is collected at a given time. Advantageously, one spool 8020A may be in the lower position collecting a soil sample while the second spool is in the upper position for ejecting the sample. The two spools then alternate and switch position as the collection apparatus 8002A travels, thereby allowing samples to be collected with greater frequency for a given distance of travel through the field by the knife assembly 8020A. For example, for 20 feet of linear travel of the vehicle 8003 and collection apparatus 8002 in a row through the soil, twice the number of soil samples may be collected in comparison to the foregoing single spool collection apparatus embodiment with a shorter linear distance between the collection points for each sample. When the samples are analyzed by the system, this data can be used to generate greater detailed mapping of levels of soil nutrients (e.g. nitrogen, potassium, etc.) or other analyte of interest for the agricultural field. It bears noting that in some embodiments, more than two spools may be provided which are movably carried by the knife assembly to further reduce the distance between soil sampling points in the field.

To accommodate independent rotary and axial linear motion of the two spools 8020A, a modified gear drive 8070A and separate spool positioning actuator 8024A are provided for each spool. It bears noting that only a single carriage actuator 8029 and knife positioning actuator 8026 is again needed for operation and deployment of the dual-spool collection apparatus 8002A. The two-spool gear drive 8070A includes two sets of electric motors 8072A each with a rotatable drive gear 8074A and an associated intermeshed driven gear 8073A, two drive sleeves 8073-1A each rotationally interlocked with a driven gear 8073A, two sample ejectors 8081A, and two sets of spool positioning actuator to collection spool 8040A couplings each including a connector 8077A and swivel coupling 8078A coupled thereto with the same previously described herein sub-parts. It bears noting that each driven gear 8073A and drive gear 8074A combination may act and rotate independently of the other thereby allowing the timing for rotating each spool to collect, retain, or eject a soil sample be independently controlled To accommodate two spools, the knife assembly 8020A is modified to incorporate two spool slots 8041A. Using the same fabrication methodology as the single spool collection knife assembly 8020, the present dual spool knife assembly 8020A therefore comprises a rear blade element 8030A, front blade element 8031A, intermediate blade element 8030-1A, and top blade mounting bracket 8032A and bottom base plate 8033A. The rear, front, and intermediate blade elements may be mounted to the base plate in a horizontally axially spaced apart manner along the horizontal axis HA of the collection apparatus 8002A to collectively define a pair of vertically elongated spool slots 8041A therebetween (see, e.g. FIGS. 48-50). The blade elements may have any suitable configuration and act in the manner shown in FIGS. 26-27 and previously described herein for collecting soil samples. The blade elements are fixedly attached to and between base plate 8033A and mounting bracket 8032A in the same manner previously described herein (e.g. fasteners used for detachable coupling or welding used for permanent coupling).

Each collection spool 8040A of the two-spool collection apparatus 8002A operates according to the same method/process previously described herein for the single spool embodiment, which will not be repeated here for the sake brevity. The collection cycle may be controlled automatically by the system controller 2820 in the same manner. Using the controller, the timing and sequencing for collection, retaining, and ejection of the samples for each of the pair of spools may be preprogrammed and automatically implemented in the manner previously described above.

In one embodiment, a method for capturing soil samples from an agricultural field may comprise: providing a collection apparatus comprising a rotatable coulter blade, and a knife assembly arranged proximate to the coulter blade and comprising rotatable first and second collection spool each comprising a collection cavity configured for capturing soil samples; placing each of the first and second collection spools in a first closed position; plowing through the soil at a depth with the collection apparatus in a direction of travel parallel to a surface of the soil; rotating the first collection spool from a first closed position in which the collection cavity is shielded from the soil to an open position in which the collection cavity is exposed to the soil to capture a first soil sample in the collection cavity; rotating the first collection spool to a second closed position for retaining the first soil sample; raising the first collection spool in the second closed position and ejecting the first soil sample from the collection cavity; and simultaneous with raising the first collection spool, rotating the second collection spool from a first closed position in which the collection cavity is shielded from the soil to an open position in which the collection cavity is exposed to the soil to capture a second soil sample in the collection cavity of the second collection spool. The method may further comprise rotating the second collection spool to a second closed position for retaining the second soil sample; and raising the second collection spool in the second closed position and ejecting the second soil sample from the collection cavity. The method may further comprise lowering the first collection spool simultaneous with raising the second collection spool.

Knife-Type Soil Sample Collection System Alternative Embodiments

FIGS. 54-85 show alternative embodiments of the mobile soil sample collection system 8000 and various components thereof previously described herein. The following sections describe those alternative embodiments.

FIGS. 54-60 depict a wheeled soil sample collection vehicle 2802 in the form of a towed or pulled hitch-coupled soil sample collection trailer 8100 specially configured for mounting soil sample collection assembly 8009 of the mobile soil sample collection system 8000 thereto and to permit the sample collection apparatus 8002 to access and extract soil samples from the agricultural field AF. As previously described herein, collection assembly 8009 generally includes support frame 8001 and collection apparatus 8002 movably mounted to and supported by the frame for collecting soil samples. Collection apparatus 8002 comprises the leading coulter blade 8021 and trailing sample collection knife assembly 8020 previously described herein which collectively constitute the soil engaging elements of soil sample collection apparatus 8002. As further described below, sample collection trailer 8100 is configured to mount the collection apparatus 8022 inside of the vehicle frame for a more stable mounting. As opposed to hanging the collection apparatus off of the rear end of the sampling vehicle, this positioning is able to better absorb vibrations induced by drawing the collection apparatus through the soil at a depth particularly when the soil engaging elements are centered between the wheels.

Trailer 8100 generally comprises a structural vehicle frame 8103 defining a horizontal centerline longitudinal axis LA, front end 8101, rear end 8104 and pair of opposing longitudinal extending lateral sides 8105. Frame 8103 defines a large central equipment opening 8108 between the sides 8105 for mounting the collection apparatus 8002 therein. Equipment opening 8108 may extend axially and laterally for a majority of the longitudinal length and transverse width of the frame 8103 in one implementation as shown. Frame 8103 is preferably formed of a suitably strong metallic structural members which may be of any cross-sectional structural shape (e.g. I-beams, structural L angles, C-sections, box beams, etc.) to provide rigid support for the collection apparatus 8002 coupled thereto. Frame 8103 in one embodiment includes a plurality of longitudinal structural members 8103a and transverse structural members 8103b. The width of central equipment opening 8108 is defined between the longitudinal steel members 8103a. The longitudinal and transverse members collectively define central equipment opening 8108 as shown.

Support frame 8103 for soil sample collection apparatus 8002 is configured to rotatably support a pair of front wheels 8106 concentrically aligned with transverse wheel axis AX1 and pair of rear wheels 8107 concentrically aligned with transverse wheel axis AX2. Axes AX1 and AX2 extends through the central hub of the wheels 8106, 8107 at their geometric centers. The provision of four wheels provides stability for the collection apparatus 8002 to maintain engagement of the soil engaging elements (coulter blade 8021 and sample collection knife assembly 8020) with the soil at an adjustable preselected depth.

In one non-limiting embodiment as shown, wheels 8106, 8107 are each preferably rotatably supported by a separate individual torsion axle 8109 rigidly mounted to the sides 8105 of the frame 8103. Torsion axles 8109 do not extend laterally through the central equipment opening. Advantageously, this maintains a large clear equipment opening 8108 free of any portion of the axles extending therethrough from side to side of the trailer. Accordingly, four separate torsion axles 8109 are provided for wheels for the illustrated embodiment. Multiple axles advantageously further aid in compensating for and absorbing forces created by changing and undulating field topography engaged by the collection apparatus 8002, thereby providing the sampling mechanism a smoother more stable ride across the agricultural field AF to ensure positive engagement of the knife assembly 8020 with the soil during sample collection. In one embodiment, this functionality is further enhanced by a trailer suspension system in which each axle 8109 is supported by a dedicated and associated spring suspension member 8113 so that each wheel can move up/down independently of the others as it encounters undulations in the soil surface GS (e.g. hills and valleys) as the trailer 8100 is pulled through the agricultural field. Any suitable type of spring suspension may be used.

Hitch 8102 on front end 8101 of trailer frame 8103 is configured for detachable coupling to a counterpart hitch coupler 8111 of a self-powered and engine driven vehicle 8110 operable to pull the trailer through the agricultural field AF. Vehicle 8110 may be any suitable wheeled vehicle such as without limitation a tractor, pickup truck, or other agricultural mobile equipment configured to traverse the agricultural field.

All support equipment for the soil sample collection assembly 8009 including but not limited to an auxiliary power unit 8112, power transmission, electronic controls and modules, sample conveyance (post collection), pumps, compressors, and wireless communication equipment may be contained within and supported by trailer 8100. Power unit 8112 provides electrical power to the collection apparatus 8002, electronic controls/modules such as a programmable controller, and sample conveyance equipment (e.g. mechanical, pneumatic, etc.). In one embodiment, power unit 8112 may be a liquid fuel powered electric generator comprising an engine which is configured for generating electric power. In other embodiments, power unit 8112 may be a battery-powered unit having rechargeable batteries.

Figure 59:
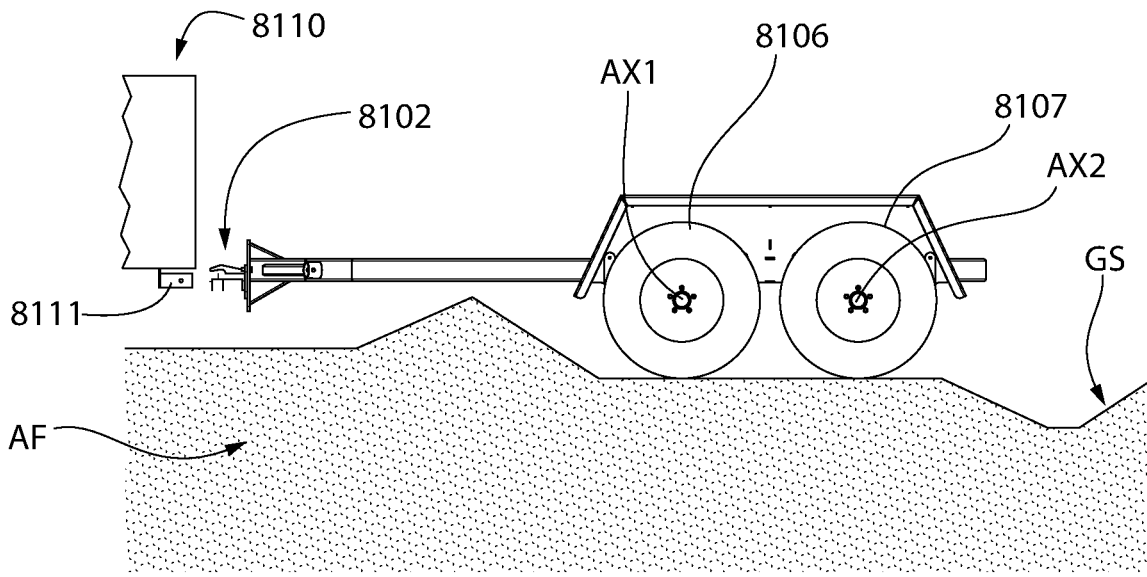
FIG. 59 is a side view thereof.
Figure 60:
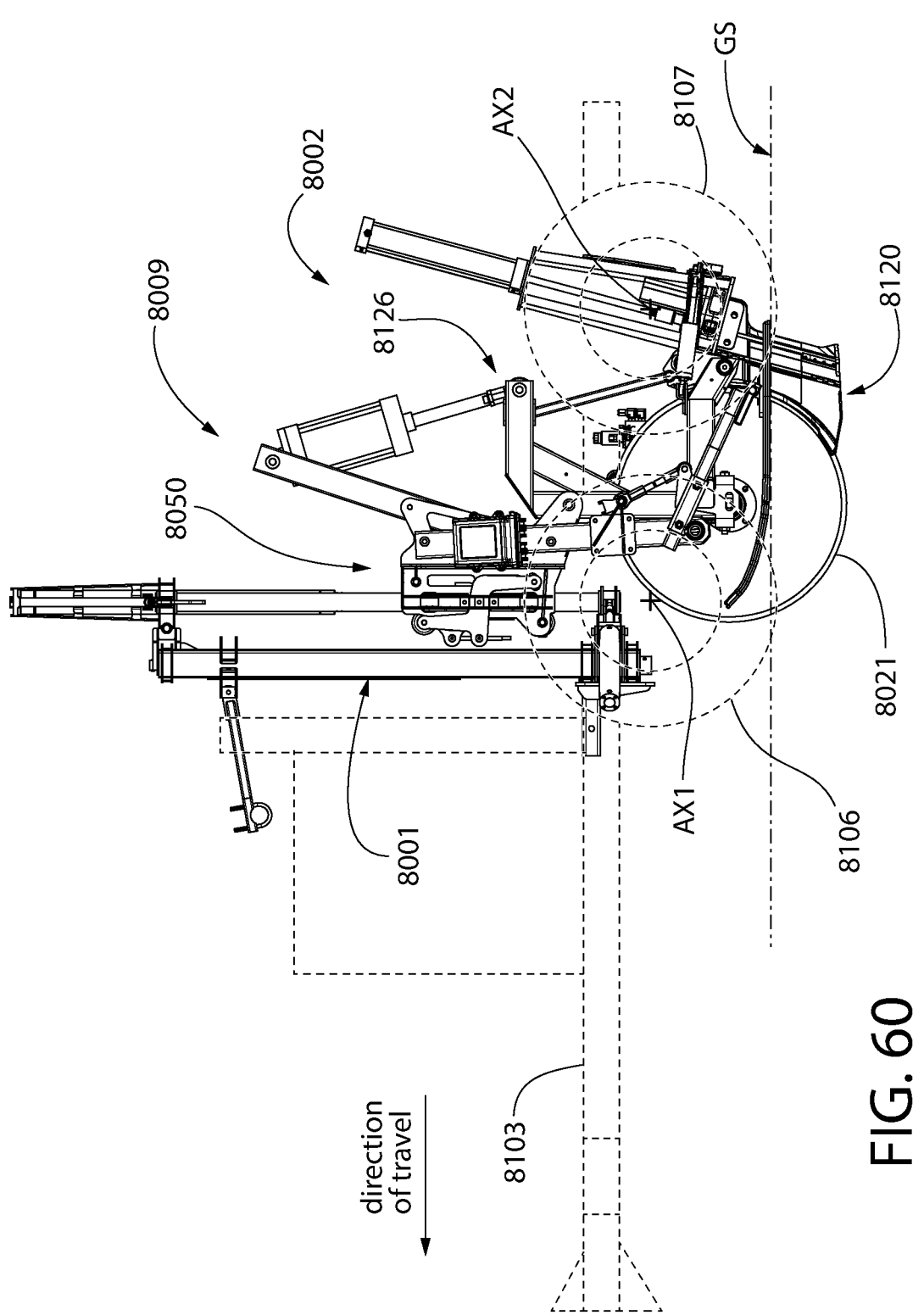
FIG. 60 is side view thereof but showing the soil sample collection apparatus.
Figure 61:
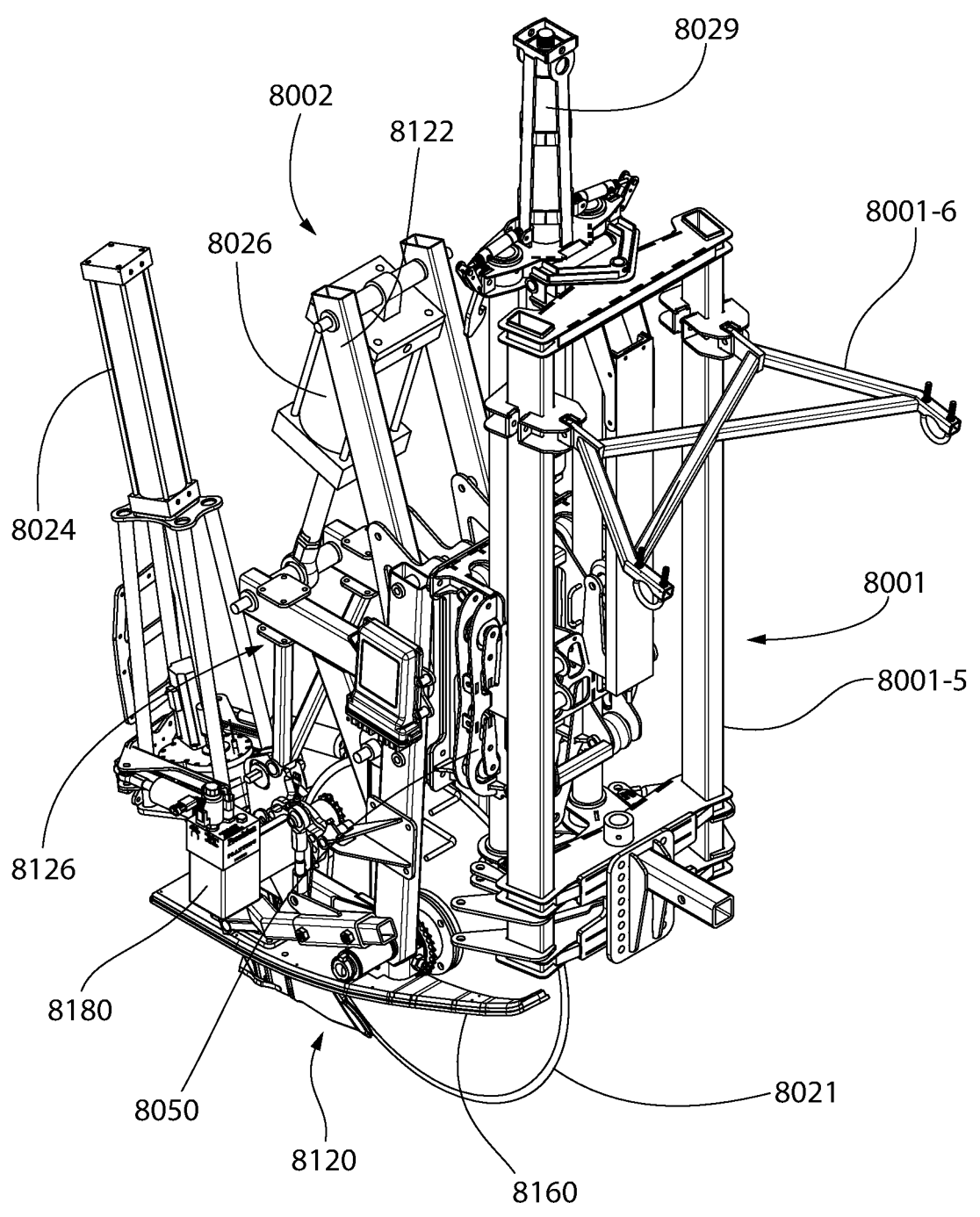
FIG. 61 is a top front perspective view of the sample collection apparatus of FIG. 60.
Figure 62:
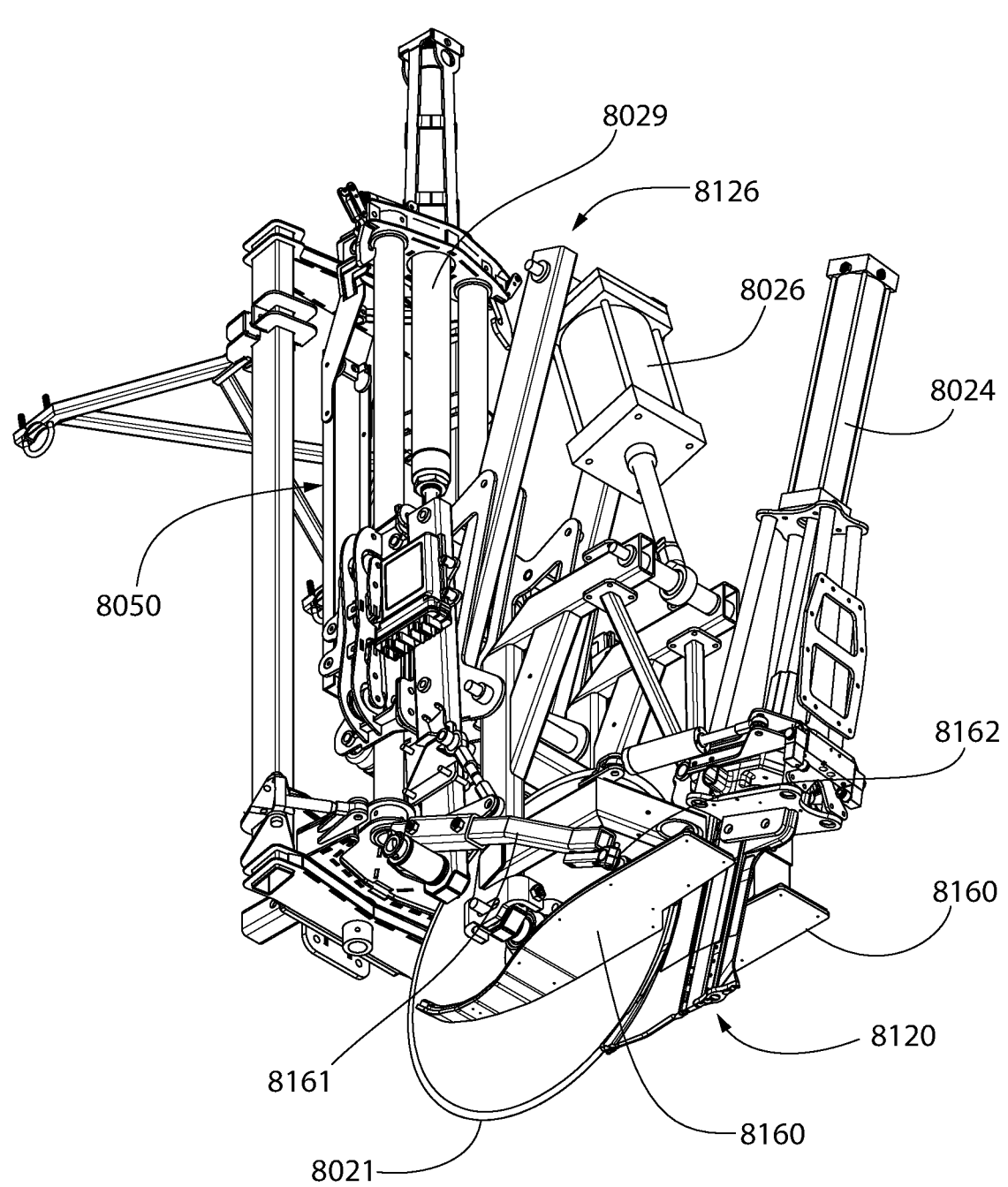
FIG. 62 is a rear bottom perspective view thereof.
Figure 63:
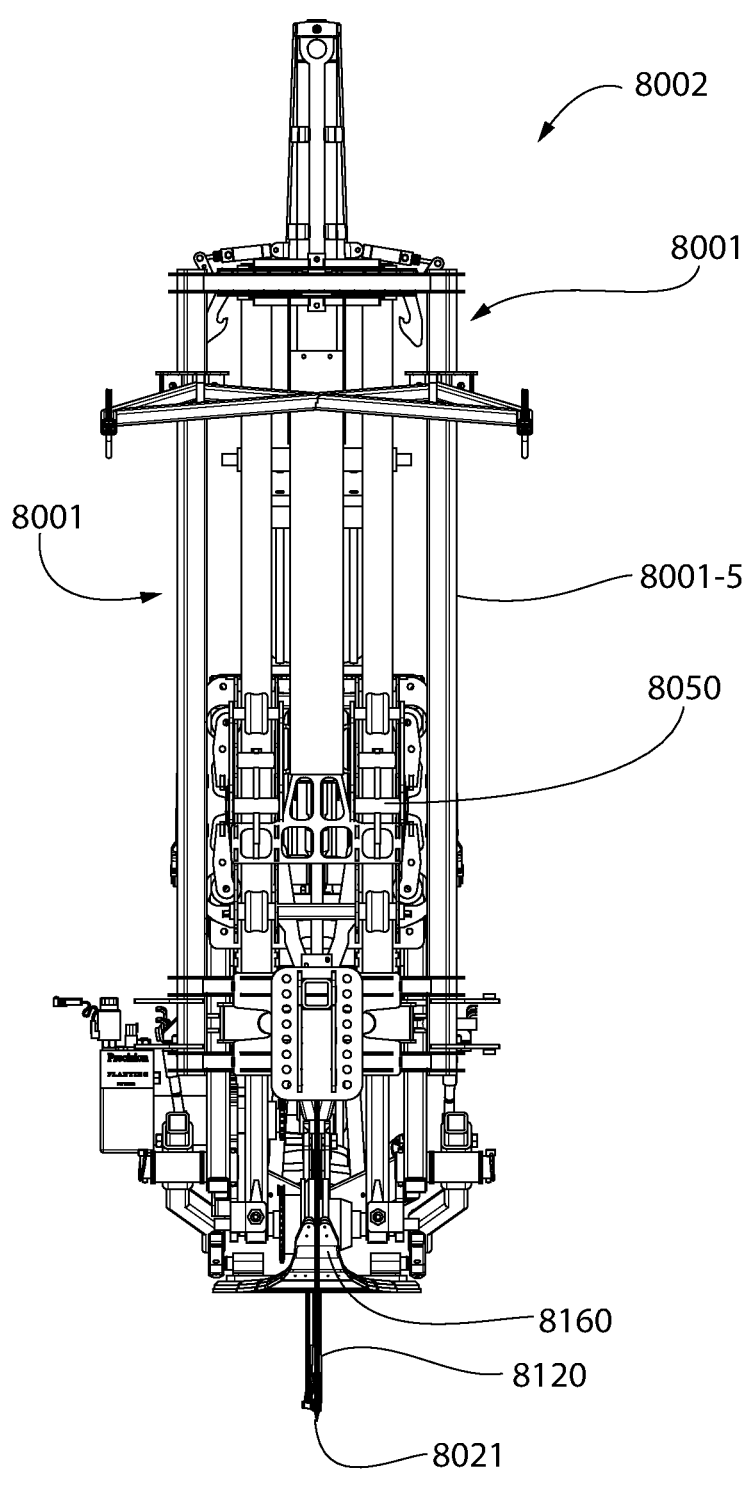
FIG. 63 is a front view thereof.
Figure 64:
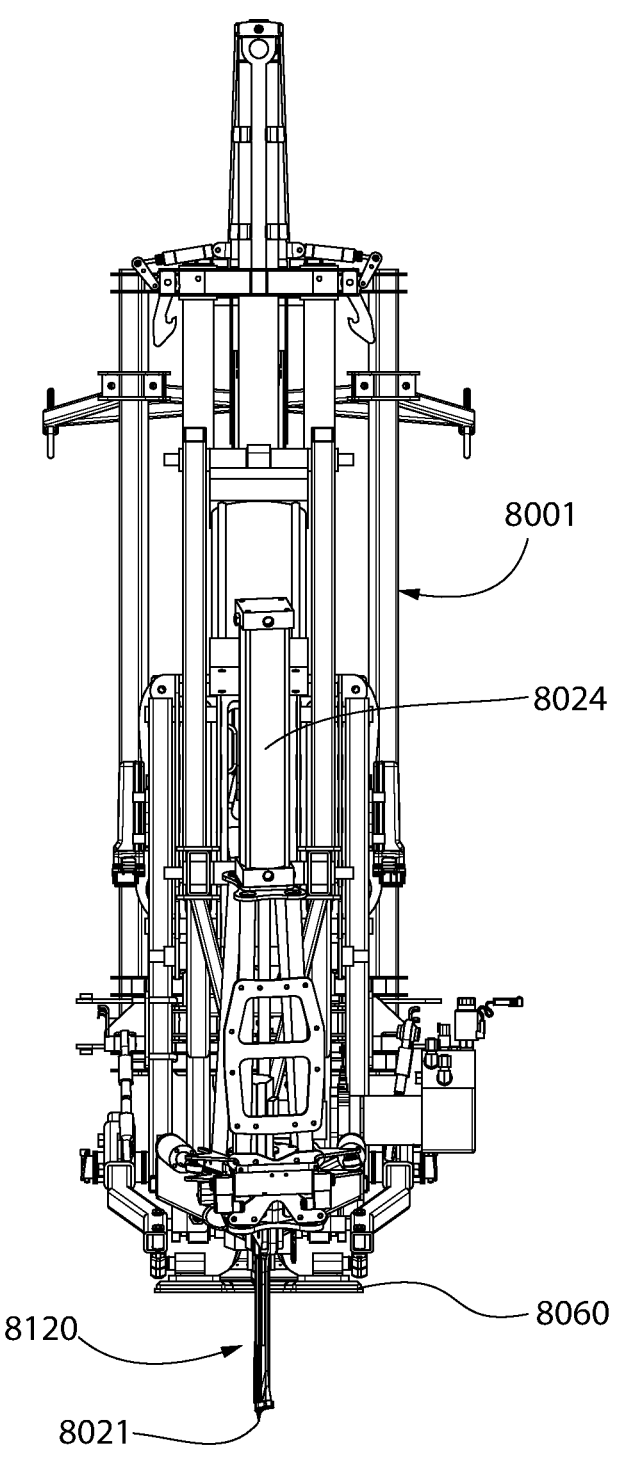
FIG. 64 is a rear view thereof.
Figure 65:
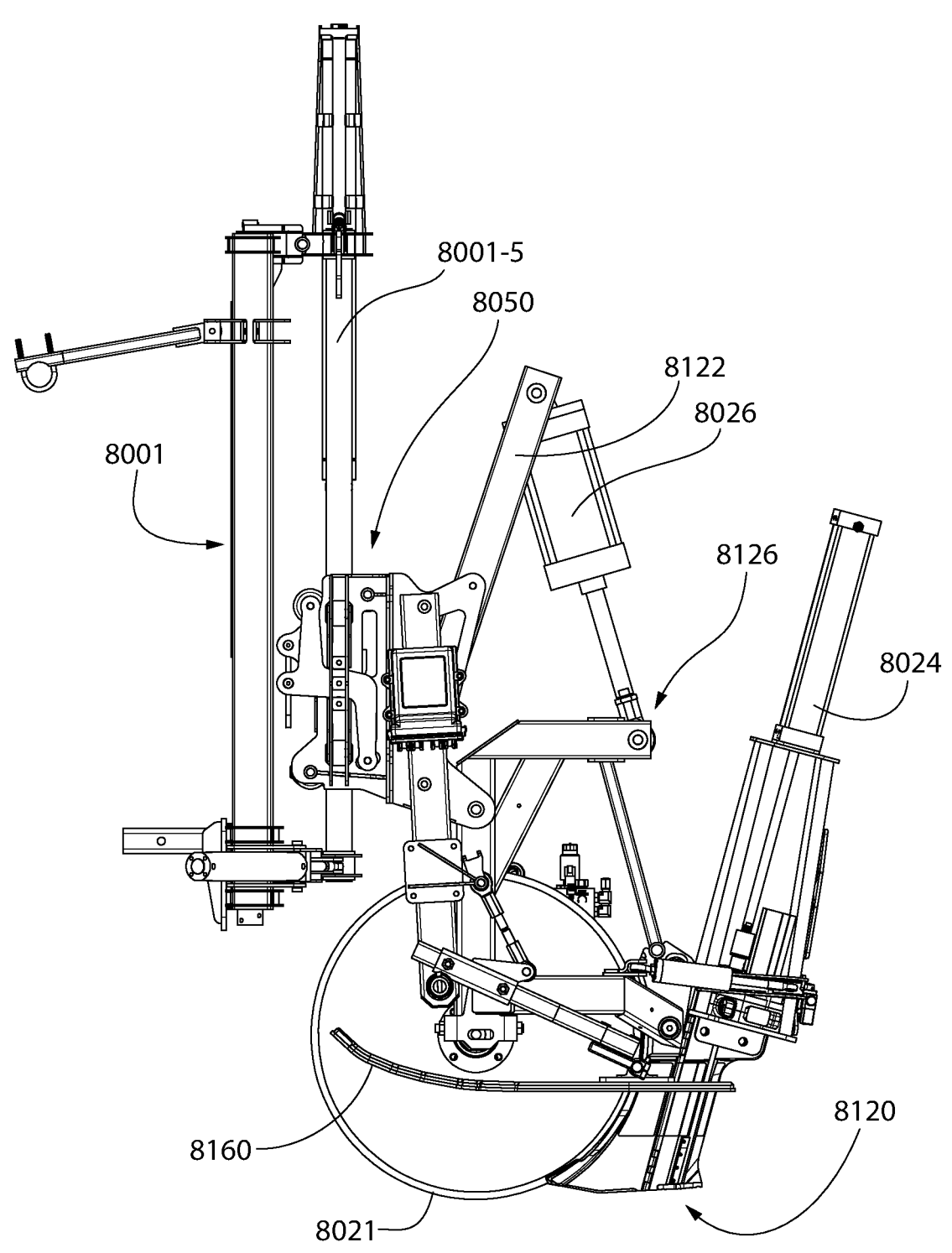
FIG. 65 is a right side view thereof.
Figure 66:
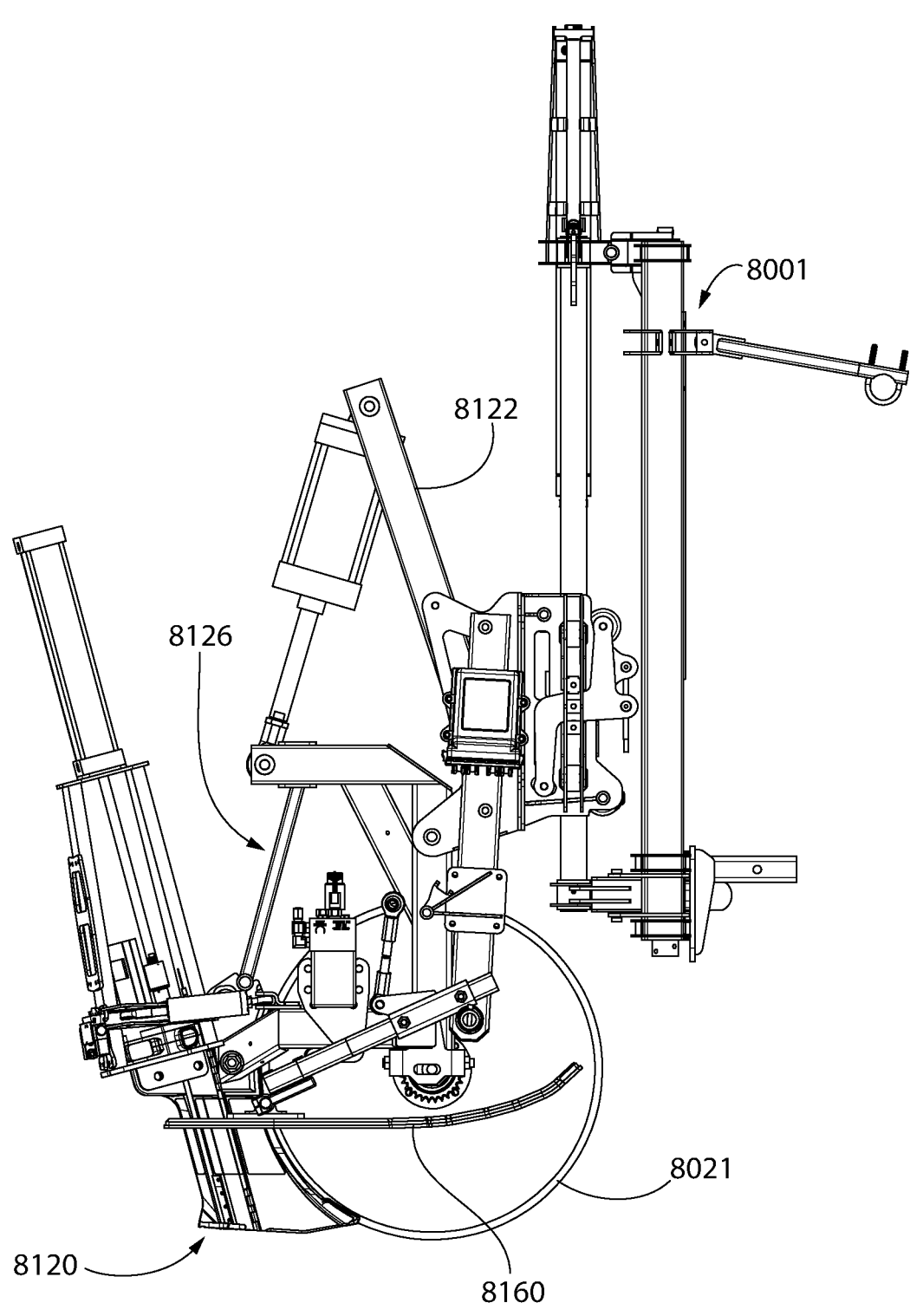
FIG. 66 is a left side view thereof.
Figure 67:
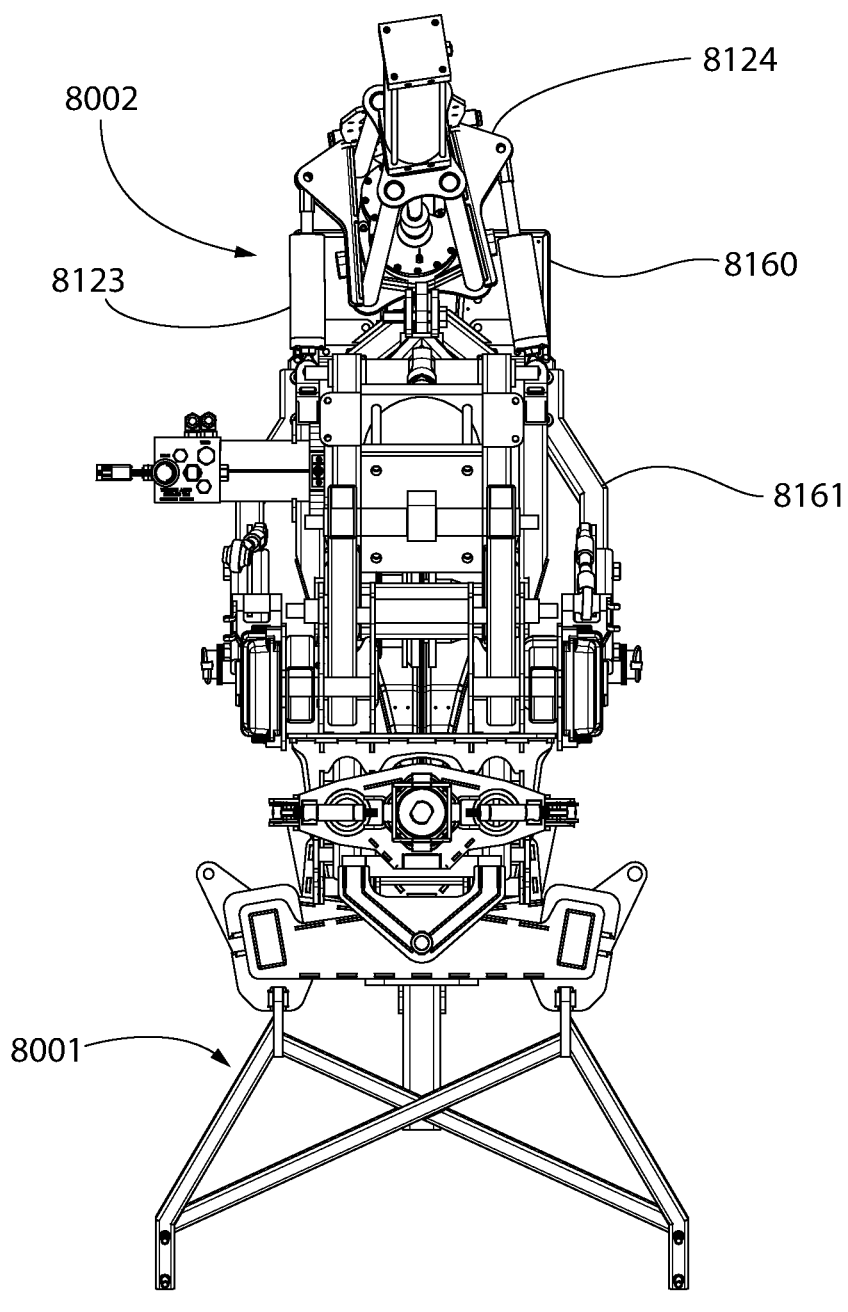
FIG. 67 is a top view thereof.
Figure 68:
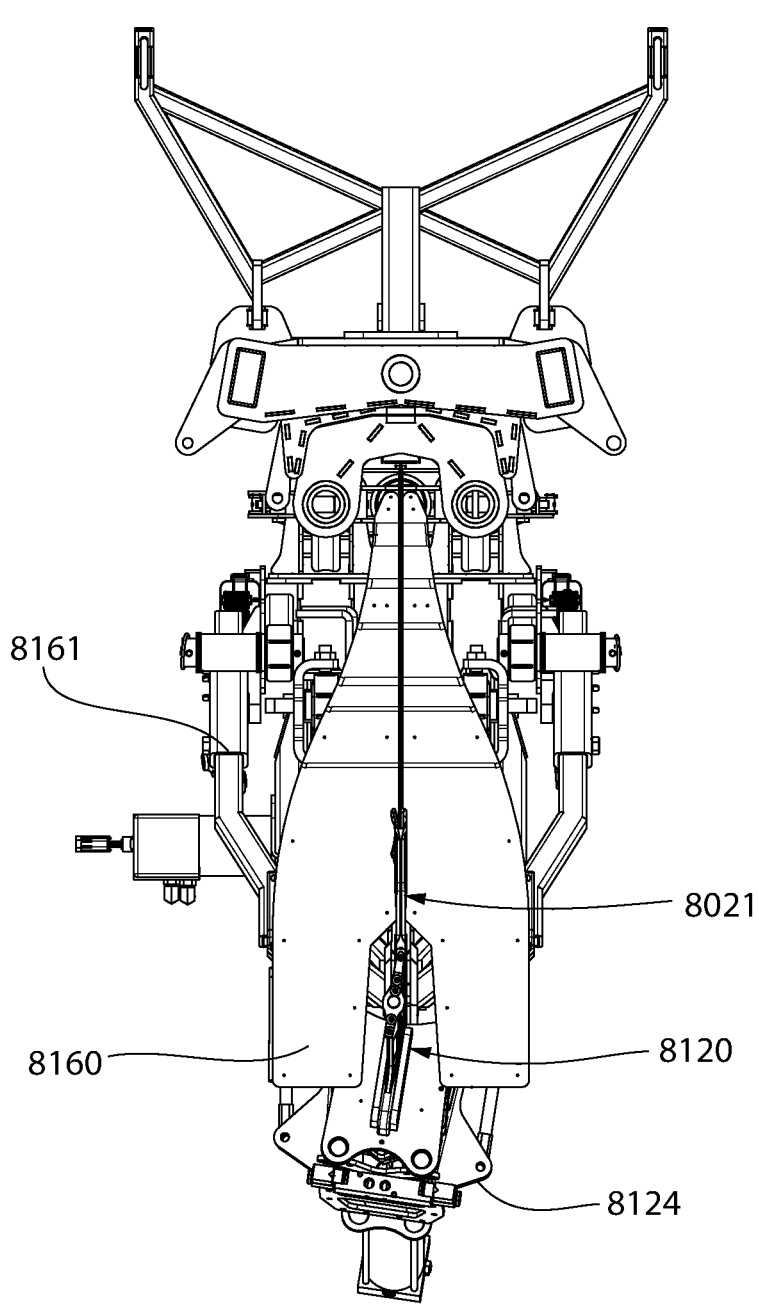
FIG. 68 is a bottom view thereof.

FIG. 60 shows the mounting position of the soil sample collection apparatus 8002 relative to the frame 8103 of the sample collection trailer 8100. The coulter blade 8021 which first encounters the soil as trailer 8100 traverses agricultural field AF is preferably positioned between the wheels 8106, 8107 to compensate for undulations in the soil surface GS encountered in the field when sampling. More specifically, coulter blade 8021 is positioned between transverse wheel axes AX1 and AX2. In addition, knife assembly 8020 which trails the coulter blade may also preferably be positioned between the wheel axes. As shown, this arrangement advantageously optimizes the sample collection equipment geometry for collecting samples in rougher undulating field topography as shown in FIG. 59. Because this collection equipment is supported between the front and rear wheels 8106 (as opposed to in front of or rearward of the wheels), the equipment remains stable and engaged with the soil as the wheels ride up or down in the hills or valleys in the soil surface GS. The coulter blade 8021 and sample collection knife assembly 8020 are further laterally stabilized between the four wheels 8106, 8107.

FIGS. 61-78 depict soil sample collection assembly 8009 with various modifications and alternative embodiments of the soil sample collection system 8000 components previously described herein. Some of these alternative component designs include guide ski 8160 and a pivotably rudder action soil sample collection knife assembly 8120. These and other alternative embodiments of the sample collection system are described below.

According to another aspect of the soil sample collection system 8000, the guide ski 8060 which rides on the soil surface GS as previously described herein may be specially configured to provide additional functionality. The reconfigured alternative guide ski embodiment, which appears variously throughout FIGS. 61-78, is designated 8160. Guide ski 8106 performs one function similarly to original guide ski 8060 (shown in FIGS. 5, 6, 8, 9, 16, and 17) which is to limit the insertion depth of the coulter blade 8021 and sample collection knife assembly 8020 in the soil.

In another function, the guide ski 8106 is configured and operable to maintain downward pressure on the soil passing along each side of the coulter blade 8021. This advantageously maintains contact of the knife assembly 8020 with the soil displaced by the coulter blade in forming the furrow in agricultural field AF for positive collection of the soil samples. Without the presence of the skis, the inventors have found that the coulter blade tends to cause the soil to be displaced and pushed upward and outward away from the collection cavity of the knife assembly which trails the coulter blade when the soil sample collection apparatus 8002 is pulled through the soil. In one embodiment, one guide ski 8106 is preferably provided on each of the two lateral sides of the coulter blade 8021 for the foregoing purpose (see, e.g. FIG. 78). Each guide ski 8160 is pivotably movable and mounted to support frame 8001 or carriage 8050 attached thereto via cylindrical mounting boss 8062 on the ski and mechanical linkage 8161. Boss 8062 defines the pivot axis of each ski.

Figure 69:
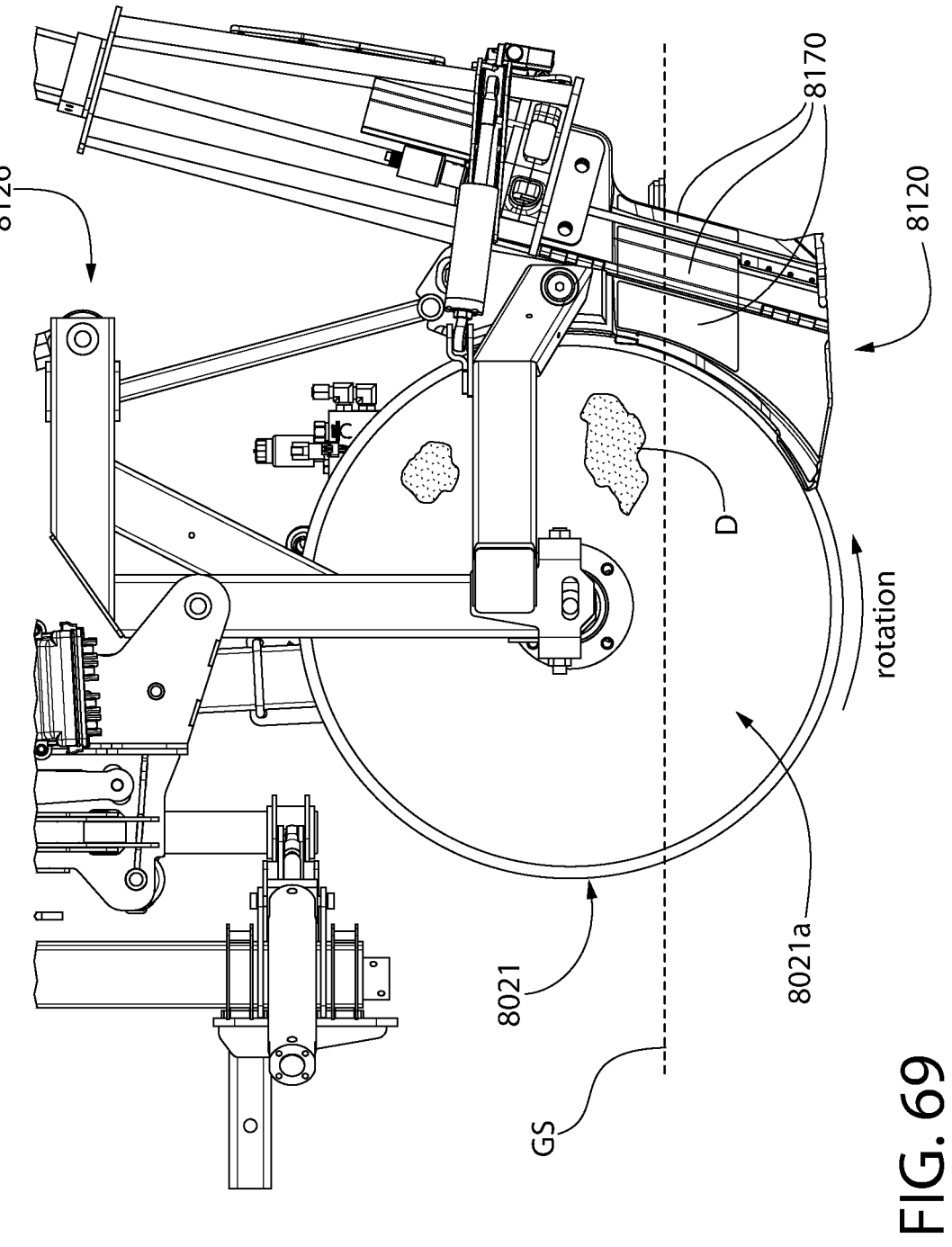
FIG. 69 is a partial side view thereof showing soil deposits adhered to the coulter blade.
Figure 70:
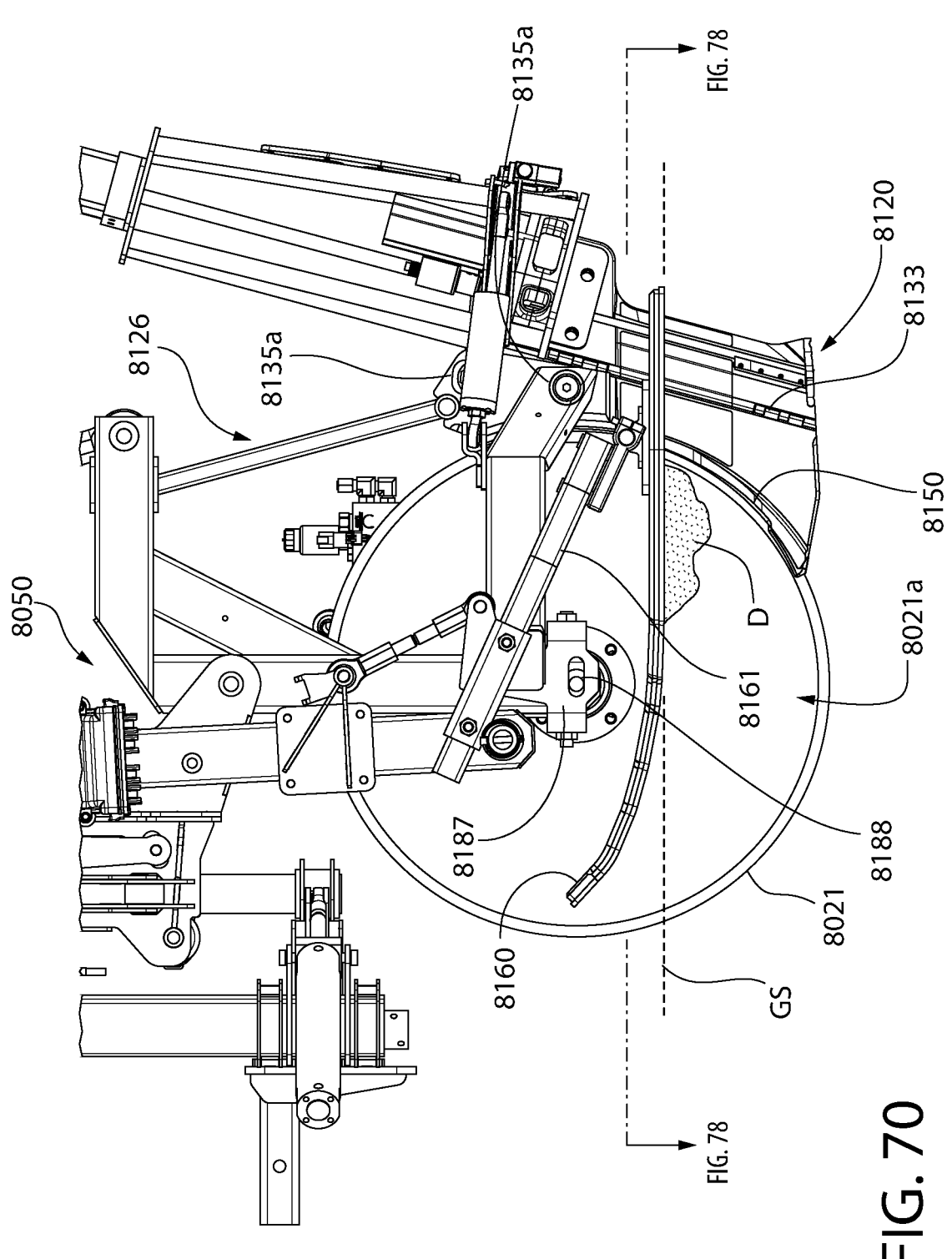
FIG. 70 is a partial side view thereof similar to FIG. 69 but showing guide skis operable to remove the soil deposits from the coulter blade.

Functionally, Guide skis 8160 are further configured and arranged to aid in wiping and cleaning field soil deposits D off of the major lateral side surfaces 8020a of the coulter blade 8021 (see, e.g. FIGS. 69-70). The inventors have discovered that field soil tends to adhere to these surfaces as the blade is pulled through the soil and rotates about it rotational axis, thereby carrying the soil deposits with it upwards on the back side of the blade rotation. Soil deposits on coulter blade 8021 can disrupt proper operation of the soil engaging elements (coulter blade and knife assembly 8020) and ability to collection soil samples. Accordingly, the guide skis 8160 are preferably disposed adjacent to the lateral side surfaces of the coulter blade 8021 and separated therefrom by as small a space or gap G1 as practicable for wiping the blade substantially clean with each rotation (see, e.g. FIG. 78). In preferred but non-limiting embodiments, gap G1 may fall in a range less than the thickness T1 of coulter blade 8021 (measured between the major side surfaces 8021a) and no more than five times, or alternatively twice, T1 for effecting wiping of the soil deposits D from the coulter blade. In one embodiment, G1 is less than or equal to T1. FIG. 69 shows the adherence and presence of soil deposits D on coulter blade 8021 with the presence of guide skis 8160 (note deposits rotate upward beyond the ground or soil surface GS). With the skis in place and located proximate to each side of coulter blade 8021 as shown in FIG. 70, the soil deposits D are wiped off of the coulter blade as rotates upwards to engage the adhered deposits with the underside of the skis 8160. Soil deposits above soil surface GS are eliminated and removed as shown.

Figure 71:
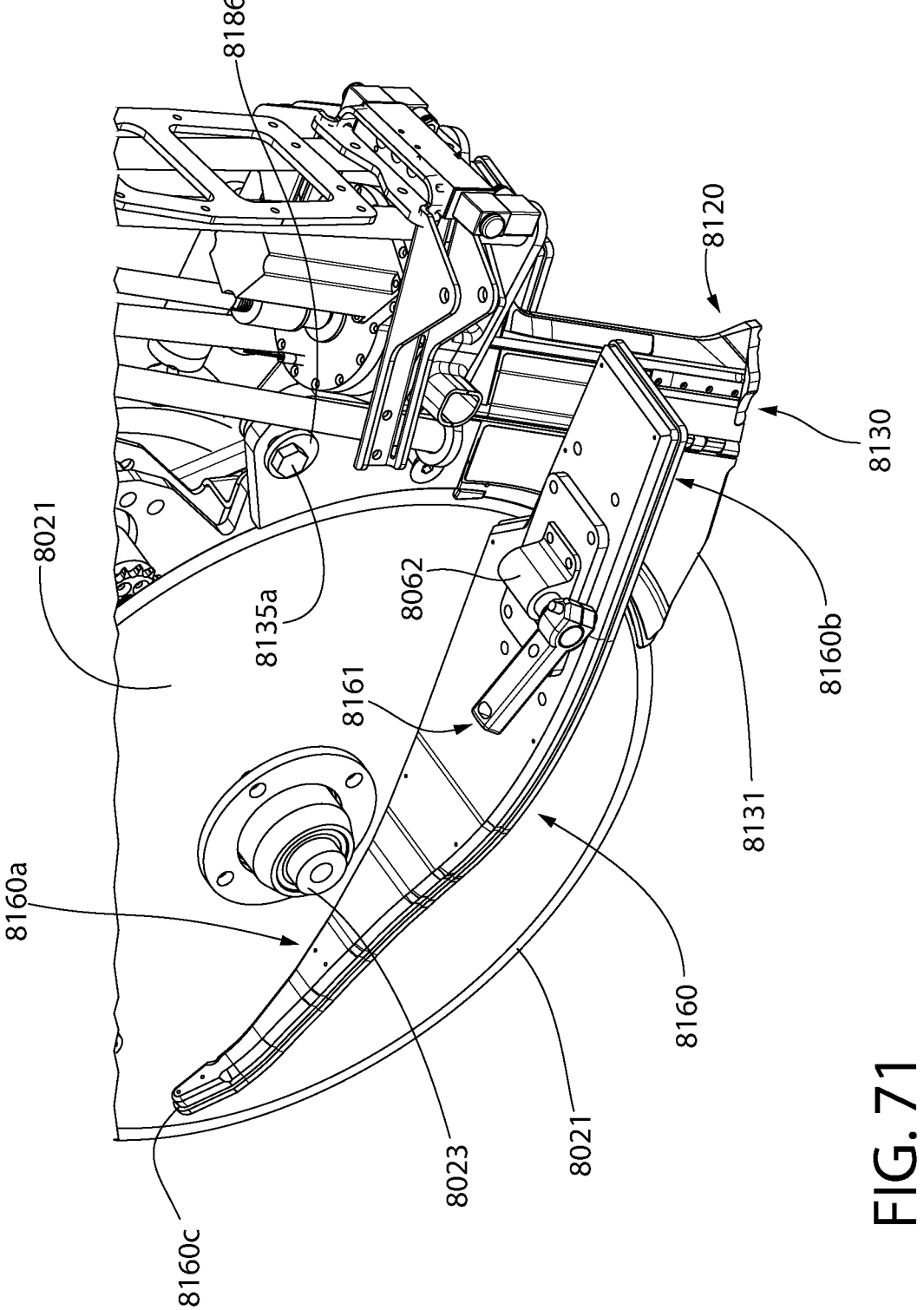
FIG. 71 is a partial top rear perspective view of the sample collection apparatus.

The geometry or configuration of alternative guide ski 8160 is designed to deflect obstructions in the soil away from the coulter blade 8021 and knife assembly 8020, as well as provide a "lead in" to changing terrain topography in agricultural field AF during sample collection. Examples of such disruptive obstructions may include past crop residue, fallen branches, rocks, etc. In one embodiment, ski 8160 has a wedge-shaped front end portion 8160a and laterally broadened rear end portion 8160b as shown in FIG. 71 for example. Accordingly, ski 8160 becomes gradually widened in the lateral width moving from the front end portion towards the rear end portion. Front end portion 8160a is also upwardly turned or curved in one embodiment to prevent the leading tip 8160c from becoming embedded in the soil during sample collection as the sample collection trailer 8100 traverses the agricultural field.

Figure 72:
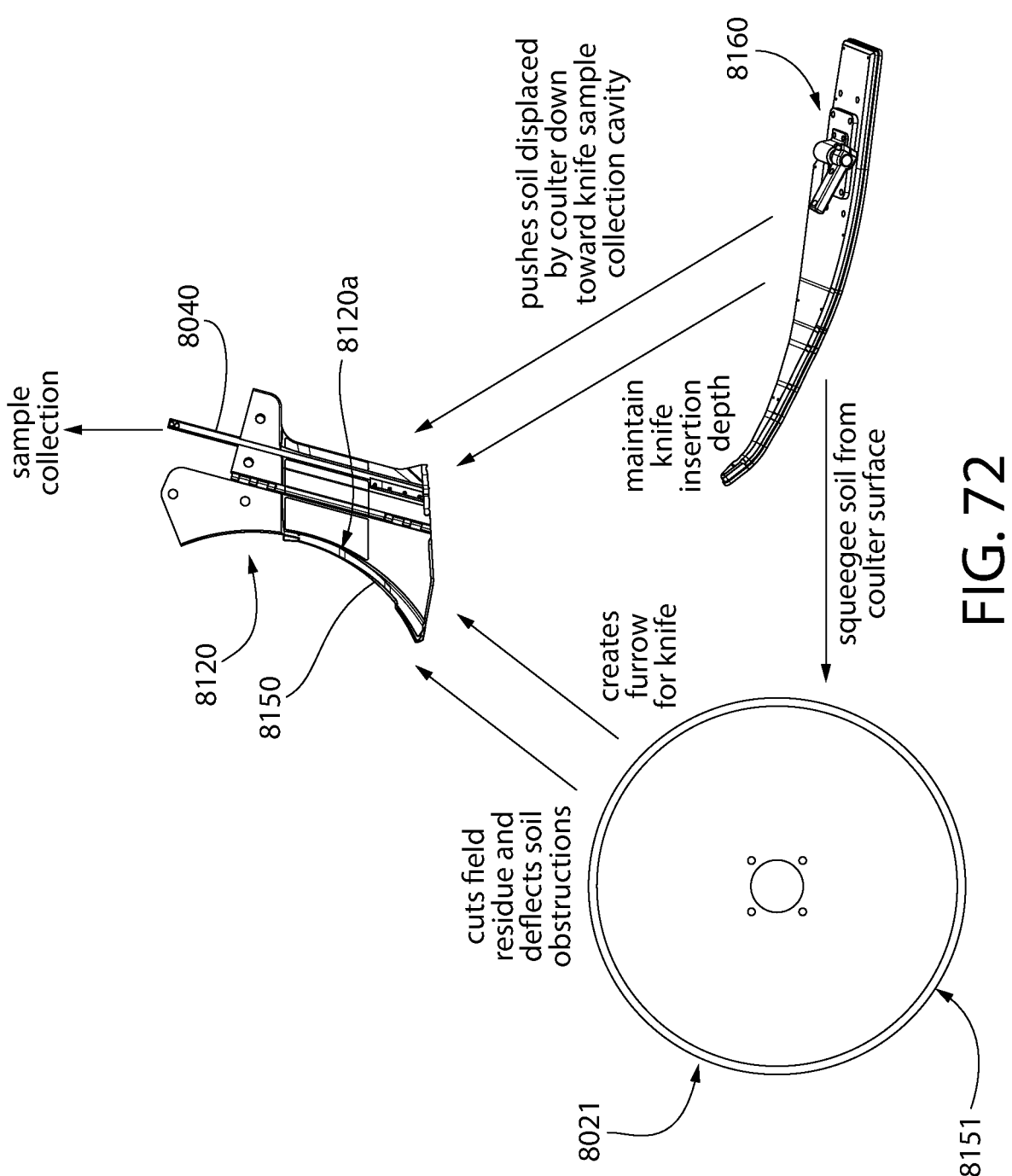
FIG. 72 is an exploded view of the coulter blade, sample collection knife assembly, and guide ski illustrating the functional interrelationships thereof.
Figure 73:
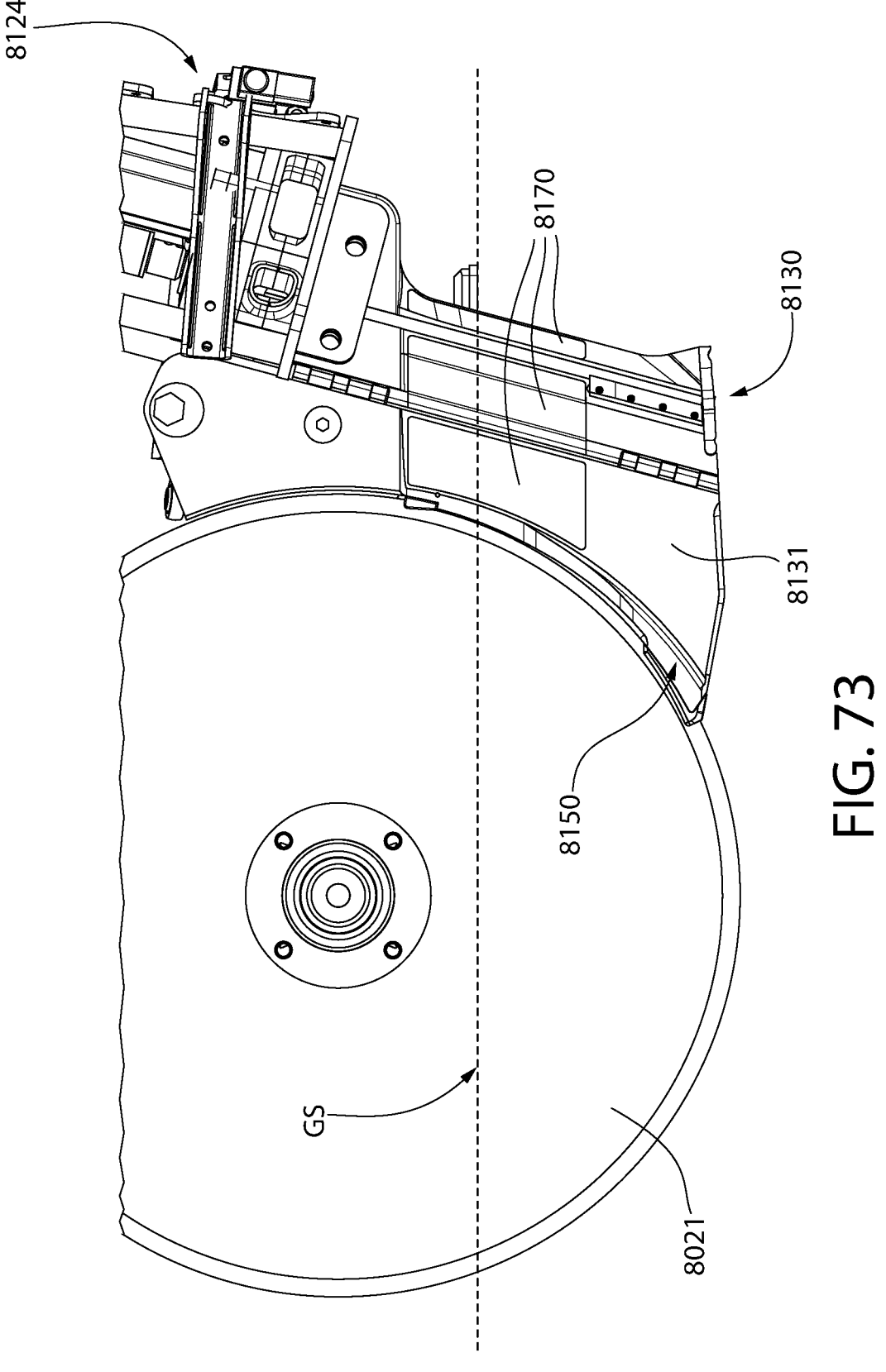
FIG. 73 is an enlarged side view of the coulter blade and knife assembly.

FIG. 72 graphically summarizes and illustrates the functional relationships of the ground engaging elements of the soil sample collection apparatus 8002 (i.e. coulter blade 8021, knife assembly 8120, and guide skis 8160).

According to another aspect of the soil sample collection system 8000, an alternative embodiment of knife assembly 8120 is configured and operable to provide rudder action. This allows the operator or system controller to laterally pivot and angle the rear soil collecting portion of the knife assembly outwards in either lateral direction. This advantageously enhances capture of the soil sample by allowing direct impingement of the soil into the laterally open collection cavity 8042 of the knife's collection spool 8040 as the knife assembly 8120 is pulled through the soil.

It bears noting that it is important to maintain positive control over soil collection with the collection spool housed within the knife. Even though the knife is passing through the soil, this does not ensure that there is positive contact between the soil trench or furrow wall created by the coulter blade 8021 and the collection spool to capture the soil sample when intended. One method of positively controlling soil-to-spool contact is by providing a pivotable rudder portion on the knife assembly 8120 and placing the soil sample collection spool within that rudder as disclosed herein.

Referring now in general initially to FIGS. 70-85, the rudder-action knife assembly 8120 is generally similar to the stationary non-angularly adjustable version knife assembly 8020 previously described herein in overall configuration, with exception for provisions which allow the angular pivotable action noted above. Angularly adjustable knife assembly 8120 generally includes stationary front blade element 8131 and rear blade element 8130 pivotably coupled to the front blade element. Soil sample collection spool 8040 is movably disposed in the rear blade element 8120 and is rotatable and vertically movable for capturing the sample using the same mechanisms previously described herein associated with knife assembly 8020 (e.g., spool positioning actuator 8024 and knife positioning actuator 8026). Front blade element 8131 defines front leading edge 8120a of the knife assembly.

Figure 80:
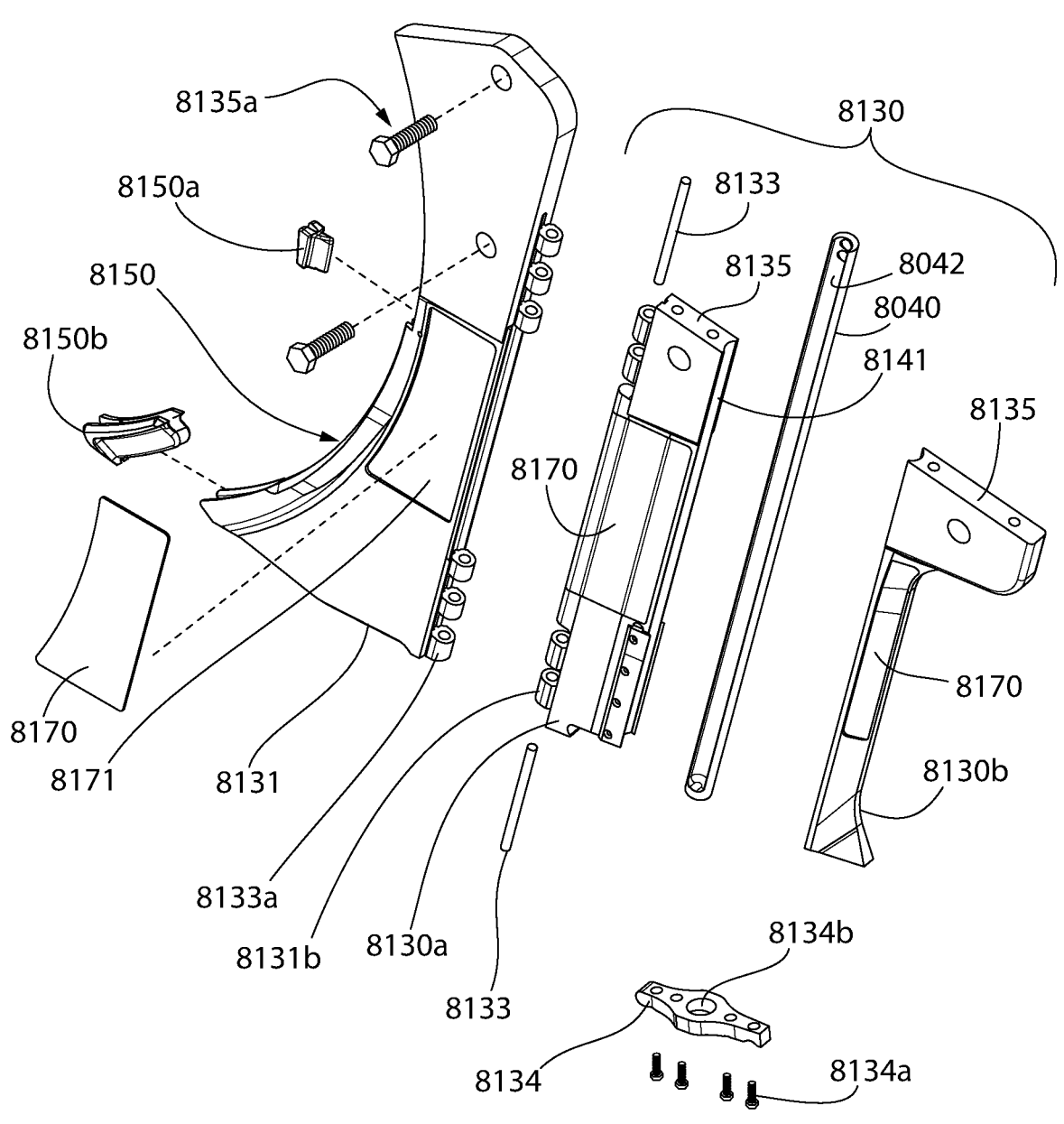
FIG. 80 is a first exploded perspective view of the knife assembly.
Figure 81:
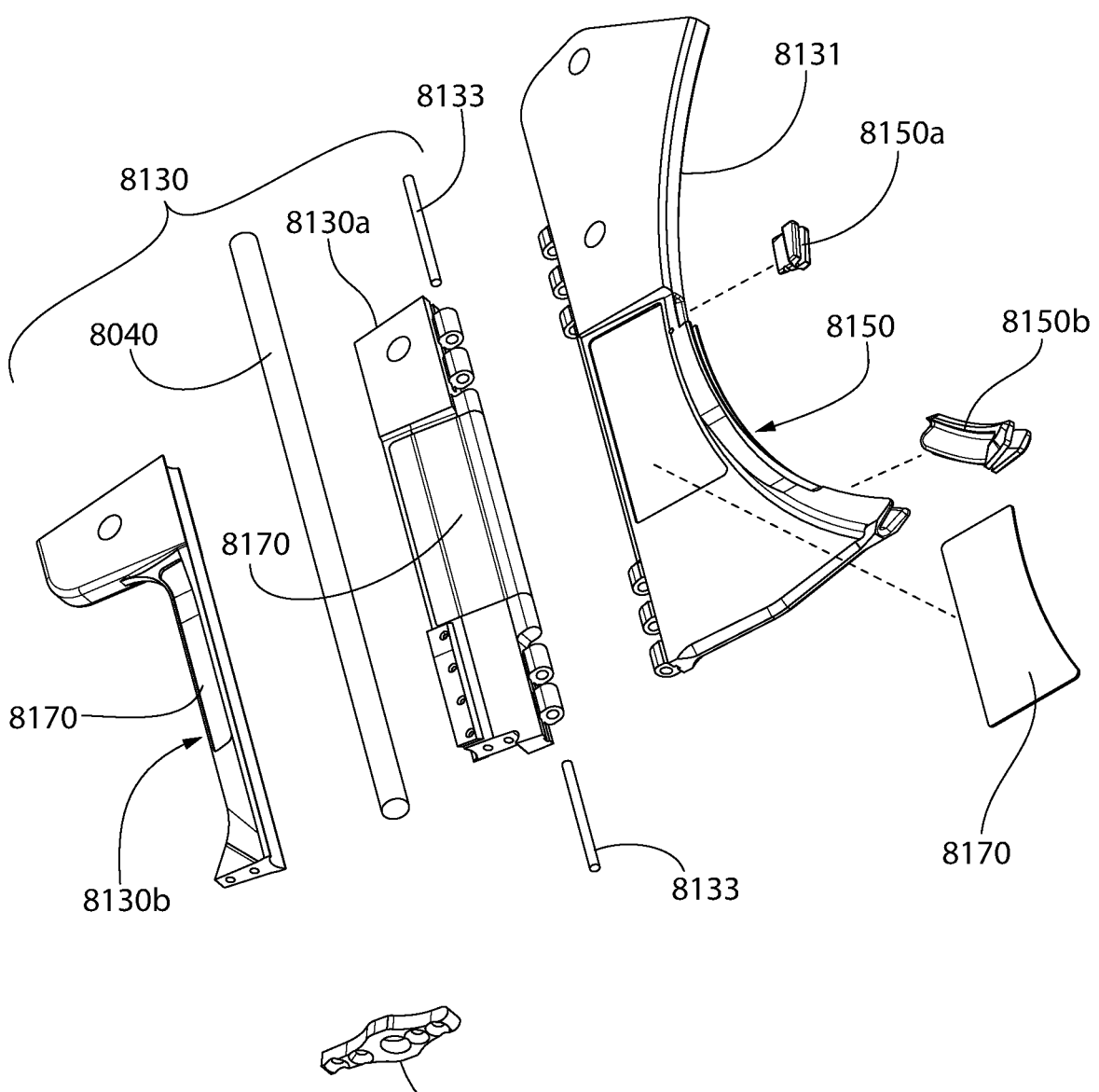
FIG. 81 is a second exploded perspective view of the knife assembly.
Figure 82:
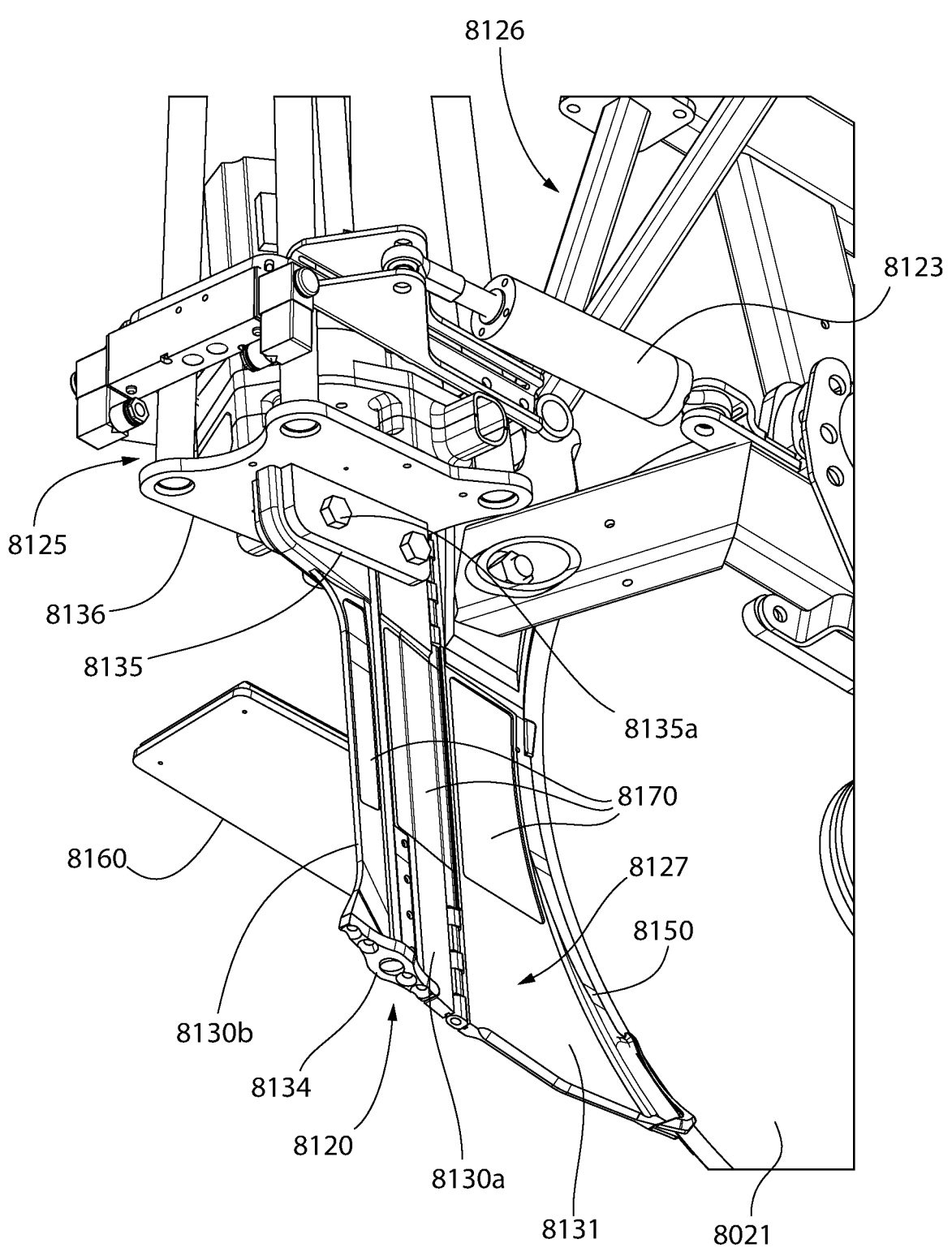
FIG. 82 is a first bottom rear perspective view of the collection apparatus showing the mounting details of the pivotable rear blade of the knife assembly.
Figure 83:
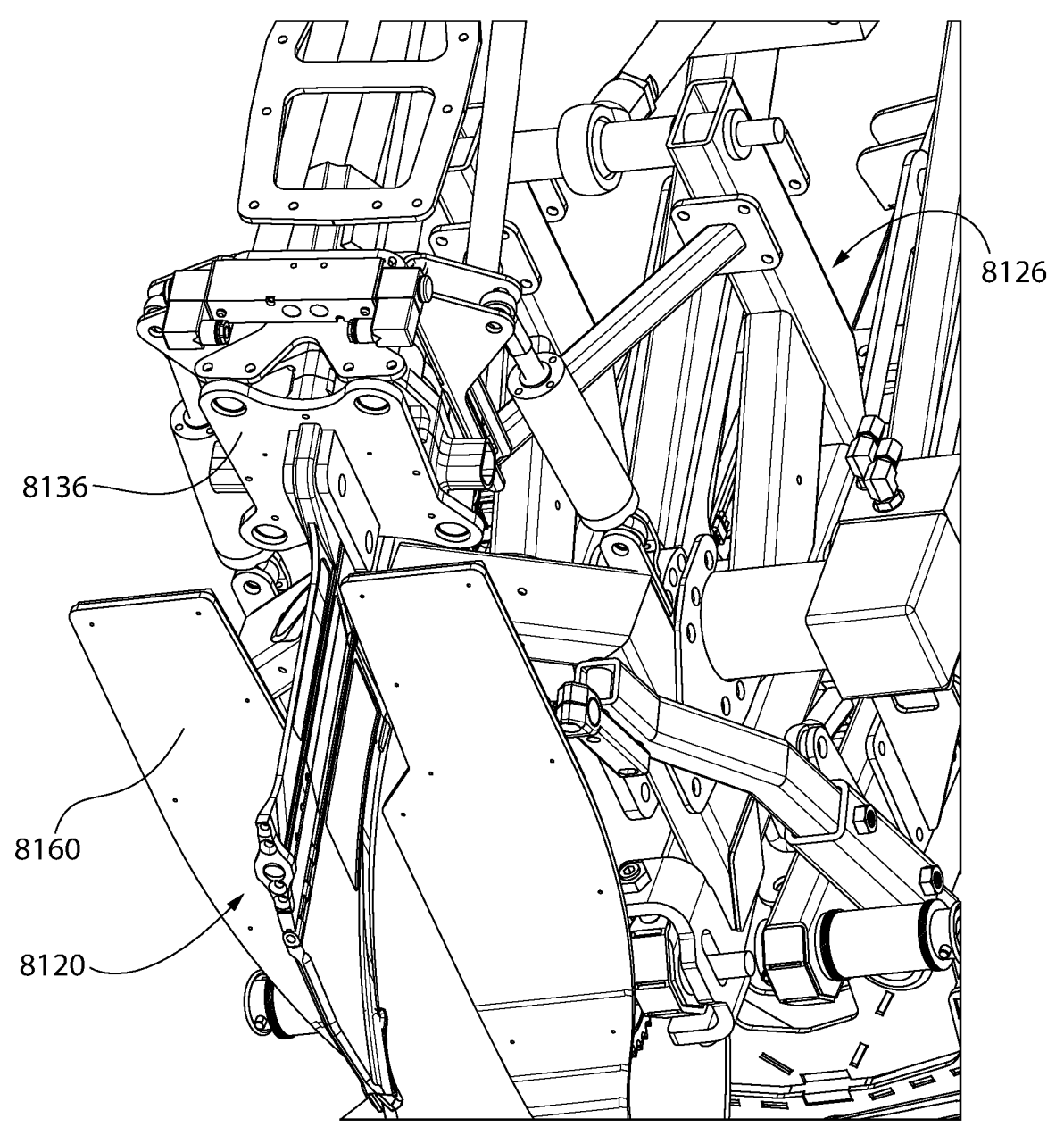
FIG. 83 is a second bottom rear perspective view thereof.

The upper mounting portion of vertically elongated front blade element 8131 is coupled to swingarm frame 8126 of the vertically slideable carriage 8050 via top and bottom bolts 8135a (see, e.g., FIGS. 70, 71, and 80). This maintains the front blade element in axial alignment with horizontal axis HA and the direction of travel at all times. The bottom bolt 8135a may act as pivot for the front blade element and top bolt 8135a assemblage which includes a cam washer 8186 captured by the blade element. The front blade elements 8131 and entire knife assembly 8120 is pivotably and angularly moveable about the pivot axis of the lower bolt which together allows for manual angular adjustment of the knife assembly 8120 relative to the soil and horizontal axis HA of the collection apparatus 8002.

Fore and aft adjustment (i.e. axially forward and rearward) of the knife assembly 8120 is provided by a horizontal adjustment slot 8188 formed in the coulter blade hub support bracket 8187 (see, e.g., FIG. 70). This allows the axial horizontal insertion depth of the coulter blade 8021 into the recess 8152 of the blade guide element 8150 (further described herein) on the knife assembly to be adjusted to achieve a proper fit which minimizes incursion of debris such as crop residue between the blade and knife assembly 8021, as described elsewhere herein.

Rear blade element 8130 may be an assemblage including a vertically elongated forward blade segment 8130a, vertically elongated rearward blade segment 8130b, and bottom base plate 8134 (see, e.g., FIGS. 80-85). Base plate 8134 may be horizontally elongated and attached to the bottoms of each of the forward and rearward blade segments via threaded fasteners 8134a. A central mounting hole 8134b in the baseplate receives and stabilizes the bottom end of the cylindrical sample collection spool 8040.

The forward and rearward blade segments 8130a and 8130b may be mounted to the base plate in a horizontally axially spaced apart manner along horizontal axis HA of the collection apparatus on opposite sides of central mounting hole 8134b. This spaced mounting arrangement collectively defines a vertically elongated spool slot 8141 between the blade segments 8130a, 8130b in which sample collection spool 8040 is movable positioned for rotational and very movement therein during the soil collection process. Accordingly, each blade segments having opposing and facing vertically-extending concavity which contribute to formation of slot 8141.

Spool slot 8141 has a transverse cross-sectional shape complementary configured to the cross-sectional shape of the spool 8040, which may be circular in one embodiment. Similarly to spool slot 8041 previously described herein, the present spool slot 8141 functions in a similar manner and is configured to rotatably and slideably receive the spool 8040 therein. Specifically, spool 8040 is vertically and slideably movable upwards/downwards in the slot 8141, and rotatably movable as well for capturing and retaining the soil sample as further described herein. Both the slot 8141 and spool 8040 may have circular shapes in transverse cross-section as the spool may have a cylindrical configuration in the illustrated embodiment.

Referring to FIGS. 80-84, each of the forward and rearward blade segments 8130a and 8130b has an upper mounting portion 8135 configured for detachable coupling to a U-shaped clevis 8135 which is rigidly attached to the underside of pivoting blade mounting plate 8136 of the pivotable blade support structure 8125. A pair of bolts 8135b may be used to couple the blade segments to clevis 8135 in one embodiment. Other means of coupling including welding may be used in other embodiments.

To provide the rudder action noted above, rear blade element 8130 is pivotably coupled to front blade element 8131 via at least one elongated hinge pin 8133. In the illustrated embodiment, two hinge pins comprising an upper and lower pin are provided. Hinge pin 8133 extends through hinge barrels 8133a disposed on the rear side of front blade element 8131 and hinge barrels 8133a disposed on the front side of rear blade element 8130 collectively forming a hinged joint. Hinge pin 8133 defines a substantially vertical pivot axis about which the rear blade element can be laterally pivoted relative to the fixed front blade element 8131. The term "substantially" as used here connotes that the pivot axis and hinge pins 8133 may not be exactly vertical in orientation as shown in FIG. 70, but may be considered closer to vertical than horizontal. The front blade element is rigidly coupled to vertically slideable carriage 8050 via swingarm 8126 which raises or lowers the soil sample collection apparatus 8002 in the manner previously described herein. Front blade element 8131 remains stationary relative to the carriage, whereas rear blade element 8130 is pivotable relative to the front blade element and carriage capture the soil sample.

The knife assembly 8120 pivotable action in one embodiment is operated by a pair of external rudder actuators 8123 configured to provide the ability for the "ruddering" rear blade element 8130 to free float (angularly unlocked), lock left in angular position, lock right in angular position, or lock axially inline with front blade element 8131 in angular position as needed. When not collecting soil samples, the rear blade element may be allowed to free float (unlocked in angular position) or be locked in the axially inline position, either of which maintains smooth unbiased travel of the rear blade element through the soil. There is minimal or no laterally acting inward soil pressure forces imparted to the rear blade element 8130 in the free floating or axially locked position which advantageously minimizes the force required for the sampling vehicle to pull the collection apparatus 8002 through the soil.

When spool collection is initiated by controller 2820 or manually either on the left or right side of knife assembly 8120, the rudder-like rear blade element 8130 may be pivoted by rudder actuators 8123 either left or right as appropriate to force the collection spool 8040 into the soil trench or furrow wall created by the leading coulter blade 8021 for filling the collection cavity 8042 of the spool with soil to capture the sample. The rear blade element 8130 can then be returned to the inline centered free float position or axially locked position when sample collection is complete.

Rudder actuator 8123 may be a pneumatic piston cylinder type actuator in one embodiment; however, hydraulic piston cylinders or electric linear actuators may also be used. Actuators 8123 are each configured to act in a linear direction via movable operating or piston rod 8123-1 which is extendible or retractable into cylinder 8123-2. Actuators 8123 may be coupled at one end (e.g., piston rod 8123-1) to mounting flanges 8124 of a laterally/horizontally pivotable rudder support structure 8125 and at an opposite end (e.g., cylinder 8123-2) to the swingarm frame 8126 coupled to the vertically movable carriage 8050 (or intermediate structural members coupled thereto). This mounting arrangement of the cylinder and piston rod may be reversed in other embodiments. Support structure 8125 may be pivotably connect to one of the pivot pins 8133 of the knife assembly 8120 in one embodiment, or a separate pivot pin which defines a vertical pivot axis. Rear blade element 8130 ("rudder") a top is rigidly mounted in turn to support structure 8125 such that there may be no relative movement therebetween. Pivoting blade support structure 8125 left or right via operation of actuators 8123 in turn imparts the same pivotable movement to the rudder. Actuators 8123 may be controlled by system controller 2820 or manually operated.

It bears noting that pivotal force and motion created by rudder actuators 8123 may be delivered with a prescribed angular displacement or force from actuation. "Ruddering" the knife assembly 8120 with a positive force into the walls of the trough or furrow created by coulter blade 8021 maintains adaptability for sampling a wide variety of different soil types. For example, a harder/denser soil type may not allow the rear blade element 8130 which collects the soil sample via collection spool 8040 to move angularly to a great degree, but large angular displacement of the blade element should not be necessary for sample collection in such difficult soils. Conversely, a softer soil will allow for greater displacement of the rear blade element which may be required for adequate contact with the soil to collect a proper soil sample. Accordingly, the rudder action knife assembly 8120 advantageously provides considerable versatility for soil sampling in agricultural fields comprised of numerous soil types.

According to another aspect of the soil sample collection system 8000, the forward leading edge of knife assembly 8120 may also include at least one blade guide feature or element 8150 which receives the circumferential cutting edge 8151 of the rotating coulter blade 8021 partially therein. FIGS. 72-79 and 80-82 variously show the blade guide element 8150.

The inventors have discovered that it is nearly impossible to cut through all field residue with a coulter blade 8021 ahead of the soil sample collection knife assembly 8120. If there is an excessive laterally open clearance between these two components, uncut residue will wrap around the leading edge of the knife assembly and cause disruption of the soil flow and eventually plugging which prevent samples from being collection. To remedy this problem, the forward leading edge 8120a of the collection knife assembly is fitted with an arcuately curved blade guide element 8150. Guide element 8150 is configured to create an overlapping arrangement between the circumferential cutting edge 8151 of the coulter blade 8021 and leading edge 8120a of knife assembly 8120 which prevents crop residue from plugging the gap between the knife and blade. This combination is very effective at cutting through soil and crop residue while eliminating the crop residue plugging problem and operational issues, thereby eliminating downtime to manually remove the residue. The guide element 8150 advantageously aids in keeping the coulter and knife moving together for smoother flow through the soil and reduced draft (i.e. soil depth) loading on the knife assembly 8120 (i.e. independent side to side lateral forces or motion imparts to the knife assembly).

Blade guide element 8150 is fixedly and rigidly coupled to leading edge 8120*a* of knife assembly 8120. The guide element may be secured to knife assembly 8120 via welding, fasteners (e.g. threaded bolts, rivets, etc.), or any other suitable mechanical coupling method. Guide element 8150 has an elongated arcuately curved body which defines forward facing recess 8152 (see, e.g., FIGS. 78-79). The recess is configured to receive cutting edge 8151 of coulter blade 8020 partially therein in a manner which eliminates any lateral openings on either side of the interface between the coulter blade 8021 and knife assembly leading edge 8120*a*. Recess 8151 may be in the form of a V-shaped notch in one embodiment (see, e.g. FIG. 79). Leading edge 8120*a* of knife assembly 8120 may have an arcuately curved shape which substantially conforms to the curvature of the guide element 8150 and coulter blade. Preferably, the guide element has an arcuate length which extends for at least half of the height of the leading edge 8120*a* of knife assembly 8120 to cover portions of front blade element 8131 which can possibly engage the soil to prevent any lateral ingress of crop residue into the coulter blade and knife assembly interface. In one embodiment, blade guide element 8150 covers the entire portion of front blade element 8131 below guide ski 8160 and extends above the ski for a distance.

Blade guide element 8150 is preferably formed of a suitable metallic material since the cutting edge of coulter blade 8021 may ride inside and slideably engage the side surfaces of the guide element within the blade recess 8151 as the blade rotates when pulled through the agricultural field. In one embodiment, the guide element 8150 may comprise separate top and bottom guide inserts 8150*a*, 8150*b* formed of a suitably hard wear resistant metal. The guide inserts 8150*a*, 8150*b* are located at the terminal top and bottom ends of the guide element 8150 (see, e.g. FIGS. 80-81) and may be separated attached to the leading edge of the knife assembly 8120. The guide inserts if used have the same V-shaped notched recess 8152 as the portions of guide element 8150 therebetween. The guide inserts are located the points on the knife leading edge 8120*a* on front blade element 8131 that will experience much higher abrasion and wear from side loading as the knife assembly moves through the soil. The knife is made of metal such as steel which is more structural and ductile, while the inserts may be made of a superior wear resistant material such as tungsten carbide. The inserts overlap more than the knife body because they experience higher force loading against the coulter and therefore spread that force over more surface area. In some embodiments, the blade guide element 8150 including guide inserts 8150*a*, 8150*b* may be formed of wear resistant tungsten carbide. Any suitable means may be used to attach the guide element and inserts to the front blade element 8131.

According to another aspect of the soil sample collection system 8000, knife assembly 8120 in some embodiments may include low stick, low friction pads 8170. Depending on the soil type and moisture level, the soil may have a tendency to adhere or stick to surfaces of ground engaging components (i.e. coulter blade 8021 and knife assembly 8120). This may eventually lead to buildup of soil deposits on these components that disrupts smooth soil flow over their exposed side surfaces and impedes proper collection of the soil sample into the collection spool 8040. This adherence is more likely to occur closer to ground or soil surface GS where side pressure against these components is lowest. At deeper levels or depths in the soil, the soil pressure is much greater and able to scour these component surfaces as the coulter blade and knife assembly move through the agricultural field. Non-rotating components such as the knife assembly are more susceptible to soil buildup than the coulter blade. Rotating component surfaces encounter the soil from different directions and angles which enables them with a self cleaning ability.

To overcome the foregoing soil adherence problem, low-profile planar pads 8170 formed of low stick or friction material are fixedly attached to both lateral side surfaces of the knife assembly 8120, including front blade element 8131 and rear blade element 8130 (including forward and rearward segments 8130*a*, 8130*b*). The low friction pads 8170 may have any suitable configuration and thickness (measured in the lateral or transverse direction to the horizontal axis HA and direction of travel of the collection apparatus. The configuration may be dictated at least in part of the parts of the knife assembly 8120 to which the pads are mounted. In one embodiment, pads 8170 can comprise low friction materials such as polymers including ultra high molecular weight polyethylene (UHMW-PE) or similar high performance low friction materials having mechanical properties able to withstand the abrasive and abusive environment of ground engaging equipment.

Figure 77:
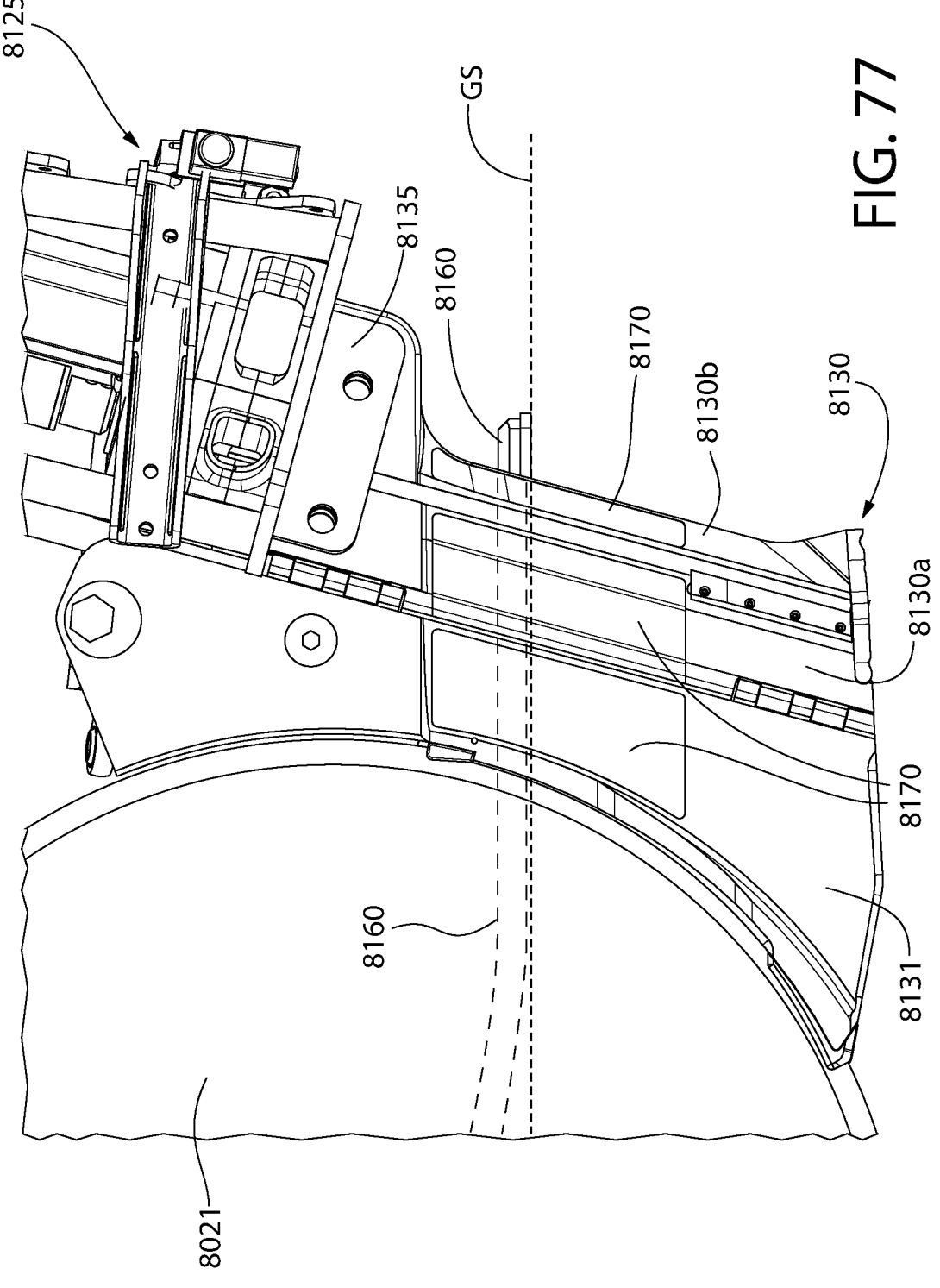
FIG. 77 is a partial right side view of the coulter blade and knife assembly of the collection apparatus.
Figure 78:
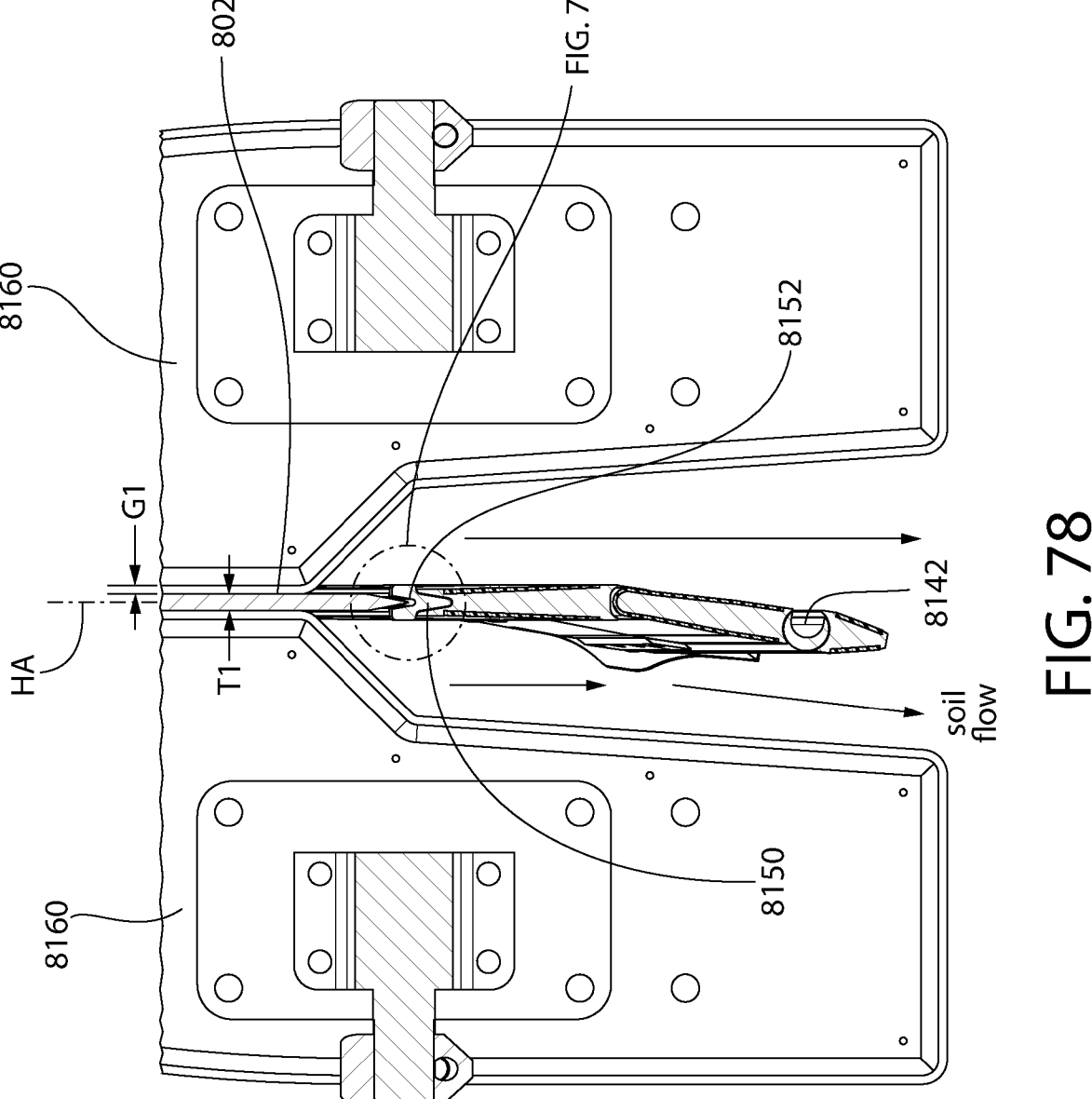
FIG. 78 is a top cross sectional view of the collection apparatus showing the guide skis and laterally pivotable rear blade element of the knife assembly.
Figure 79:
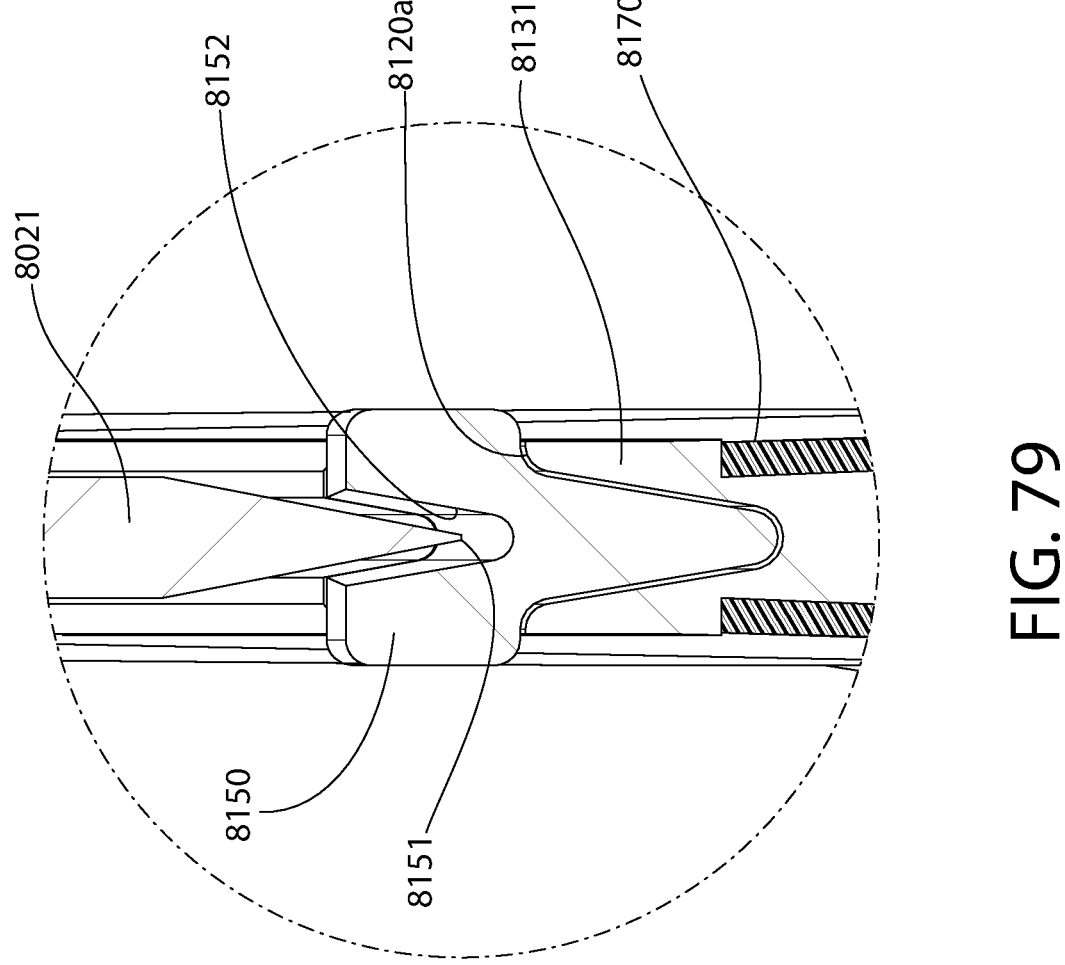
FIG. 79 is an enlarged details taken from FIG. 78.

In preferred but non-limiting embodiment, the low friction pads 8170 each have a vertical extent or height which covers at least the portions lateral side surfaces 8127 of knife assembly 8120 (front and rear blade elements 8131, 8130) adjacent to the soil surface GS where side pressure of the soil against the knife assembly low allowing soil accumulations to build up. In the present soil sample collection apparatus 8002, as shown in FIG. 77 and others, the soil surface GS coincides with the location of the guide skis 8160 having bottom surfaces which ride on top of the soil. Accordingly, the low friction pads 8170 are located adjacent to and inward of each guide ski on knife assembly 8120. To further discourage the formation of soil adherence and accumulations on the knife assembly at or near the soil level or surface, the low friction pads 8170 preferably have a height in one embodiment which extends partly above and below guide skis 8160 to shed soil as the knife assembly travels through the agricultural field. In this embodiment, the pads do not extend for the full height of the front or rear blade elements of knife assembly 8120 as shown. The pads have an axial front to rear width (measured along horizontal axis HA and the direction of travel) which extends for at least a majority of or substantially the entirety of the axial width of each knife blade elements and segment.

It bears particular note that the use of low stick or friction surfaces provided by pads 8170 which contact the soil at its surface level become more critical when using the pivotable "ruddering" knife assembly 8120 disclosed as the knife surface intersects the walls of the soil trench or furrow created by leading coulter blade 8121 at an increased angle during sample collection.

The application of separate low-friction pads 8170 to the knife assembly 8120 has advantages over simply applying low-stick coatings to the knife blades by being able to wear and shed material while remaining effective and permitting easy replacement when needed. The low friction pads 8170 may be mounted and inset within a complementary configured pocket 8171 formed on the knife assembly side surfaces for retention and maintaining streamlined knife side surfaces. Accordingly, the outward facing planar or flat surfaces of the pads may be flush with the outward facing lateral side surfaces of the knife assembly. This arrangement advantageously eliminates protruding edges which could engage the soil causing soil adhesion and accumulations on the knife assembly as the soil passes by the knife assembly resulting in increased drag and friction on the knife assembly. The formation of soil accumulations on the knife assembly may also adversely interference with properly collection of a soil sample by the collection spool 8040. Any suitable means available to those skilled in the art may be used to attached retain the pads 8170 in pockets 8171 of the knife assembly.

According to another aspect of the soil sample collection system 8000, the relationship in depth that the coulter blade 8021 and knife assembly 8120 each penetrate the soil is especially selected to optimize the positive collection of soil samples. Traditional agricultural implements which may use a coulter and knife combination standardly set the coulter shallower and the knife deeper in the soil. While this relationship is typical for some tillage tools requiring deep depth knife shanks, it is not effective for the present purpose of collecting soil samples from the walls of the trough or furrow in the soil created by the coulter blade which leads the knife assembly to the rear.

The inventors have discovered that an ideal relationship for collecting soil sample using sample collection apparatus 8002 is to position the coulter blade 8021 slightly deeper in the soil than the trailing knife assembly 8120 as seen in FIG. 70. Accordingly, the bottom of coulter blade 8021 projects downward farther in the soil from the bottom surface of guide skis 8060 which ride on the soil surface GS than the bottom of knife assembly 8120. With this arrangement, the knife assembly advantageously does not encounter untilled and compacted soil. All soil passing by the knife assembly has been previously loosened by coulter blade so that the knife assembly rides within the trough or furrow created by the blade. This allows the collection spool 8040 of the knife assembly to readily capture the loosened soil from the walls of the furrow during sampling.

Other considerations are applicable and advantageous to positioning the bottom of the leading coulter blade 8021 deeper/lower in the soil than the bottom of the trailing knife assembly 8120. As a rolling mechanism, the coulter blade requires less force per depth of soil penetration to pull it through the soil with sampling trailer 8103 and the motor-driven vehicle 8110 coupled thereto, as previously described herein. Accordingly, keeping the bottom of the coulter blade 8021 lower/deeper in the soil than the non-rotatable knife assembly 8120 helps reduce the overall pull force (draft in agricultural terms) loading for the powered vehicle and fuel consumption. A deeper coulter blade is also more effective at cutting through field residue before it encounters the knife assembly. Furthermore, as a rolling mechanism, the coulter is more effective when contacting embedded or surface soil obstructions (e.g., rocks, tree stumps/branches, etc.). The coulter blade is therefore more likely to roll over these obstruction, push them out of the way of the knife assembly 8121 to the side, or cut through them. The coulter may allow the coulter/knife combination to roll over an immovable obstruction such as large field rocks without damage. Finally, the coulter is also a more expendable component which can act as a sacrificial part to protect the more expensive and complexly constructed knife assembly.

According to another aspect of the soil sample collection system 8000, a power driven coulter blade 8121 may be provided in some embodiments. Most agricultural field conditions encountered have soils which are firm enough to grip the side of the coulter blade and keep it turning while traveling through the soil via friction. The exception to this is especially soft or slick soils which may not positively grip the coulter blade at all times. In these situations, supplemental power transmitted to the hub and blade may be needed to keep the coulter blade rotating as it travels through the soil.

Figure 74:
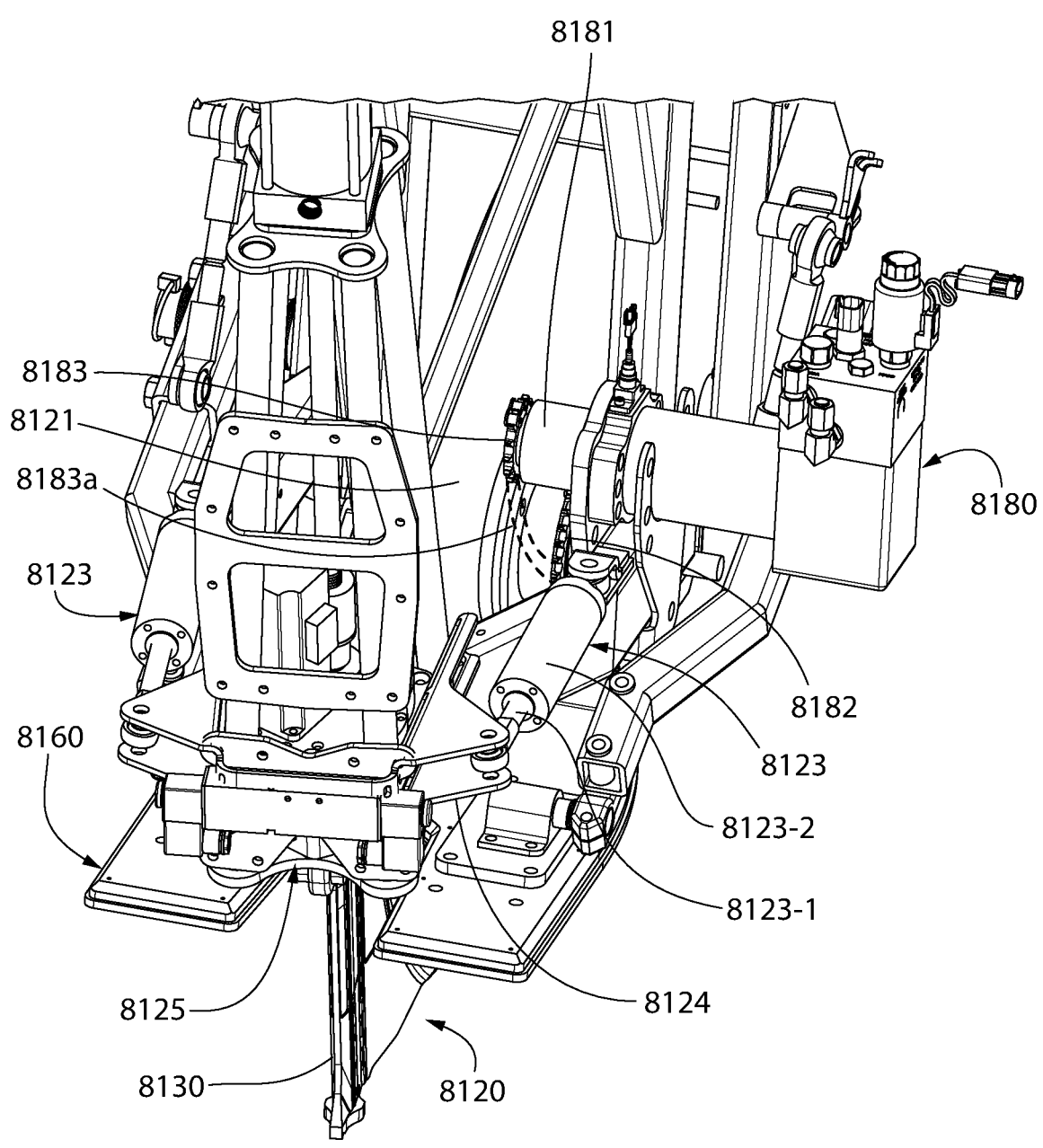
FIG. 74 is a partial top rear perspective view of the left side of the collection apparatus showing a motorized (driven) coulter blade with motor.

FIG. 74 shows one non-limiting embodiment of a powered coulter blade 8121 including a drive motor such as without limitation hydraulic drive motor 8180 and optionally an overrunning clutch 8181. Other type drives may be provided including electric motors or pneumatic drive motors which are all broadly encompassed under the term "drive motor." In one non-limiting embodiment, clutch 8181 coupled to and driven by motor 8180 includes drive sprocket 8183 which is coupled to driven sprocket 8182 on the coulter blade hub 8023 by drive chain 8183*a* (shown schematically by dashed lines) to rotate the blade. This advantageously allows the coulter blade to always be able to spin freely regardless of the drive status, particularly in the scenario where the coulter wants to naturally spin faster than the drive system coupled to the blade than the drive motor would allow the blade to rotate via frictional engagement with the soil. Overrunning clutch are configured to transmit torque in one rotational direction, thereby allowing the coulter blade 8021 to "free wheel" in the other direction. Any suitable commercially-available overrunning clutch and motor may be used.

The torque and power applied to the coulter blade 8121 via the blade drive system may be delivered through multiple operational arrangements as demonstrated by the following non-limiting examples including force applied or speed control. In a force applied arrangement, the drive mechanism powered by motor 8180 may be configured to deliver a prescribed predetermined drive force to the coulter blade regardless of the coulter actual speed as it is pulled through the soil. Various operational configurations of speed control may be used including: 1. Underdriven—the drive mechanism is closed loop controlled with speed feedback and maintains its speed under the normal coulter speed relative to ground speed, but if the coulter struggles, the overrunning clutch locks and the drive mechanism provides force necessary to keep the coulter turning. 2. Speed Matching—the drive mechanism receives speed feedback and matches its speed with that of ground travel speed. 3. Overdriving—the drive mechanism is always in a state of attempting to turn the coulter faster than ground travel speed. Supplemental torque and power may be transmitted to the coulter blade 8121 through, but not limited to hydraulic, electric, pneumatic, chains, belts, gears/sprockets, pulleys, etc.

Figure 75:
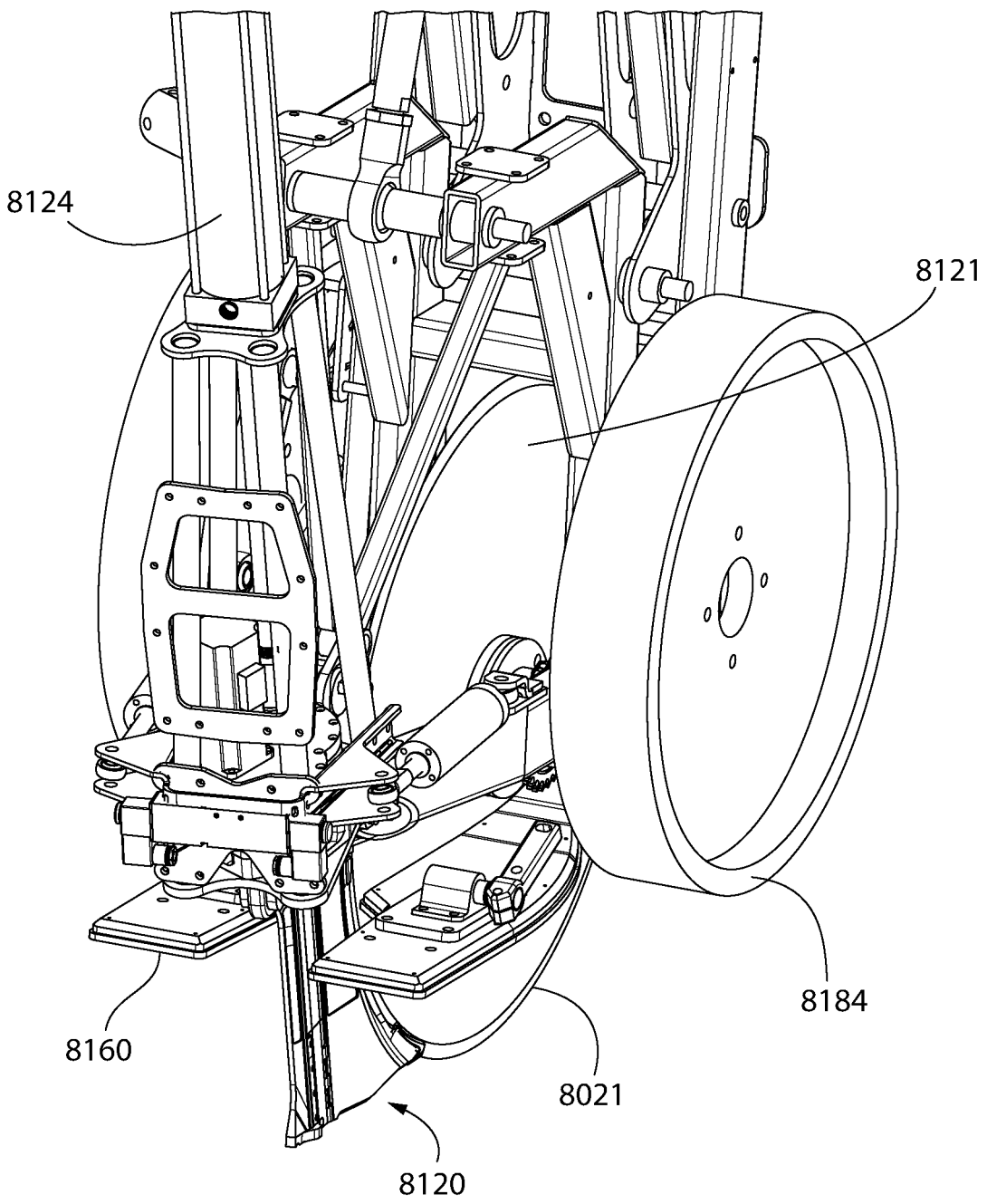
FIG. 75 is a partial top rear perspective view of the left side of the collection apparatus showing an alternative ground engaging drive wheel which rotates the coulter blade.
Figure 76:
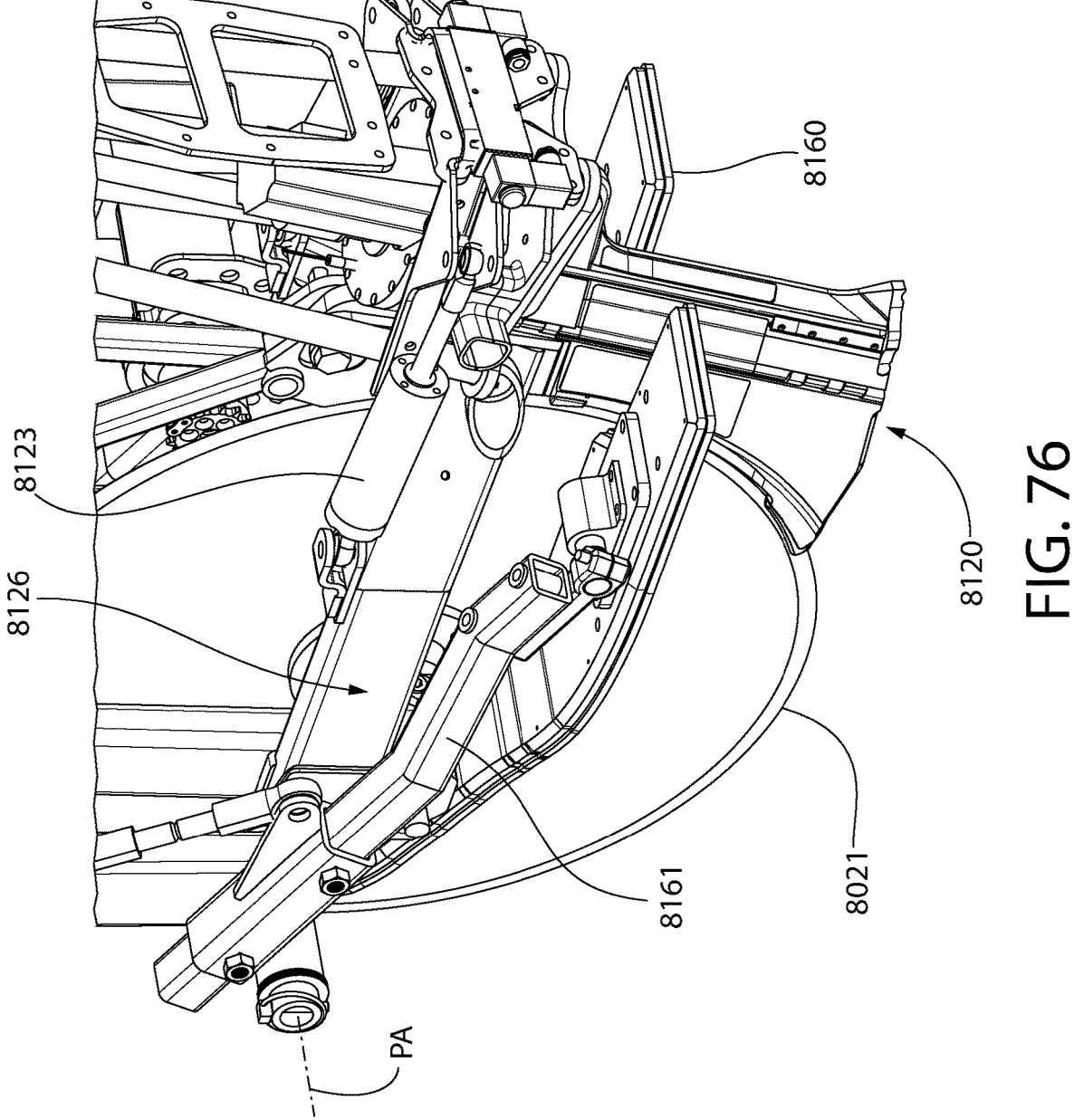
FIG. 76 is a partial top rear perspective view of the right side of the collection apparatus.

FIG. 75 shows an alternative motor-less coulter blade drive system comprising a ground surface engaging drive wheel 8184 coupled to the hub 8023 of the blade. Supplemental power to drive and rotate the coulter blade 8121 is provided as the drive wheel 8184 rolls along the soil surface in the field. In some embodiments, a pair of drive wheels 8184 may be provided (i.e. one on each lateral side of the coulter blade outboard of the guide skis 8160). A 1:1 drive ratio may be provided in one embodiment (i.e. coulter blade 8121 rotates in unison with drive wheel 8184). In other embodiments, the drive system may be configured to rotate the coulter blade less than the drive wheel such as 1.5:1 wheel to coulter blade rotations, 2:1, etc.).

A process or method for capturing a soil sample from an agricultural field using the foregoing angularly pivotable "ruddering" knife assembly 8120 of collection apparatus 8002 will now be briefly described based on the foregoing description. The method generally comprises first providing the collection apparatus 8002 comprising a rotatable coulter blade 8021 or 8121 (powered version), and the "ruddering" knife assembly 8120 arranged proximate to the coulter blade and comprising at least one rotatable collection spool comprising a collection cavity configured for capturing the soil sample. The rear blade element 8130 of the knife assembly may be placed axially inline with the front blade element 8131 in either the locked or free float condition.

The next step includes pulling the collection apparatus 8002 through the soil in a direction of travel generally parallel to a surface of the soil (accounting for surface undulations in the terrain). When the soil sample is desired to be collected, the rear blade element may be angularly moved or displaced in either the lateral left or right directions as shown in FIGS. 84-85. The centerline CLI of the rear blade element assumes an acute angle A1 orientation to the front blade element 8131 and horizontal axis HA of the collection apparatus, which passes through the hub of the coulter blade and coincides with the direction or line of travel of the apparatus through agricultural field AF.

The method continues with rotating the collection spool 8040 from a closed position in which the sample collection cavity 8042 is shielded from the soil to an open position in which the collection cavity is outwardly exposed to the soil for capturing the soil sample (see, e.g., FIGS. 84-85). The next step is capturing the soil sample in the collection cavity of the collection spool. Because rear blade element 8130 is angularly disposed to the front blade element 8131, a greater amount of soil pressure or force is applied to the rear blade element as it engages the wall WF of the trough or furrow created by the leading front blade element than when the rear blade element is pulled through the furrow inline with the coulter blade 8021 and front blade element. This forces and compacts the soil more positively into the sample collection cavity 8042 of collection spool 8040, thereby resulting in positive retention and capture of the sample.

After the sample is captured, the method continues with rotating the collection spool 8040 back to the closed position for retaining the soil sample. The rear blade element 8130 may then be pivotably moved or rotated back inline with front blade element 8131. The method may then further comprise raising the collection spool 8040 while still in the closed position, and then ejecting the soil sample from the collection cavity 8042 of the spool for storage and/or further processing and chemical analysis of the sample as shown in FIG. 1.

In the above method/process, it bears noting that collection spool 8040 may optionally be rotated to the open position before pivoting/rotating the rear blade element 8130 to the above angled position to directly engage the furrow walls WF. It further bears noting that variations in the order of the foregoing steps and additional steps may be used in other embodiments of the soil sample capture method or process.

EXAMPLES

The following are nonlimiting examples.

Example 1—a soil sample collection system (8000) comprising: a sample collection vehicle (2802, 8003, 8100) comprising a pair of front wheels (8106) and a pair of rear wheels (8107); a support frame (8001) mounted to the sample collection vehicle (2802, 8003, 8100); and a sample collection apparatus (8002) supported by the support frame (8001) and comprising soil engaging elements (8020, 8120, 8021, 8121) disposed between the front and rear wheels, the soil engaging elements (8020, 8120, 8021, 8121) configured to engage the soil and collect the soil sample as the sample collection vehicle (2802, 8003, 8100) travels along a surface of the soil.

Example 2—the soil sample collection system (8000) according to Example 1, wherein the soil engaging elements (8020, 8120, 8021, 8121) are disposed between a transverse front wheel axis (AX1) extending through the front wheels (8106) and a transverse rear wheel axis (AX2) extending through the rear wheels (8107).

Example 3—the soil sample collection system (8000) according to Examples 1 or 2, wherein the soil engaging elements (8020, 8120, 8021, 8121) include a coulter blade (8021, 8121) rotatably coupled to the support frame (8001), a knife assembly (8020, 8120) coupled to the support frame (8001) proximate to the coulter blade (8021, 8121), and a collection spool (8040) movably mounted to the knife assembly (8020, 8120), the collection spool (8040) comprising a collection cavity (8042) configured to capture the soil sample.

Example 4—the soil sample collection system (8000) according to Example 3, wherein the collection spool (8040) is rotatably and vertical moveable relative to the knife assembly (8020, 8120).

Example 5—the soil sample collection system (8000) according to Example 3, wherein the coulter blade (8021, 8121) is disposed forward of and axially aligned with the knife assembly (8020, 8120).

Example 6—the soil sample collection system (8000) according to any one of Examples 1-5, wherein the soil engaging elements (8020, 8120, 8021, 8121) are disposed equidistant between opposing lateral sides (8105) of the sample collection vehicle (2802, 8003, 8100).

Example 7—the soil sample collection system (8000) according to Example 2, wherein the sample collection vehicle (2802, 8003, 8100) is a trailer (8100) comprising a hitch (8102) configured for coupling to an engine-powered vehicle (8003) operable to pull the trailer (8100) along the surface of the soil.

Example 8—the soil sample collection system (8000) according to Example 7, wherein the sample collection apparatus (8002) is disposed in a central equipment opening (8108) defined by a frame (8103) of the trailer (8100).

Example 9—the soil sample collection system (8000) according to Example 8, wherein the central equipment opening (8108) has a length which extends for a majority of a length of the frame (8103) of the trailer (8100) and a width which extends for a majority of a width of the frame (8103) of the trailer (8100).

Example 10—the soil sample collection system (8000) according to Examples 8 or 9, wherein each of the front wheels (8106) and rear wheels (8107) are rotatably mounted to the trailer (8100) by individual torsion axles (8109) which do not extend laterally through the central equipment opening (8108).

Example 11—the soil sample collection system (8000) according to Example 10, wherein each torsion axle (8109) is supported by an associated spring suspension member (8113) coupled to the frame (8103) of the trailer (8100).

Example 12—the soil sample collection system (8000) according to Example 3, wherein the knife assembly (8020, 8120) comprises a blade guide element (8150) including a forwardly open recess (8152) which receives a peripheral cutting edge (8151) of the coulter blade (8021, 8121) partially therein.

Example 13—the soil sample collection system (8000) according to Example 12, wherein the coulter blade (8021, 8121) is configured to be linearly adjustable in a forward and rearward direction relative to the knife assembly (8020, 8120) for adjusting a depth of the coulter blade (8021, 8121) in the recess (8152) of the blade guide element.

Example 14—the soil sample collection system (8000) according to Example 1, wherein the sample collection apparatus (8002) is angularly adjustable relative to the surface of the soil.

Example 15—a soil sample collection system (8000) comprising: a support frame (8001) configured for mounting to a vehicle (2802, 8003); a collection apparatus (8002) comprising: a coulter blade (8021, 8121) rotatably coupled to the support frame (8001); a knife assembly (8020, 8120) coupled to the support frame (8001) proximate to and at the rear of the coulter blade (8021, 8121), the knife assembly (8020, 8120) comprising a front blade element (8031, 8131) and a rear blade element (8030, 8130) coupled to the front blade element (8031, 8131); wherein the rear blade element (8030, 8130) is configured to engage the soil and collect the soil sample as the vehicle (2802, 8003) travels along a surface of the soil.

Example 16—the soil sample collection system (8000) according to Example 15, wherein the rear blade element (8030, 8130) is pivotably movable.

Example 17—the soil sample collection system (8000) according to Example 16, wherein the rear blade element (8030, 8130) is hingedly coupled to the front blade element (8031, 8131).

Example 18—the soil sample collection system (8000) according to Example 17, wherein the rear blade element (8030, 8130) is angularly moveable relative to the front blade element (8031, 8131) in opposing lateral directions about a substantially vertical pivot axis.

Example 19—the soil sample collection system (8000) according to Example 18, wherein the collection apparatus (8002) further comprises a pair of rudder actuators (8123) operably coupled to the rear blade element (8030, 8130), the rudder actuators (8123) operable to pivot the rear blade element (8030, 8130) in opposing lateral directions.

Example 20—the soil sample collection system (8000) according to Example 19, wherein the rear blade element (8030, 8130) is rigidly coupled to a blade support structure (8125) pivotably coupled to the support frame (8001) and the rudder actuators (8123) are coupled to the blade support structure (8125).

Example 21—the soil sample collection system (8000) according to Example 16, wherein the rear blade element (8030, 8130) comprises a movable collection spool (8040), the collection spool (8040) being selectively rotatable and comprising a collection cavity (8042) configured to capture the soil sample.

Example 22—the soil sample collection system (8000) according to Example 21, further comprising a spool drive mechanism (8070a) operably coupled to the collection spool (8040) and operable to rotate the collection spool (8040).

Example 23—the soil sample collection system (8000) according to Examples 21 or 22, wherein the collection spool (8040) is rotatable between a first position in which the collection cavity (8042) is shielded from the soil, and a second position in which the collection cavity (8042) is outwardly exposed to the soil to collect the soil sample.

Example 24—the soil sample collection system (8000) according to any one of Examples 21-23, wherein the collection spool (8040) is further vertically movable in the rear blade element (8030, 8130).

Example 25—the soil sample collection system (8000) according to any one of Examples 15-24, wherein the collection apparatus (8002) includes at least one guide ski (8060, 8160) disposed adjacent to the coulter blade (8021, 8121) and configured to ride along the surface of the soil.

Example 26—the soil sample collection system (8000) according to Example 25, wherein the at least one guide ski (8060, 8160) comprises an upturned wedge shaped front end portion (8160a).

Example 27—the soil sample collection system (8000) according to Example 24 or 26, wherein the knife assembly (8020, 8120) further comprises a plurality of low friction pads (8170) disposed adjacent to the at least one guide ski (8060, 8160) on lateral side surfaces of the knife assembly (8020, 8120).

Example 28—the soil sample collection system (8000) according to any one of Examples 25-27, wherein the at least one guide ski (8060, 8160) is spaced apart from the coulter blade (8021, 8121) by a gap (G1) between less than a thickness of the coulter blade (8021, 8121) and no more than five times the thickness, or optionally twice the thickness.

Example 29—the soil sample collection system (8000) according to Example 15, wherein the coulter blade (8021, 8121) is arranged to vertically penetrate the soil to a depth deeper than the knife assembly (8020, 8120).

Example 30—the soil sample collection system (8000) according to any one of Examples 15-29, wherein the coulter blade (8021, 8121) is coupled to and rotated by a motor (8180).

Example 31—the soil sample collection system (8000) according to Example 30, further comprising an overrunning clutch operably coupled between the motor (8180) and the coulter blade (8021, 8121).

Example 32—the soil sample collection system (8000) according to any one of Examples 15-29, further comprising a drive wheel (8184) coupled to the coulter blade (8021, 8121) and operable to rotate the coulter blade (8021, 8121), the drive wheel (8184) configured to roll on the surface of the soil when the collection apparatus (8002) is pulled through the soil.

Example 33—a method for capturing a sample of soil from an agricultural field comprising: providing a collection apparatus (8002) comprising a rotatable coulter blade (8021, 8121), and a knife assembly (8020, 8120) arranged proximate to the coulter blade (8021, 8121) and comprising a front blade element (8031, 8131) and a rear blade element (8030, 8130); pulling the collection apparatus (8002) through the soil in a direction of travel; pivotably moving the rear blade element (8030, 8130) laterally to an angular position relative to the front blade element (8031, 8131) of the knife assembly (8020, 8120); rotating a collection spool (8040) in the rear blade element (8030, 8130) from a closed position to an outwardly open position in which the collection cavity (8042) is exposed to the soil; capturing the soil sample in the collection cavity (8042) of the collection spool (8040); and rotating the collection spool (8040) back to the closed position for retaining the soil sample.

Example 34—the method according to Example 33, further comprising raising the collection spool (8040) while in the closed position; and ejecting the soil sample from the collection cavity (8042).

Example 35—the method according to Examples 33 or 34, wherein the rear blade element (8030, 8130) is hingedly coupled to the front blade element (8031, 8131).

While the foregoing description and drawings represent some example systems, it will be understood that various additions, modifications and substitutions may be made therein without departing from the spirit and scope and range of equivalents of the accompanying claims. In particular, it will be clear to those skilled in the art that embodiments of the present disclosure may be embodied in other forms, structures, arrangements, proportions, sizes, and with other elements, materials, and components, without departing from the spirit or essential characteristics thereof. In addition, numerous variations in the methods/processes described herein may be made. One skilled in the art will further appreciate that the embodiments of the present disclosure may be used with many modifications of structure, arrangement, proportions, sizes, materials, and components and otherwise, used in the practice of the embodiments of the present disclosure, which are particularly adapted to specific environments and operative requirements without departing from the principles of the present embodiments of the present disclosure. The presently disclosed embodiments are therefore to be considered in all respects as illustrative and not restrictive, the scope of the embodiments of the present disclosure being defined by the appended claims and equivalents thereof, and not limited to the foregoing description or embodiments. Rather, the appended claims should be construed broadly, to include other variants and embodiments, which may be made by those skilled in the art without departing from the scope and range of equivalents of the embodiments of the present disclosure.

The invention claimed is:

1. A soil sample collection system comprising:
a support frame configured for mounting to a vehicle;
a collection apparatus comprising:
    a coulter blade rotatably coupled to the support frame; and
    a knife assembly coupled to the support frame proximate to and at the rear of the coulter blade, the knife assembly comprising a front blade element and a rear blade element pivotably coupled to the front blade element so that the rear blade element is pivotable relative to the front blade element;
    wherein the rear blade element is configured to engage the soil and collect the soil sample as the vehicle travels along a surface of the soil.

2. The soil sample collection system according to claim 1, wherein the rear blade element is angularly moveable relative to the front blade element in opposing lateral directions about a substantially vertical pivot axis.

3. The soil sample collection system according to claim 2, wherein the collection apparatus further comprises a pair of rudder actuators operably coupled to the rear blade element, the rudder actuators operable to pivot the rear blade element in opposing lateral directions.

4. The soil sample collection system according to claim 3, wherein the rear blade element is rigidly coupled to a blade support structure pivotably coupled to the support frame and the rudder actuators are coupled to the blade support structure.

5. The soil sample collection system according to claim 1, wherein the rear blade element comprises a movable collection spool, the collection spool being selectively rotatable and comprising a collection cavity configured to capture the soil sample.

6. The soil sample collection system according to claim 5, further comprising a spool drive mechanism operably coupled to the collection spool and operable to rotate the collection spool.

7. The soil sample collection system according to claim 5, wherein the collection spool is rotatable between a first position in which the collection cavity is shielded from the soil, and a second position in which the collection cavity is outwardly exposed to the soil to collect the soil sample.

8. The soil sample collection system according to claim 5, wherein the collection spool is further vertically movable in the rear blade element.

9. The soil sample collection system according to claim 1, wherein the collection apparatus includes at least one guide ski disposed adjacent to the coulter blade and configured to ride along the surface of the soil.

10. The soil sample collection system according to claim 9, wherein the at least one guide ski comprises an upturned wedge shaped front end portion.

11. A soil sample collection system comprising:
a support frame configured for mounting to a vehicle;
a collection apparatus comprising:
    a coulter blade rotatably coupled to the support frame; and
    a knife assembly coupled to the support frame proximate to and at the rear of the coulter blade, the knife assembly comprising a front blade element and a rear blade element coupled to the front blade element;
    wherein the rear blade element is configured to engage the soil and collect the soil sample as the vehicle travels along a surface of the soil;
wherein the collection apparatus includes at least one guide ski disposed adjacent to the coulter blade and configured to ride along the surface of the soil;
wherein the knife assembly further comprises a plurality of low friction pads disposed adjacent to the at least one guide ski on lateral side surfaces of the knife assembly.

12. The soil sample collection system according to claim 9, wherein the at least one guide ski is spaced apart from the coulter blade by a gap between less than a thickness of the coulter blade and no more than five times the thickness, or optionally twice the thickness.

13. The soil sample collection system according to claim 1, wherein the coulter blade is arranged to vertically penetrate the soil to a depth deeper than the knife assembly.

14. The soil sample collection system according to claim 1, wherein the coulter blade is coupled to and rotated by a motor.

15. The soil sample collection system according to claim 14, further comprising an overrunning clutch operably coupled between the motor and the coulter blade.

16. The soil sample collection system according to claim 1, further comprising a drive wheel coupled to the coulter blade and operable to rotate the coulter blade, the drive wheel configured to roll on the surface of the soil when the collection apparatus is pulled through the soil.

17. The soil sample collection system of claim 1, wherein the rear blade element of the knife assembly further comprises a forward blade segment and a rearward blade segment mounted to a base plate in a horizontally spaced apart manner, the forward blade segment and the rearward blade segment collectively defining a slot configured to receive a soil sample collection device.

18. A soil sample collection system comprising:
a sample collection vehicle;

a sample collection apparatus mounted to the sample collection vehicle, the sample collection apparatus comprising:

a furrow creating device configured to engage soil to create a furrow in the soil; and a knife assembly rearward of the furrow creating device, the knife assembly comprising a front blade element and a rear blade element, the rear blade element being moveable relative to the front blade element, the knife assembly configured to travel through the furrow created by the furrow creating device;

wherein the rear blade element is configured to engage the soil and collect a soil sample as the sample collection vehicle travels along a surface of the soil.

19. The soil sample collection system according to claim 18, further comprising a soil sample collection device disposed in the rear blade element, the soil sample collection device being selectively rotatable and comprising a collection cavity configured to capture the soil sample.

20. The soil sample collection system according to claim 19, wherein the knife assembly of the collection apparatus further comprises a pair of rudder actuators configured to actuate the rear blade element to force the soil sample collection device into a sidewall of the furrow created by the furrow creating device to capture the soil sample.

\*   \*   \*   \*   \*